US009994877B2

(12) United States Patent
Chung et al.

(10) Patent No.: US 9,994,877 B2
(45) Date of Patent: Jun. 12, 2018

(54) YEAST CELL HAVING ACID TOLERANCE, METHOD OF PREPARING YEAST CELL AND USE THEREOF

(71) Applicant: Samsung Electronics Co., Ltd., Suwon-si, Gyeonggi-do (KR)

(72) Inventors: Soonchun Chung, Seoul (KR); Jinha Kim, Namyangju-si (KR); Kwangmyung Cho, Seongnam-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days. days.

(21) Appl. No.: 15/153,492

(22) Filed: May 12, 2016

(65) Prior Publication Data

US 2016/0333380 A1 Nov. 17, 2016

(30) Foreign Application Priority Data

May 12, 2015 (KR) ........................ 10-2015-0066250

(51) Int. Cl.

| | |
|---|---|
| ***C12N 1/14*** | (2006.01) |
| ***C12P 7/42*** | (2006.01) |
| ***C12N 15/81*** | (2006.01) |
| ***C12N 9/04*** | (2006.01) |
| ***C12N 9/88*** | (2006.01) |
| ***C12N 9/02*** | (2006.01) |
| ***C12N 15/52*** | (2006.01) |

(52) U.S. Cl.

CPC .............. *C12P 7/42* (2013.01); *C12N 9/0006* (2013.01); *C12N 9/0008* (2013.01); *C12N 9/88* (2013.01); *C12N 15/52* (2013.01); *C12N 15/81* (2013.01); *C12Y 101/01001* (2013.01); *C12Y 101/01008* (2013.01); *C12Y 101/01027* (2013.01); *C12Y 101/01028* (2013.01); *C12Y 101/01094* (2013.01); *C12Y 101/02003* (2013.01); *C12Y 101/02004* (2013.01); *C12Y 101/05003* (2013.01); *C12Y 102/0101* (2013.01); *C12Y 102/01004* (2013.01); *C12Y 401/01001* (2013.01)

(58) Field of Classification Search

CPC ................................. C12P 7/05; C12R 1/8656
USPC ............................................ 435/139, 254.21
See application file for complete search history.

(56) References Cited

U.S. PATENT DOCUMENTS

| | | | |
|---|---|---|---|
| 7,696,333 | B1 | 4/2010 | Ishida et al. |
| 2015/0225752 | A1 | 8/2015 | Lim et al. |

OTHER PUBLICATIONS

Abbott et al., Generic and specific transcriptional responses to different weak organic acids in anaerobic chemostat cultures of *Saccharomyces cerevisiae, FEMS Yeast Research*, 7(6):819-833, (2007).

Rossi et al., Effect of HXT1 and HXT7 hexose transporter overexpression on wild-type and lactic acid producing *Saccharomyces cerevisiae* cells, *Microbial Cell Factories*, 9(15): 1-10 (2010).

Sugiyama et al., Nuclear Localization of Haa1, Which Is Linked to Its Phosphorylation Status, Mediates Lactic Acid Tolerance in *Saccharomyces cerevisiae*, Applied and Environmental Microbiology, 80 (11):3488-3495 (2014).

Suzuki et al., Disruption of multiple genes whose deletion causes lactic-acid resistance improves lactic-acid resistance and productivity in *Saccharomyces cerevisiae, Journal of Bioscience and Bioengineering*, 115(5), 467-474 (2013).

Upadhyaya et al., Metabolic engineering as a tool for enhanced lactic acid production, *Cell Press: Trends in Biotechnology*, 32(12): 637-644 (2014).

*Primary Examiner* — Tekchand Saidha
(74) *Attorney, Agent, or Firm* — Leydig, Voit & Mayer, Ltd.

(57) ABSTRACT

Provided are a genetically engineered yeast cell having increased activity of SUL1, STR3, HXT7, ERR1, GRX8, MXR1, GRE1, MRK1, AAD10 or a combination thereof, compared to a parent cell, and also having acid tolerance, a method of preparing the same, and a method of producing lactate using the same.

18 Claims, 3 Drawing Sheets

SEQUENCE LISTING

<160> NUMBER OF SEQ ID NOS: 171

<210> SEQ ID NO 1
<211> LENGTH: 859
<212> TYPE: PRT
<213> ORGANISM: Saccharomyces cerevisiae

<400> SEQUENCE: 1

Met Ser Arg Lys Ser Ser Thr Glu Tyr Val His Asn Gln Glu Asp Ala
1               5                   10                  15

Asp Ile Glu Val Phe Glu Ser Glu Tyr Arg Thr Tyr Arg Glu Ser Glu
            20                  25                  30

Ala Ala Glu Asn Arg Asp Gly Leu His Asn Gly Asp Glu Glu Asn Trp
        35                  40                  45

Lys Val Asn Ser Ser Lys Gln Lys Phe Gly Val Thr Lys Asn Glu Leu
    50                  55                  60

Ser Asp Val Leu Tyr Asp Ser Ile Pro Ala Tyr Glu Glu Ser Thr Val
65                  70                  75                  80

Thr Leu Lys Glu Tyr Tyr Asp His Ser Ile Lys Asn Asn Leu Thr Ala
                85                  90                  95

Lys Ser Ala Gly Ser Tyr Leu Val Ser Leu Phe Pro Ile Ile Lys Trp
            100                 105                 110

Phe Pro His Tyr Asn Phe Thr Trp Gly Tyr Ala Asp Leu Val Ala Gly
        115                 120                 125

Ile Thr Val Gly Cys Val Leu Val Pro Gln Ser Met Ser Tyr Ala Gln
    130                 135                 140

Ile Ala Ser Leu Ser Pro Glu Tyr Gly Leu Tyr Ser Ser Phe Ile Gly
145                 150                 155                 160

Ala Phe Ile Tyr Ser Leu Phe Ala Thr Ser Lys Asp Val Cys Ile Gly
                165                 170                 175

Pro Val Ala Val Met Ser Leu Gln Thr Ala Lys Val Ile Ala Glu Val
            180                 185                 190

Leu Lys Lys Tyr Pro Glu Asp Gln Thr Glu Val Thr Ala Pro Ile Ile
        195                 200                 205

Ala Thr Thr Leu Cys Leu Leu Cys Gly Ile Val Ala Thr Gly Leu Gly
    210                 215                 220

Ile Leu Arg Leu Gly Phe Leu Val Glu Leu Ile Ser Leu Asn Ala Val
225                 230                 235                 240

Ala Gly Phe Met Thr Gly Ser Ala Phe Asn Ile Ile Trp Gly Gln Ile

-continued

```
                245                 250                 255

Pro Ala Leu Met Gly Tyr Asn Ser Leu Val Asn Thr Arg Glu Ala Thr
            260                 265                 270

Tyr Lys Val Val Ile Asn Thr Leu Lys His Leu Pro Asn Thr Lys Leu
        275                 280                 285

Asp Ala Val Phe Gly Leu Ile Pro Leu Val Ile Leu Tyr Val Trp Lys
    290                 295                 300

Trp Trp Cys Gly Thr Phe Gly Ile Thr Leu Ala Asp Arg Tyr Tyr Arg
305                 310                 315                 320

Asn Gln Pro Lys Val Ala Asn Arg Leu Lys Ser Phe Tyr Phe Tyr Ala
                325                 330                 335

Gln Ala Met Arg Asn Ala Val Val Ile Val Val Phe Thr Ala Ile Ser
            340                 345                 350

Trp Ser Ile Thr Arg Asn Lys Ser Ser Lys Asp Arg Pro Ile Ser Ile
        355                 360                 365

Leu Gly Thr Val Pro Ser Gly Leu Asn Glu Val Gly Val Met Lys Ile
    370                 375                 380

Pro Asp Gly Leu Leu Ser Asn Met Ser Ser Glu Ile Pro Ala Ser Ile
385                 390                 395                 400

Ile Val Leu Val Leu Glu His Ile Ala Ile Ser Lys Ser Phe Gly Arg
                405                 410                 415

Ile Asn Asp Tyr Lys Val Val Pro Asp Gln Glu Leu Ile Ala Ile Gly
            420                 425                 430

Val Thr Asn Leu Ile Gly Thr Phe Phe His Ser Tyr Pro Ala Thr Gly
        435                 440                 445

Ser Phe Ser Arg Ser Ala Leu Lys Ala Lys Cys Asn Val Arg Thr Pro
    450                 455                 460

Phe Ser Gly Val Phe Thr Gly Gly Cys Val Leu Leu Ala Leu Tyr Cys
465                 470                 475                 480

Leu Thr Asp Ala Phe Phe Phe Ile Pro Lys Ala Thr Leu Ser Ala Val
                485                 490                 495

Ile Ile His Ala Val Ser Asp Leu Leu Thr Ser Tyr Lys Thr Thr Trp
            500                 505                 510

Thr Phe Trp Lys Thr Asn Pro Leu Asp Cys Ile Ser Phe Ile Val Thr
        515                 520                 525

Val Phe Ile Thr Val Phe Ser Ser Ile Glu Asn Gly Ile Tyr Phe Ala
    530                 535                 540

Met Cys Trp Ser Cys Ala Met Leu Leu Leu Lys Gln Ala Phe Pro Ala
545                 550                 555                 560

Gly Lys Phe Leu Gly Arg Val Glu Val Ala Glu Val Leu Asn Pro Thr
                565                 570                 575

Val Gln Glu Asp Ile Asp Ala Val Ile Ser Ser Asn Glu Leu Pro Asn
            580                 585                 590

Glu Leu Asn Lys Gln Val Lys Ser Thr Val Glu Val Leu Pro Ala Pro
        595                 600                 605

Glu Tyr Lys Phe Ser Val Lys Trp Val Pro Phe Asp His Gly Tyr Ser
    610                 615                 620

Arg Glu Leu Asn Ile Asn Thr Thr Val Arg Pro Pro Pro Pro Gly Val
625                 630                 635                 640

Ile Val Tyr Arg Leu Gly Asp Ser Phe Thr Tyr Val Asn Cys Ser Arg
                645                 650                 655

His Tyr Asp Ile Ile Phe Asp Arg Ile Lys Glu Glu Thr Arg Arg Gly
            660                 665                 670
```

-continued

```
Gln Leu Ile Thr Leu Arg Lys Lys Ser Asp Arg Pro Trp Asn Asp Pro
        675                 680                 685

Gly Glu Trp Lys Met Pro Asp Ser Leu Lys Ser Leu Phe Lys Phe Lys
    690                 695                 700

Arg His Ser Ala Thr Thr Asn Ser Asp Leu Pro Ile Ser Asn Gly Ser
705                 710                 715                 720

Ser Asn Gly Glu Thr Tyr Glu Lys Pro Leu Leu Lys Val Val Cys Leu
                725                 730                 735

Asp Phe Ser Gln Val Ala Gln Val Asp Ser Thr Ala Val Gln Ser Leu
            740                 745                 750

Val Asp Leu Arg Lys Ala Val Asn Arg Tyr Ala Asp Arg Gln Val Glu
        755                 760                 765

Phe His Phe Ala Gly Ile Ile Ser Pro Trp Ile Lys Arg Ser Leu Leu
    770                 775                 780

Ser Val Lys Phe Gly Thr Thr Asn Glu Glu Tyr Ser Asp Asp Ser Ile
785                 790                 795                 800

Ile Ala Gly His Ser Ser Phe His Val Ala Lys Val Leu Lys Asp Asp
                805                 810                 815

Val Asp Tyr Thr Asp Glu Asp Ser Arg Ile Ser Thr Ser Tyr Ser Asn
            820                 825                 830

Tyr Glu Thr Leu Cys Ala Ala Thr Gly Thr Asn Leu Pro Phe Phe His
        835                 840                 845

Ile Asp Ile Pro Asp Phe Ser Lys Trp Asp Val
    850                 855


<210> SEQ ID NO 2
<211> LENGTH: 2581
<212> TYPE: DNA
<213> ORGANISM: Saccharomyces cerevisiae

<400> SEQUENCE: 2

atgtcacgta agagctcgac tgaatatgtg cataatcagg aggatgctga tatcgaagta     60

tttgaatcag aataccgcac atatagggaa tctgaggcgg cagaaaacag agacggactt    120

cacaatggtg atgaggaaaa ttggaaggtt aatagtagta agcagaaatt tggggtaacg    180

aaaaatgagc tatcagatgt cctgtacgat tccattccag cgtatgaaga gagcacagtc    240

actttgaagg agtactatga tcattctatc aaaaacaatc taactgcgaa atcggcagga    300

agttacctcg tatctctttt tcctattata aaatggtttc ctcattataa ctttacgtgg    360

ggctatgctg atttagtggc aggaattaca gttggctgcg tactcgtgcc ccaatctatg    420

tcatacgcac aaatcgctag tttatctcct gaatatggtt tgtattcctc ctttattggt    480

gcgtttatat attctttgtt tgccacatcg aaagatgttt gtattggtcc ggtcgctgta    540

atgtcactac aaactgccaa agtcattgct gaagttctaa aaaaatatcc cgaagaccag    600

acagaagtta cagctcctat cattgcaact accctttgtt tgctttgtgg gattgtcgcc    660

actgggttgg gtatactgcg tttaggcttt ttagtggaac ttatttctct aaatgctgtt    720

gctggcttca tgaccggttc cgcatttaac atcatctggg gtcaaattcc ggctctcatg    780

ggatacaact cattagtgaa taccagagaa gcaacgtata aggttgtaat taacactctg    840

aaacatttac caaacacaaa gttagacgcc gtttttggct tgattccgtt ggtaatcctc    900

tatgtatgga aatggtggtg tggtacattt ggtataactt tggcagatag atattatcga    960

aatcaaccaa aggtagcaaa tagactgaaa tccttctatt tctatgcaca agctatgaga   1020
```

-continued

```
aatgccgtcg tcatagtagt ttttactgcc atatcgtgga gcataacaag aaacaaatct   1080

tcaaaagacc gtccaatcag tattctgggt acagttccct cgggcttaaa tgaggtggga   1140

gttatgaaaa tcccagacgg tctgctatct aatatgagtt cagaaatacc tgcttcaatt   1200

atcgttctgg tgttagaaca catcgctatt tcaaaatcct ttggtagaat taacgactac   1260

aaggttgtcc ctgaccaaga acttattgcg attggtgtga caaatttgat agggacattt   1320

tttcactcat atccagcaac tggtcattt tccagatctg ctttgaaagc aaaatgtaac   1380

gtgcgcactc cgttttctgg ggtattcact ggcggttgcg ttctattagc actttattgt   1440

ttaactgacg ccttcttttt cattcctaaa gcgacactat cggcggttat tattcatgct   1500

gtttctgatt tgctgacttc ttacaaaacc acctggacct tctggaagac caacccgtta   1560

gattgtatct catttatcgt tacagtgttc atcacagtat tttcatccat tgaaaatggt   1620

atatattttg caatgtgttg gtcatgtgca atgttactat tgaaacaggc tttccctgct   1680

ggtaaattcc ttggtcgtgt tgaggtggca gaagtattga acccaacagt acaagaggat   1740

attgatgctg tgatatcatc taatgaatta cctaatgaac tgaataaaca ggttaagtct   1800

actgttgagg ttttaccagc cccagagtat aagtttagcg taaagtgggt tccgttcgat   1860

catggatact caagagaatt gaatatcaat accacagttc ggcctcctcc accaggtgtc   1920

atagtctatc gtttgggtga tagctttact tacgtgaact gctcaaggca ttatgacatt   1980

atatttgatc gtattaagga agaaacaagg cgaggccaac ttataacctt aaggaaaaag   2040

tcagaccgtc catggaatga tcctggtgaa tggaaaatgc cagattcttt gaaatcacta   2100

tttaaattta aacgtcattc agcaacaacg aatagtgacc taccgatatc gaatggaagc   2160

agtaacggag aaacatatga aaagccgcta ctgaaagtcg tctgcctgga tttttcccaa   2220

gttgctcaag tggattcaac cgctgttcaa agcctggttg atctgagaaa agctgtgaat   2280

aggtatgcgg atagacaagt cgaattccat tttgccggaa ttatatctcc atggatcaaa   2340

agaagtcttt tgagtgttaa attcggaact acaaatgagg aatatagtga cgactctatt   2400

atcgctggcc attctagttt tcacgttgca aaagttttga aggatgatgt ggattatact   2460

gatgaagaca gccgtataag cacatcttac agtaactatg aaacattatg tgctgcaact   2520

gggacaaatt taccgttttt tcatatcgat atacccgatt tttctaaatg ggacgtttag   2580

a                                                                   2581
```

```
<210> SEQ ID NO 3
<211> LENGTH: 465
<212> TYPE: PRT
<213> ORGANISM: Saccharomyces cerevisiae

<400> SEQUENCE: 3

Met Pro Ile Lys Arg Leu Asp Thr Val Val Val Asn Thr Gly Ser Gln
1               5                   10                  15

Asn Asp Gln His Ser Ala Ser Val Pro Pro Val Tyr Leu Ser Thr Thr
            20                  25                  30

Phe Lys Val Asp Leu Asn Asn Glu Asp Ala Gln Asn Tyr Asp Tyr Ser
        35                  40                  45

Arg Ser Gly Asn Pro Thr Arg Ser Val Leu Gln His Gln Ile Gly Lys
    50                  55                  60

Leu Tyr Arg Val Pro Gln Glu Asn Val Leu Ala Val Ser Ser Gly Met
65                  70                  75                  80

Thr Ala Leu Asp Val Ile Leu Arg Gly Leu Val Leu Leu Asn Gly Thr
                85                  90                  95
```

-continued

```
Asp Asn His Thr Pro Thr Ile Ile Ala Gly Asp Asp Leu Tyr Gly Gly
            100                 105                 110

Thr Gln Arg Leu Leu Asn Phe Phe Lys Gln Gln Ser His Ala Val Ser
        115                 120                 125

Val His Val Asp Thr Ser Asp Phe Glu Lys Phe Lys Thr Val Phe Gln
    130                 135                 140

Ser Leu Asp Lys Val Asp Cys Val Leu Leu Glu Ser Pro Thr Asn Pro
145                 150                 155                 160

Leu Cys Lys Val Val Asp Ile Pro Arg Ile Leu Arg Phe Val Lys Cys
                165                 170                 175

Ile Ser Pro Asp Thr Thr Val Val Val Asp Asn Thr Met Met Ser Gly
            180                 185                 190

Leu Asn Cys Asn Pro Leu Gln Leu Asn Pro Gly Cys Asp Val Val Tyr
        195                 200                 205

Glu Ser Ala Thr Lys Tyr Leu Asn Gly His His Asp Leu Met Gly Gly
    210                 215                 220

Val Ile Ile Ser Lys Thr Pro Glu Ile Ala Ser Lys Leu Tyr Phe Val
225                 230                 235                 240

Ile Asn Ser Thr Gly Ala Gly Leu Ser Pro Met Asp Ser Trp Leu Leu
                245                 250                 255

Val Arg Gly Leu Lys Thr Leu Gly Val Arg Leu Tyr Gln Gln Gln Arg
            260                 265                 270

Asn Ala Met Ile Leu Ala His Trp Leu Glu Asn Ser Cys Gly Phe Lys
        275                 280                 285

Pro Thr Arg Thr Asn Lys Ala Thr Lys Thr Arg Phe Val Gly Leu Arg
    290                 295                 300

Ser Asn Pro Asp Phe Lys Leu His Lys Ser Phe Asn Asn Gly Pro Gly
305                 310                 315                 320

Ala Val Leu Ser Phe Glu Thr Gly Ser Phe Glu His Ser Lys Arg Leu
                325                 330                 335

Val Ser Ser Lys Lys Leu Ser Ile Trp Ala Val Thr Val Ser Phe Gly
            340                 345                 350

Cys Val Asn Ser Leu Leu Ser Met Pro Cys Lys Met Ser His Ala Ser
        355                 360                 365

Ile Asp Pro Glu Leu Arg Lys Glu Arg Asp Phe Pro Glu Asp Leu Val
    370                 375                 380

Arg Leu Cys Cys Gly Ile Glu Asn Ile Val Asp Leu Lys Lys Asp Leu
385                 390                 395                 400

Leu Ala Ala Met Val Asp Ala Asp Ile Ile Glu Val Arg Glu Asn Gly
                405                 410                 415

Lys Tyr Leu Phe Asn Lys Leu Asn Lys Asn Leu Ala Val Asn Thr Thr
            420                 425                 430

Ile Asp Asp Leu His Lys Pro Leu Ser Ile Tyr Glu Glu Phe Tyr Asn
        435                 440                 445

Gln Asp Leu Ile Arg Lys Asp Ser Glu Leu Asn Ile Lys Ser Ser Lys
    450                 455                 460

Leu
465
```

<210> SEQ ID NO 4
<211> LENGTH: 1399
<212> TYPE: DNA
<213> ORGANISM: Saccharomyces cerevisiae

<400> SEQUENCE: 4

```
atgccgatca agagattaga tacagttgtg gtaaataccg gctctcaaaa tgaccaacat      60
tcagcctccg tgccaccggt gtatttgtcg actaccttca aagtggactt gaataatgaa     120
gatgcacaga actacgatta ttccagatcg ggaaacccga ccagaagtgt ccttcaacac     180
cagattggta agctttatcg tgtcccacag gaaaacgtat tagctgtgag cagtggtatg     240
acggcgctag acgtcatcct gcgtgggctc gtcttactta acggcactga caaccatacg     300
ccaacaataa tagccggcga tgatctttat ggaggcaccc aaaggctgct gaattttttc     360
aagcaacaga gtcatgcagt ctctgttcat gtggacactt ccgattttga aaagttcaaa     420
accgttttcc agtctttaga taaagttgat tgtgttcttc tagagtctcc gaccaatccg     480
ctttgcaagg ttgtagatat ccctagaata ttacgttttg tgaaatgcat atctcccgac     540
actacagttg tcgttgataa tactatgatg agtggactca attgtaatcc tcttcaactg     600
aatccaggct gcgatgtcgt atacgaatct gctaccaagt acttgaatgg tcatcacgat     660
ttgatggggg gtgttattat cagcaaaaca ccagaaatag cctcgaagct ttactttgtc     720
attaattcta caggagctgg attatcccca atggattctt ggctacttgt gaggggccta     780
aaaactctag gagttagatt atatcaacag cagagaaatg ctatgatatt ggctcattgg     840
ctagaaaatt catgcggatt caaacctacc agaacaaaca aggctacgaa aactagattt     900
gttggattac gctccaaccc ggatttcaag ctgcataaat cgttcaataa tggcccaggt     960
gccgtgttat ccttcgaaac ggggtccttc gaacattcaa agagactggt cagttccaaa    1020
aaactgagta tatgggctgt gacggtatct ttcgggtgtg taaattcgct tctatctatg    1080
ccttgcaaaa tgtcccatgc ttccattgat cccgaattaa ggaaagagag agattttcct    1140
gaagatttgg ttcgtctttg ctgcggtatc gaaaatatag tagatttgaa gaaagattta    1200
ttagcggcga tggttgacgc tgatattata gaagtaagag aaaatggcaa atatcttttc    1260
aacaaattga ataagaacct agctgtgaac actaccatcg atgacctgca taagccttta    1320
agtatttacg aagaatttta caatcaagat ctcatcagaa aggactcaga attgaatatt    1380
aagagttcga aattgtaaa                                                 1399
```

<210> SEQ ID NO 5
<211> LENGTH: 1399
<212> TYPE: PRT
<213> ORGANISM: Saccharomyces cerevisiae

<400> SEQUENCE: 5

```
Ala Thr Gly Cys Cys Gly Ala Thr Cys Ala Ala Gly Ala Gly Ala Thr
  1               5                  10                  15
Thr Ala Gly Ala Thr Ala Cys Ala Gly Thr Thr Gly Thr Gly Gly Thr
                 20                  25                  30
Ala Ala Ala Thr Ala Cys Cys Gly Gly Cys Thr Cys Thr Cys Ala Ala
             35                  40                  45
Ala Ala Thr Gly Ala Cys Cys Ala Ala Cys Ala Thr Thr Cys Ala Gly
         50                  55                  60
Cys Cys Thr Cys Cys Gly Thr Gly Cys Cys Ala Cys Cys Gly Gly Thr
 65                  70                  75                  80
Gly Thr Ala Thr Thr Thr Gly Thr Cys Gly Ala Cys Thr Ala Cys Cys
                 85                  90                  95
Thr Thr Cys Ala Ala Ala Gly Thr Gly Gly Ala Cys Thr Thr Gly Ala
            100                 105                 110
```

```
Ala Thr Ala Ala Thr Gly Ala Ala Gly Ala Thr Gly Cys Ala Cys Ala
        115                 120                 125

Gly Ala Ala Cys Thr Ala Cys Gly Ala Thr Thr Ala Thr Thr Cys Cys
    130                 135                 140

Ala Gly Ala Thr Cys Gly Gly Gly Ala Ala Ala Cys Cys Cys Gly Ala
145                 150                 155                 160

Cys Cys Ala Gly Ala Ala Gly Thr Gly Thr Cys Cys Thr Thr Cys Ala
                165                 170                 175

Ala Cys Ala Cys Cys Ala Gly Ala Thr Thr Gly Gly Thr Ala Ala Gly
            180                 185                 190

Cys Thr Thr Thr Ala Thr Cys Gly Thr Gly Thr Cys Cys Cys Ala Cys
        195                 200                 205

Ala Gly Gly Ala Ala Ala Ala Cys Gly Thr Ala Thr Thr Ala Gly Cys
    210                 215                 220

Thr Gly Thr Gly Ala Gly Cys Ala Gly Thr Gly Gly Thr Ala Thr Gly
225                 230                 235                 240

Ala Cys Gly Gly Cys Gly Cys Thr Ala Gly Ala Cys Gly Thr Cys Ala
                245                 250                 255

Thr Cys Cys Thr Gly Cys Gly Thr Gly Gly Gly Cys Thr Cys Gly Thr
            260                 265                 270

Cys Thr Thr Ala Cys Thr Thr Ala Ala Cys Gly Gly Cys Ala Cys Thr
        275                 280                 285

Gly Ala Cys Ala Ala Cys Cys Ala Thr Ala Cys Gly Cys Cys Ala Ala
    290                 295                 300

Cys Ala Ala Thr Ala Ala Thr Ala Gly Cys Cys Gly Gly Cys Gly Ala
305                 310                 315                 320

Thr Gly Ala Thr Cys Thr Thr Thr Ala Thr Gly Gly Ala Gly Gly Cys
                325                 330                 335

Ala Cys Cys Cys Ala Ala Ala Gly Gly Cys Thr Gly Cys Thr Gly Ala
            340                 345                 350

Ala Thr Thr Thr Thr Thr Thr Cys Ala Ala Gly Cys Ala Ala Cys Ala
        355                 360                 365

Gly Ala Gly Thr Cys Ala Thr Gly Cys Ala Gly Thr Cys Thr Cys Thr
    370                 375                 380

Gly Thr Thr Cys Ala Thr Gly Thr Gly Gly Ala Cys Ala Cys Thr Thr
385                 390                 395                 400

Cys Cys Gly Ala Thr Thr Thr Thr Gly Ala Ala Ala Ala Gly Thr Thr
                405                 410                 415

Cys Ala Ala Ala Ala Cys Cys Gly Thr Thr Thr Thr Cys Cys Ala Gly
            420                 425                 430

Thr Cys Thr Thr Thr Ala Gly Ala Thr Ala Ala Ala Gly Thr Thr Gly
        435                 440                 445

Ala Thr Thr Gly Thr Gly Thr Thr Cys Thr Thr Cys Thr Ala Gly Ala
    450                 455                 460

Gly Thr Cys Thr Cys Cys Gly Ala Cys Cys Ala Ala Thr Cys Cys Gly
465                 470                 475                 480

Cys Thr Thr Thr Gly Cys Ala Ala Gly Gly Thr Thr Gly Thr Ala Gly
                485                 490                 495

Ala Thr Ala Thr Cys Cys Cys Thr Ala Gly Ala Ala Thr Ala Thr Thr
            500                 505                 510

Ala Cys Gly Thr Thr Thr Thr Gly Thr Gly Ala Ala Ala Thr Gly Cys
        515                 520                 525

Ala Thr Ala Thr Cys Thr Cys Cys Cys Gly Ala Cys Ala Cys Thr Ala
```

-continued

```
    530                 535                 540

Cys Ala Gly Thr Thr Gly Thr Cys Gly Thr Thr Gly Ala Thr Ala Ala
545                 550                 555                 560

Thr Ala Cys Thr Ala Thr Gly Ala Thr Gly Ala Gly Thr Gly Gly Ala
                565                 570                 575

Cys Thr Cys Ala Ala Thr Thr Gly Thr Ala Ala Thr Cys Cys Thr Cys
            580                 585                 590

Thr Thr Cys Ala Ala Cys Thr Gly Ala Ala Thr Cys Cys Ala Gly Gly
        595                 600                 605

Cys Thr Gly Cys Gly Ala Thr Gly Thr Cys Gly Thr Ala Thr Ala Cys
    610                 615                 620

Gly Ala Ala Thr Cys Thr Gly Cys Thr Ala Cys Cys Ala Ala Gly Thr
625                 630                 635                 640

Ala Cys Thr Thr Gly Ala Ala Thr Gly Gly Thr Cys Ala Thr Cys Ala
                645                 650                 655

Cys Gly Ala Thr Thr Thr Gly Ala Thr Gly Gly Gly Gly Gly Gly Thr
            660                 665                 670

Gly Thr Thr Ala Thr Thr Ala Thr Cys Ala Gly Cys Ala Ala Ala Ala
        675                 680                 685

Cys Ala Cys Cys Ala Gly Ala Ala Ala Thr Ala Gly Cys Cys Thr Cys
    690                 695                 700

Gly Ala Ala Gly Cys Thr Thr Thr Ala Cys Thr Thr Thr Gly Thr Cys
705                 710                 715                 720

Ala Thr Thr Ala Ala Thr Thr Cys Thr Ala Cys Ala Gly Gly Ala Gly
                725                 730                 735

Cys Thr Gly Gly Ala Thr Thr Ala Thr Cys Cys Cys Cys Ala Ala Thr
            740                 745                 750

Gly Gly Ala Thr Thr Cys Thr Thr Gly Gly Cys Thr Ala Cys Thr Thr
        755                 760                 765

Gly Thr Gly Ala Gly Gly Gly Gly Cys Cys Thr Ala Ala Ala Ala Ala
    770                 775                 780

Cys Thr Cys Thr Ala Gly Gly Ala Gly Thr Thr Ala Gly Ala Thr Thr
785                 790                 795                 800

Ala Thr Ala Thr Cys Ala Ala Cys Ala Gly Cys Ala Gly Ala Gly Ala
                805                 810                 815

Ala Ala Thr Gly Cys Thr Ala Thr Gly Ala Thr Ala Thr Thr Gly Gly
            820                 825                 830

Cys Thr Cys Ala Thr Thr Gly Gly Cys Thr Ala Gly Ala Ala Ala Ala
        835                 840                 845

Thr Thr Cys Ala Thr Gly Cys Gly Gly Ala Thr Thr Cys Ala Ala Ala
    850                 855                 860

Cys Cys Thr Ala Cys Cys Ala Gly Ala Ala Cys Ala Ala Ala Cys Ala
865                 870                 875                 880

Ala Gly Gly Cys Thr Ala Cys Gly Ala Ala Ala Ala Cys Thr Ala Gly
                885                 890                 895

Ala Thr Thr Thr Gly Thr Thr Gly Gly Ala Thr Thr Ala Cys Gly Cys
            900                 905                 910

Thr Cys Cys Ala Ala Cys Cys Cys Gly Gly Ala Thr Thr Thr Cys Ala
        915                 920                 925

Ala Gly Cys Thr Gly Cys Ala Thr Ala Ala Ala Thr Cys Gly Thr Thr
    930                 935                 940

Cys Ala Ala Thr Ala Ala Thr Gly Gly Cys Cys Cys Ala Gly Gly Thr
945                 950                 955                 960
```

-continued

```
Gly Cys Cys Gly Thr Gly Thr Thr Ala Thr Cys Cys Thr Thr Cys Gly
                965                 970                 975

Ala Ala Ala Cys Gly Gly Gly Gly Thr Cys Cys Thr Thr Cys Gly Ala
            980                 985                 990

Ala Cys Ala Thr Thr Cys Ala Ala Ala Gly Ala Gly Ala Cys Thr Gly
        995                1000                1005

Gly Thr Cys Ala Gly Thr Thr Cys Cys Ala Ala Ala Ala Ala Ala Cys
   1010                1015                1020

Thr Gly Ala Gly Thr Ala Thr Ala Thr Gly Gly Gly Cys Thr Gly Thr
1025                1030                1035                1040

Gly Ala Cys Gly Gly Thr Ala Thr Cys Thr Thr Thr Cys Gly Gly Gly
               1045                1050                1055

Thr Gly Thr Gly Thr Ala Ala Ala Thr Thr Cys Gly Cys Thr Thr Cys
           1060                1065                1070

Thr Ala Thr Cys Thr Ala Thr Gly Cys Cys Thr Thr Gly Cys Ala Ala
       1075                1080                1085

Ala Ala Thr Gly Thr Cys Cys Cys Ala Thr Gly Cys Thr Thr Cys Cys
   1090                1095                1100

Ala Thr Thr Gly Ala Thr Cys Cys Cys Gly Ala Ala Thr Thr Ala Ala
1105                1110                1115                1120

Gly Gly Ala Ala Ala Gly Ala Gly Ala Gly Ala Gly Ala Thr Thr Thr
               1125                1130                1135

Thr Cys Cys Thr Gly Ala Ala Gly Ala Thr Thr Thr Gly Gly Thr Thr
           1140                1145                1150

Cys Gly Thr Cys Thr Thr Thr Gly Cys Thr Gly Cys Gly Gly Thr Ala
       1155                1160                1165

Thr Cys Gly Ala Ala Ala Ala Thr Ala Thr Ala Gly Thr Ala Gly Ala
   1170                1175                1180

Thr Thr Thr Gly Ala Ala Gly Ala Ala Ala Gly Ala Thr Thr Thr Ala
1185                1190                1195                1200

Thr Thr Ala Gly Cys Gly Gly Cys Gly Ala Thr Gly Gly Thr Thr Gly
               1205                1210                1215

Ala Cys Gly Cys Thr Gly Ala Thr Ala Thr Thr Ala Thr Ala Gly Ala
           1220                1225                1230

Ala Gly Thr Ala Ala Gly Ala Gly Ala Ala Ala Ala Thr Gly Gly Cys
       1235                1240                1245

Ala Ala Ala Thr Ala Thr Cys Thr Thr Thr Thr Cys Ala Ala Cys Ala
   1250                1255                1260

Ala Ala Thr Thr Gly Ala Ala Thr Ala Ala Gly Ala Ala Cys Cys Thr
1265                1270                1275                1280

Ala Gly Cys Thr Gly Thr Gly Ala Ala Cys Ala Cys Thr Ala Cys Cys
               1285                1290                1295

Ala Thr Cys Gly Ala Thr Gly Ala Cys Cys Thr Gly Cys Ala Thr Ala
           1300                1305                1310

Ala Gly Cys Cys Thr Thr Thr Ala Ala Gly Thr Ala Thr Thr Thr Ala
       1315                1320                1325

Cys Gly Ala Ala Gly Ala Ala Thr Thr Thr Thr Ala Cys Ala Ala Thr
   1330                1335                1340

Cys Ala Ala Gly Ala Thr Cys Thr Cys Ala Thr Cys Ala Gly Ala Ala
1345                1350                1355                1360

Ala Gly Gly Ala Cys Thr Cys Ala Gly Ala Ala Thr Thr Gly Ala Ala
               1365                1370                1375
```

-continued

Thr Ala Thr Thr Ala Ala Gly Ala Gly Thr Thr Cys Gly Ala Ala Ala
1380 1385 1390

Thr Thr Gly Thr Ala Ala Ala
1395

<210> SEQ ID NO 6
<211> LENGTH: 1714
<212> TYPE: DNA
<213> ORGANISM: Saccharomyces cerevisiae

<400> SEQUENCE: 6
atgtcacaag acgctgctat tgcagagcaa actcctgtgg agcatctctc tgctgttgac 60
tcagcctccc actcggtttt atctacacca tcaaacaagg ctgaaagaga tgaaataaaa 120
gcttatggtg aaggtgaaga gcacgaacct gtcgttgaaa ttccaaagag accagcttct 180
gcctatgtca ctgtctctat tatgtgtatc atgatcgcct ttggtggttt cgttttcggt 240
tgggatactg gtaccatttc tggtttcatc aatcaaaccg atttcatcag aagatttggt 300
atgaagcata aagatggtac taattatttg tctaaggtta gaactggttt gattgtctcc 360
attttcaaca ttggttgtgc cattggtggt attattcttt ccaaattggg tgatatgtac 420
ggtcgtaagg tgggtttgat tgtcgttgtt gtcatctaca tcatcggtat tattattcaa 480
attgcatcta tcaacaaatg gtaccaatat ttcatcggta gaattatttc cggtttgggt 540
gttggtggta ttgccgtttt atctcctatg ttgatttctg aagtatcccc aaagcattta 600
aggggtactt tagtctcttg ctaccaattg atgattactg ccggtatttt cttgggttac 660
tgtaccaact tcggtactaa gaactactcc aactctgtgc aatggagagt tccattaggt 720
ttgtgttttg cctgggcttt gtttatgatt ggtggtatga catttgttcc agagtctcca 780
cgttatttgg ctgaagtcgg taagatcgaa gaagccaaac gttctattgc cgtttctaac 840
aaggttgctg ttgatgatcc atctgttttg gctgaaatcg aagctgtctt ggctggtgta 900
gaggcagaga aattagctgg taatgcatcc tggggtgaat tgtttagtag caagacaaag 960
gtccttcaac gtttgatcat gggtgctatg attcaatctc tacaacaatt gacaggtgat 1020
aactatttct tctactatgg tactactatt ttcaaggctg ttggtttgag tgactctttc 1080
gaaacctcta ttgtcttggg tattgttaac tttgcttcca cctttgttgg tatttacgtt 1140
gttgagagat atggtcgtcg tacttgtttg ctatggggtg ctgcatccat gactgcttgt 1200
atggttgtct atgcttccgt gggtgtcacc agattatggc caaatggtca agaccaacca 1260
tcttccaagg gtgctggtaa ctgtatgatt gtctttgcct gtttctatat tttctgtttt 1320
gctactacat gggctccaat tccttatgtc gttgtttctg aaactttccc attgagagtc 1380
aagtctaagg ctatgtctat tgctacagct gctaattggt tgtggggttt cttgattggt 1440
ttcttcactc catttattac tggtgctatt aacttctact acggttacgt tttcatgggc 1500
tgtttggtct tcatgttctt ctatgttttg ttagttgttc cagaaactaa gggtttgact 1560
ttggaagaag tcaacaccat gtgggaagaa ggtgttctac catggaagtc tgcctcatgg 1620
gttccaccat ccagaagagg tgccaactac gacgctgaag aaatgactca cgatgacaag 1680
ccattgtaca agagaatgtt cagcaccaaa taaa 1714

<210> SEQ ID NO 7
<211> LENGTH: 437
<212> TYPE: PRT
<213> ORGANISM: Saccharomyces cerevisiae

<400> SEQUENCE: 7

-continued

```
Met Ser Ile Thr Lys Val His Ala Arg Thr Val Tyr Asp Ser Arg Gly
1               5                   10                  15

Asn Pro Thr Val Glu Val Glu Ile Thr Thr Glu Asn Gly Leu Phe Arg
            20                  25                  30

Ala Ile Val Pro Ser Gly Ala Ser Thr Gly Ile His Glu Ala Val Glu
        35                  40                  45

Leu Arg Asp Gly Asn Lys Ser Glu Trp Met Gly Lys Gly Val Thr Lys
    50                  55                  60

Ala Val Ser Asn Val Asn Ser Ile Ile Gly Pro Ala Leu Ile Lys Ser
65                  70                  75                  80

Asp Leu Cys Val Thr Asn Gln Lys Gly Ile Asp Glu Leu Met Ile Ser
                85                  90                  95

Leu Asp Gly Thr Ser Asn Lys Ser Arg Leu Gly Ala Asn Ala Ile Leu
            100                 105                 110

Gly Val Ser Leu Cys Val Ala Arg Ala Ala Ala Ala Gln Lys Gly Ile
        115                 120                 125

Thr Leu Tyr Lys Tyr Ile Ala Glu Leu Ala Asp Ala Arg Gln Asp Pro
    130                 135                 140

Phe Val Ile Pro Val Pro Phe Phe Asn Val Leu Asn Gly Gly Ala His
145                 150                 155                 160

Ala Gly Gly Ser Leu Ala Met Gln Glu Phe Lys Ile Ala Pro Val Gly
                165                 170                 175

Ala Gln Ser Phe Ala Glu Ala Met Arg Met Gly Ser Glu Val Tyr His
            180                 185                 190

His Leu Lys Ile Leu Ala Lys Glu Gln Tyr Gly Pro Ser Ala Gly Asn
        195                 200                 205

Val Gly Asp Glu Gly Gly Val Ala Pro Asp Ile Asp Thr Ala Glu Asp
    210                 215                 220

Ala Leu Asp Met Ile Val Lys Ala Ile Asn Ile Cys Gly Tyr Glu Gly
225                 230                 235                 240

Arg Val Lys Val Gly Ile Asp Ser Ala Pro Ser Val Phe Tyr Lys Asp
                245                 250                 255

Gly Lys Tyr Asp Leu Asn Phe Lys Glu Pro Asn Ser Asp Pro Ser His
            260                 265                 270

Trp Leu Ser Pro Ala Gln Leu Ala Glu Tyr Tyr His Ser Leu Leu Lys
        275                 280                 285

Lys Tyr Pro Ile Ile Ser Leu Glu Asp Pro Tyr Ala Glu Asp Asp Trp
    290                 295                 300

Ser Ser Trp Ser Ala Phe Leu Lys Thr Val Asn Val Gln Ile Ile Ala
305                 310                 315                 320

Asp Asp Leu Thr Cys Thr Asn Lys Thr Arg Ile Ala Arg Ala Ile Glu
                325                 330                 335

Glu Lys Cys Ala Asn Thr Leu Leu Leu Lys Leu Asn Gln Ile Gly Thr
            340                 345                 350

Leu Thr Glu Ser Ile Glu Ala Ala Asn Gln Ala Phe Asp Ala Gly Trp
        355                 360                 365

Gly Val Met Ile Ser His Arg Ser Gly Glu Thr Glu Asp Pro Phe Ile
    370                 375                 380

Ala Asp Leu Val Val Gly Leu Arg Cys Gly Gln Ile Lys Ser Gly Ala
385                 390                 395                 400

Leu Ser Arg Ser Glu Arg Leu Ala Lys Tyr Asn Glu Leu Leu Arg Ile
                405                 410                 415
```

-continued

```
Glu Glu Glu Leu Gly Asp Asp Cys Ile Tyr Ala Gly His Arg Phe His
            420                 425                 430

Asp Gly Asn Lys Leu
        435
```

<210> SEQ ID NO 8
<211> LENGTH: 1315
<212> TYPE: DNA
<213> ORGANISM: Saccharomyces cerevisiae

<400> SEQUENCE: 8

```
atgtccatca cgaaggtaca tgctagaacg gtgtatgatt ctcgcggtaa tccgactgtt     60

gaggttgaaa ttacaacaga gaatggtctc ttcagagcga tcgtcccatc tggtgcctcc    120

accggcattc acgaagctgt tgaacttaga gacgggaaca agtccgaatg gatgggaaaa    180

ggggtgacca aggcagtcag taacgtcaat agtatcatag ggcctgcttt aatcaagtcc    240

gacttatgtg taaccaatca gaagggcata gacgagctca tgatatcgtt agacggaact    300

tctaacaagt caaggttggg cgccaatgct atccttggtg tttccttgtg cgttgctcga    360

gctgctgccg cacaaaaggg aattactctc tacaagtata tagccgagtt agcggatgct    420

agacaggacc cctttgttat tcctgttcct tttttcaatg ttttgaatgg tggagcccac    480

gccggtggct ctttagctat gcaagaattc aagatcgcgc cagtcggggc tcagagcttt    540

gcagaagcca tgaggatggg ttcggaggtt taccatcatt tgaagatatt ggcgaaggag    600

caatatggac cttccgctgg aaatgttggt gacgagggtg gagtcgcccc cgatatcgac    660

actgccgagg acgccttgga catgattgtg aaagccatta acatatgcgg ttacgagggt    720

agagtgaaag taggaatcga tagtgctcct tctgtttttt ataaggacgg gaaatacgac    780

ctaaatttca aggaaccgaa ctctgaccca tctcactggc tcagtccagc tcagttagca    840

gaatattacc attcattgct aaagaaatac ccaatcattt ccctggaaga cccctacgcc    900

gaagatgatt ggtcctcgtg gtctgccttc ctaaagactg tcaatgttca gattattgca    960

gatgacctga catgcaccaa caagaccagg atcgcccgtg ctatagagga gaaatgtgcg   1020

aatactctgt tgctgaaact caaccagatc ggtactctga ctgagtctat tgaagccgcc   1080

aatcaggctt tcgatgctgg atggggtgta atgatatcac atagatcagg tgaaaccgaa   1140

gatccgttta tcgctgattt ggtcgttggt ttaagatgtg gtcaaattaa atcgggcgct   1200

ttgtcgagat cagaaagact ggccaagtat aatgaacttt tgcgtatcga agaggaactg   1260

ggggacgatt gtatatatgc tggtcatagg tttcatgatg gaaacaaact ataaa        1315
```

<210> SEQ ID NO 9
<211> LENGTH: 109
<212> TYPE: PRT
<213> ORGANISM: Saccharomyces cerevisiae

<400> SEQUENCE: 9

```
Met Ser Ala Phe Val Thr Lys Ala Glu Glu Met Ile Lys Ser His Pro
  1               5                  10                  15

Tyr Phe Gln Leu Ser Ala Ser Trp Cys Pro Asp Cys Val Tyr Ala Asn
             20                  25                  30

Ser Ile Trp Asn Lys Leu Asn Val Gln Asp Lys Val Phe Val Phe Asp
         35                  40                  45

Ile Gly Ser Leu Pro Arg Asn Glu Gln Glu Lys Trp Arg Ile Ala Phe
     50                  55                  60

Gln Lys Val Val Gly Ser Arg Asn Leu Pro Thr Ile Val Val Asn Gly
```

```
 65                  70                  75                  80

Lys Phe Trp Gly Thr Glu Ser Gln Leu His Arg Phe Glu Ala Lys Gly
                 85                  90                  95

Thr Leu Glu Glu Glu Leu Thr Lys Ile Gly Leu Leu Pro
            100                 105


<210> SEQ ID NO 10
<211> LENGTH: 331
<212> TYPE: DNA
<213> ORGANISM: Saccharomyces cerevisiae

<400> SEQUENCE: 10

atgtctgcct ttgttactaa agctgaagag atgatcaaat ctcatccata tttccagtta      60

tccgccagct ggtgccccga ctgcgtctat gctaattcca tttggaataa gttgaatgta     120

caggacaaag ttttcgtttt tgatattggt tcacttccaa gaaacgaaca ggaaaaatgg     180

agaattgcgt tccaaaaagt tgttggtagc agaaacttac caacgatagt tgtcaatggt     240

aaattctggg gtactgagag tcaattgcat agatttgaag caaaaggcac tcttgaggag     300

gaattgacta aaatcgggct tctgccttga a                                   331


<210> SEQ ID NO 11
<211> LENGTH: 160
<212> TYPE: PRT
<213> ORGANISM: Saccharomyces cerevisiae

<400> SEQUENCE: 11

Met Ser Ser Leu Ile Ser Lys Thr Ile Lys Lys Tyr Leu Asn Asp Arg
  1               5                  10                  15

Ile Val Asp Cys Lys Val Gly Tyr Ala Asn Gly Glu Glu Ser Lys Lys
            20                  25                  30

Asp Ser Pro Ser Ser Val Ser Tyr Lys Arg Val Cys Gly Gly Asp Thr
        35                  40                  45

Asp Phe Ala Glu Val Leu Gln Val Ser Tyr Asn Pro Lys Val Ile Thr
    50                  55                  60

Leu Arg Glu Leu Thr Asp Phe Phe Phe Arg Ile His Asp Pro Thr Thr
 65                  70                  75                  80

Ser Asn Ser Gln Gly Pro Asp Lys Gly Thr Gln Tyr Arg Ser Gly Leu
                 85                  90                  95

Phe Ala His Ser Asp Ala Asp Leu Lys Glu Leu Ala Lys Ile Lys Glu
            100                 105                 110

Glu Trp Gln Pro Lys Trp Gly Asn Lys Ile Ala Thr Val Ile Glu Pro
        115                 120                 125

Ile Lys Asn Phe Tyr Asp Ala Glu Glu Tyr His Gln Leu Tyr Leu Asp
    130                 135                 140

Lys Asn Pro Gln Gly Tyr Ala Cys Pro Thr His Tyr Leu Arg Glu Met
145                 150                 155                 160


<210> SEQ ID NO 12
<211> LENGTH: 484
<212> TYPE: DNA
<213> ORGANISM: Saccharomyces cerevisiae

<400> SEQUENCE: 12

atgtcgtcgc ttatttcaaa aaccattaag aagtatttga atgaccgtat agtggattgt      60

aaagtaggtt acgctaatgg agaagagtct aaaaaggata gcccctctag tgtctcttat     120

aagagagttt gtggtggtga cacagatttt gcggaggttt tacaagtatc ctataatccc     180
```

```
aaagtgataa ctttgagaga attaactgat ttcttttta gaatccatga tcctactaca    240

tctaattcac aaggacctga taaaggtaca cagtatcgca gtggattgtt cgctcattca    300

gatgctgatt taaaagaatt agccaaaata aaggaagaat ggcaaccaaa atggggtaat    360

aagattgcca cagttattga accaatcaag aacttttacg atgctgaaga ataccaccag    420

ttatatttag ataagaatcc acagggatat gcatgcccta ctcattatct gagagaaatg    480

taga                                                                484


<210> SEQ ID NO 13
<211> LENGTH: 501
<212> TYPE: PRT
<213> ORGANISM: Saccharomyces cerevisiae

<400> SEQUENCE: 13

Met Thr Asp Val Leu Arg Ser Leu Val Arg Lys Ile Ser Phe Asn Asn
  1               5                  10                  15

Ser Asp Asn Leu Gln Leu Lys His Lys Thr Ser Ile Gln Ser Asn Thr
             20                  25                  30

Ala Leu Glu Lys Lys Lys Arg Lys Pro Asp Thr Ile Lys Lys Val Ser
         35                  40                  45

Asp Val Gln Val His His Thr Val Pro Asn Phe Asn Asn Ser Ser Glu
     50                  55                  60

Tyr Ile Asn Asp Ile Glu Asn Leu Ile Ile Ser Lys Leu Ile Asp Gly
 65                  70                  75                  80

Gly Lys Glu Gly Ile Ala Val Asp His Ile Glu His Ala Asn Ile Ser
                 85                  90                  95

Asp Ser Lys Thr Asp Gly Lys Val Ala Asn Lys His Glu Asn Ile Ser
            100                 105                 110

Ser Lys Leu Ser Lys Glu Lys Val Glu Lys Met Ile Asn Phe Asp Tyr
        115                 120                 125

Arg Tyr Ile Lys Thr Lys Glu Arg Thr Ile His Lys Arg Val Tyr Lys
    130                 135                 140

His Asp Arg Lys Thr Asp Val Asp Arg Lys Asn His Gly Gly Thr Ile
145                 150                 155                 160

Asp Ile Ser Tyr Pro Thr Thr Glu Val Val Gly His Gly Ser Phe Gly
                165                 170                 175

Val Val Val Thr Thr Val Ile Ile Glu Thr Asn Gln Lys Val Ala Ile
            180                 185                 190

Lys Lys Val Leu Gln Asp Arg Arg Tyr Lys Asn Arg Glu Leu Glu Thr
        195                 200                 205

Met Lys Met Leu Cys His Pro Asn Thr Val Gly Leu Gln Tyr Tyr Phe
    210                 215                 220

Tyr Glu Lys Asp Glu Glu Asp Glu Val Tyr Leu Asn Leu Val Leu Asp
225                 230                 235                 240

Tyr Met Pro Gln Ser Leu Tyr Gln Arg Leu Arg His Phe Val Asn Leu
                245                 250                 255

Lys Met Gln Met Pro Arg Val Glu Ile Lys Phe Tyr Ala Tyr Gln Leu
            260                 265                 270

Phe Lys Ala Leu Asn Tyr Leu His Asn Val Pro Arg Ile Cys His Arg
        275                 280                 285

Asp Ile Lys Pro Gln Asn Leu Leu Val Asp Pro Thr Thr Phe Ser Phe
    290                 295                 300

Lys Ile Cys Asp Phe Gly Ser Ala Lys Cys Leu Lys Pro Asp Gln Pro
```

-continued

```
305                 310                 315                 320

Asn Val Ser Tyr Ile Cys Ser Arg Tyr Tyr Arg Ala Pro Glu Leu Met
                325                 330                 335

Phe Gly Ala Thr Asn Tyr Ser Asn Gln Val Asp Val Trp Ser Ser Ala
            340                 345                 350

Cys Val Ile Ala Glu Leu Leu Leu Gly Lys Pro Leu Phe Ser Gly Glu
        355                 360                 365

Ser Gly Ile Asp Gln Leu Val Glu Ile Ile Lys Ile Met Gly Ile Pro
    370                 375                 380

Thr Lys Asp Glu Ile Ser Gly Met Asn Pro Asn Tyr Glu Asp His Val
385                 390                 395                 400

Phe Pro Asn Ile Lys Pro Ile Thr Leu Ala Glu Ile Phe Lys Ala Glu
                405                 410                 415

Asp Pro Asp Thr Leu Asp Leu Leu Thr Lys Thr Leu Lys Tyr His Pro
            420                 425                 430

Cys Glu Arg Leu Val Pro Leu Gln Cys Leu Leu Ser Ser Tyr Phe Asp
        435                 440                 445

Glu Thr Lys Arg Cys Asp Thr Asp Thr Tyr Val Lys Ala Gln Asn Leu
    450                 455                 460

Arg Ile Phe Asp Phe Asp Val Glu Thr Glu Leu Gly His Val Pro Leu
465                 470                 475                 480

Val Glu Arg Pro Ala Ile Glu Glu Arg Leu Lys His Phe Val Ser Ala
                485                 490                 495

Pro Ser Ser Ser Leu
            500


<210> SEQ ID NO 14
<211> LENGTH: 1507
<212> TYPE: DNA
<213> ORGANISM: Saccharomyces cerevisiae

<400> SEQUENCE: 14

atgaccgatg tgttgagaag cctagtgcga aagatttcct tcaataactc agataacctt     60

cagctaaaac acaagacatc tatacagagt aatactgccc tagaaaagaa gaagagaaag    120

cctgatacaa tcaaaaaggt aagcgacgtt caagttcacc atactgtacc taatttcaat    180

aacagttcag agtacatcaa cgacatagag aatcttataa tatctaaact gatagacggg    240

ggaaaggagg gtattgcagt tgatcacatt gaacacgcca atatctcgga cagtaaaaca    300

gatggaaaag ttgccaataa gcacgaaaat attagtagca agcttagtaa agagaaggtt    360

gagaaaatga ttaattttga ttataggtat attaaaacca aggaaaggac tattcataaa    420

cgggtttata aacatgaccg caaaactgat gtcgaccgaa aaaatcatgg aggaactatc    480

gacatcagtt atcctacgac agaagtggtt ggccatggtt catttggtgt tgtagtcacg    540

actgtaataa ttgagaccaa tcaaaaagtt gccataaaga aagtactaca agatagaaga    600

tataaaaata gggagctcga aactatgaag atgttgtgcc atccaaatac tgtgggtcta    660

cagtactact tttacgaaaa ggacgaagaa gatgaagtat acctcaatct ggttttggac    720

tacatgcctc agtcgttata ccaaaggctt cgtcattttg ttaatttgaa aatgcagatg    780

ccgcgtgttg aaattaaatt ctatgcatac caactattca aagctttaaa ctatttgcat    840

aacgttcctc gaatctgtca cagagatata aaaccgcaaa acctactggt ggatccgaca    900

actttttctt tcaagatttg cgattttggc agtgccaaat gcttgaaacc ggatcagcct    960

aatgtgtctt acatctgttc aaggtactat agggctcccg aactcatgtt tggtgccact   1020
```

-continued

```
aattactcaa accaggtcga cgtgtggtca agcgcttgtg tcattgctga gttgcttttg   1080

ggcaagccct tgttctctgg tgaaagcggt atagatcagt tggtggaaat tattaagata   1140

atgggcatac ccacaaagga tgaaatttca ggaatgaacc caaattatga agaccatgtt   1200

ttccccaata tcaagcccat tactttggct gaaatattca aagccgaaga tcccgatact   1260

cttgacttgt taacaaaaac tctgaagtat cacccttgcg aaagattggt acctctacaa   1320

tgtctattat caagctattt tgacgaaacc aaacgttgtg ataccgacac ttacgtaaaa   1380

gcacaaaacc tgcgtatatt tgacttcgac gtggaaactg agttgggcca tgttccactt   1440

gtggaacggc ccgccattga agaacggttg aaacattttg tttctgcacc ttcatcgtct   1500

ttgtgaa                                                             1507
```

<210> SEQ ID NO 15
<211> LENGTH: 168
<212> TYPE: PRT
<213> ORGANISM: Saccharomyces cerevisiae

<400> SEQUENCE: 15

```
Met Ser Asn Leu Leu Asn Lys Phe Ala Asp Lys Leu His Gly Asn Asp
  1               5                  10                  15

His Asp Glu Arg Tyr Glu Asp Asp Asn Asp Asp Gln Thr Arg Gln Gln
             20                  25                  30

Arg His Glu Lys His Gln Gln Arg Glu Phe Arg Asn Gln Gly Ser Lys
         35                  40                  45

Ala Asp Pro Tyr Gly Glu Glu Asn Gln Gly Asn Phe Pro Gln Arg Gln
     50                  55                  60

Gln Pro Gln Ser Asn Leu Gly Gly Asn Thr Gln Phe Gly Gly Asn Asp
 65                  70                  75                  80

Phe Gln Gln Gln Thr Thr Asp Tyr Thr Ala Gly Thr Gly Gly Gly Thr
                 85                  90                  95

Tyr Thr Gln Thr Tyr Arg Glu Thr Asn Thr Gln Gly Gln Leu Asp Asp
            100                 105                 110

Asp Glu Asp Asp Asp Phe Leu Thr Ser Gly Gln Gln Gln Lys Gln Gly
        115                 120                 125

Arg Thr Arg Gly Ala Gln Ser Asn Arg Tyr Gln Ser Ser Asn Ile Gly
    130                 135                 140

Ser Gly Arg Arg Asp Leu Ser Gly Ser Gly Asn Asp Glu Tyr Asp Asp
145                 150                 155                 160

Asp Ser Gly Asn Gln Gly Val Trp
                165
```

<210> SEQ ID NO 16
<211> LENGTH: 508
<212> TYPE: DNA
<213> ORGANISM: Saccharomyces cerevisiae

<400> SEQUENCE: 16

```
atgtccaatc tattaaacaa gtttgctgat aagttgcacg gcaacgatca tgatgaacgt     60

tacgaagacg acaatgacga ccagactaga caacagcgtc atgaaaaaca tcaacagagg    120

gaattcagga atcaaggatc caaggccgat ccctacggcg aagaaaacca agggaatttc    180

cctcaacgcc agcagccaca gtctaatcta ggcggtaaca cgcagtttgg cggtaacgac    240

ttccagcaac aaactactga ctacactgcc ggcactggtg gtggcactta tacccaaact    300

taccgcgaaa ctaacactca aggtcagttg gacgacgatg aagacgatga cttcttgact    360
```

```
tcgggccaac agcaaaaaca aggtcgtaca agaggtgctc aaagtaaccg ctaccaatcc    420

tctaatatcg gcagcggtag acgcgatctg tctgggtcag gaaacgatga atatgatgat    480

gatagtggga accaaggcgt ctggtaga                                        508


<210> SEQ ID NO 17
<211> LENGTH: 325
<212> TYPE: PRT
<213> ORGANISM: Saccharomyces cerevisiae

<400> SEQUENCE: 17

Met Ser Glu Ala Phe Gly Pro Ala Pro Glu Pro Pro Thr Glu Leu Gly
  1               5                  10                  15

Arg Leu Arg Val Leu Ser Lys Thr Ala Gly Ile Arg Val Ser Pro Leu
             20                  25                  30

Ile Leu Gly Gly Met Ser Ile Gly Asp Ala Trp Ser Gly Phe Met Gly
         35                  40                  45

Ser Met Asp Lys Glu Gln Ala Phe Glu Leu Leu Asp Ala Phe Tyr Gln
     50                  55                  60

Ala Gly Gly Asn Phe Ile Asp Thr Ala Asn Asn Tyr Tyr Leu His Val
 65                  70                  75                  80

Ser Val Arg Asp Ser Leu Arg Lys Leu Gln Thr Asp Trp Ile Asp Ile
                 85                  90                  95

Leu Tyr Val His Trp Trp Asp Tyr Met Ser Ser Ile Glu Glu Val Met
            100                 105                 110

Asp Ser Leu His Ile Leu Val Gln Gln Gly Lys Val Leu Tyr Leu Gly
        115                 120                 125

Val Ser Asp Thr Pro Ala Trp Val Val Ser Ala Ala Asn Tyr Tyr Ala
    130                 135                 140

Thr Ser His Gly Lys Thr Pro Phe Ser Ile Tyr Gln Gly Lys Trp Asn
145                 150                 155                 160

Val Leu Asn Arg Asp Phe Glu Arg Asp Ile Ile Pro Met Ala Arg His
                165                 170                 175

Phe Gly Met Ala Leu Ala Pro Trp Asp Val Met Gly Gly Gly Arg Phe
            180                 185                 190

Gln Ser Lys Lys Ala Val Glu Glu Arg Lys Lys Lys Gly Glu Gly Leu
        195                 200                 205

Arg Thr Phe Phe Gly Thr Ser Glu Gln Thr Asp Met Glu Val Lys Ile
    210                 215                 220

Ser Glu Ala Leu Leu Lys Val Ala Glu Glu His Gly Thr Glu Ser Val
225                 230                 235                 240

Thr Ala Ile Ala Ile Ala Tyr Val Arg Ser Lys Ala Lys His Val Phe
                245                 250                 255

Pro Leu Val Gly Gly Arg Lys Ile Glu His Leu Lys Gln Asn Ile Glu
            260                 265                 270

Ala Leu Ser Ile Lys Leu Thr Pro Glu Gln Ile Lys Tyr Leu Glu Ser
        275                 280                 285

Ile Val Pro Phe Asp Val Gly Phe Pro Thr Asn Phe Ile Gly Asp Asp
    290                 295                 300

Pro Ala Val Thr Lys Lys Pro Ser Phe Leu Thr Glu Met Ser Ala Lys
305                 310                 315                 320

Ile Ser Phe Glu Asp
                325
```

<210> SEQ ID NO 18
<211> LENGTH: 979
<212> TYPE: DNA
<213> ORGANISM: Saccharomyces cerevisiae

<400> SEQUENCE: 18
atgtctgagg cttttggacc tgcacctgaa ccacctaccg agttaggacg tcttagggtc 60
ctatctaaaa cagctggtat aagagtttct ccactaatcc tgggaggtat gtctattggt 120
gacgcctggt ctggattcat gggatcaatg gacaaagaac aagcttttga gctacttgat 180
gctttttacc aagcaggcgg aaatttcatt gatactgcaa ataattatta tttgcatgta 240
agtgtgagag attcccttcg taagttgcaa actgattgga ttgatattct ttacgttcac 300
tggtgggatt atatgagctc cattgaggaa gttatggata gtttgcacat tcttgtgcag 360
cagggcaaag tactctatct aggtgtgtct gatactcctg cctgggttgt ttctgcagca 420
aattactacg ccacatctca tggtaaaact ccctttagta tctatcaagg taaatggaat 480
gtattgaaca gggactttga acgtgatatc attccaatgg ctaggcattt tggtatggct 540
cttgctccat gggatgttat gggaggcggg agatttcaga gtaaaaaggc agtggaagag 600
cggaagaaga aaggagaagg cttgcgtacc ttttttggta cttcggaaca gacggatatg 660
gaggttaaaa tcagcgaagc attgttaaaa gttgcggaag aacatggcac tgagtctgtc 720
actgctattg ccatagctta tgttcggtct aaagcgaaac atgttttccc attagtggga 780
ggaagaaaga tcgaacatct caaacagaac attgaggctt tgagcattaa attaacacca 840
gaacaaataa agtacttaga aagtattgtt ccttttgatg tcggatttcc cactaatttt 900
attggagatg acccagctgt taccaagaaa ccttcatttc tcaccgaaat gtctgccaag 960
attagcttcg aagattaga 979

<210> SEQ ID NO 19
<211> LENGTH: 333
<212> TYPE: PRT
<213> ORGANISM: Lactobacillus delbrueckii subsp. bulgaicus

<400> SEQUENCE: 19

Met Thr Lys Ile Phe Ala Tyr Ala Ile Arg Glu Asp Glu Lys Pro Phe
1 5 10 15

Leu Lys Glu Trp Glu Asp Ala His Lys Asp Val Glu Val Glu Tyr Thr
20 25 30

Asp Lys Leu Leu Thr Pro Glu Thr Ala Ala Leu Ala Lys Gly Ala Asp
35 40 45

Gly Val Val Val Tyr Gln Gln Leu Asp Tyr Thr Ala Glu Thr Leu Gln
50 55 60

Ala Leu Ala Asp Asn Gly Ile Thr Lys Met Ser Leu Arg Asn Val Gly
65 70 75 80

Val Asp Asn Ile Asp Met Ala Lys Ala Lys Glu Leu Gly Phe Gln Ile
85 90 95

Thr Asn Val Pro Val Tyr Ser Pro Asn Ala Ile Ala Glu His Ala Ala
100 105 110

Ile Gln Ala Ala Arg Ile Leu Arg Gln Ala Lys Ala Met Asp Glu Lys
115 120 125

Val Ala Arg His Asp Leu Arg Trp Ala Pro Thr Ile Gly Arg Glu Val
130 135 140

Arg Asp Gln Val Val Gly Val Val Gly Thr Gly His Ile Gly Gln Val
145 150 155 160

```
Phe Met Gln Ile Met Glu Gly Phe Gly Ala Lys Val Ile Ala Tyr Asp
                165                 170                 175

Ile Phe Arg Asn Pro Glu Leu Glu Lys Lys Gly Tyr Tyr Val Asp Ser
            180                 185                 190

Leu Asp Asp Leu Tyr Lys Gln Ala Asp Val Ile Ser Leu His Val Pro
        195                 200                 205

Asp Val Pro Ala Asn Val His Met Ile Asn Asp Lys Ser Ile Ala Lys
    210                 215                 220

Met Lys Gln Asp Val Val Ile Val Asn Val Ser Arg Gly Pro Leu Val
225                 230                 235                 240

Asp Thr Asp Ala Val Ile Arg Gly Leu Asp Ser Gly Lys Val Phe Gly
                245                 250                 255

Tyr Ala Met Asp Val Tyr Glu Gly Glu Val Gly Val Phe Asn Glu Asp
            260                 265                 270

Trp Glu Gly Lys Glu Phe Pro Asp Ala Arg Leu Ala Asp Leu Ile Ala
        275                 280                 285

Arg Pro Asn Val Leu Val Thr Pro His Thr Ala Phe Tyr Thr Thr His
    290                 295                 300

Ala Val Arg Asn Met Val Ile Lys Ala Phe Asp Asn Asn Leu Glu Leu
305                 310                 315                 320

Ile Glu Gly Lys Glu Ala Glu Thr Pro Val Lys Val Gly
                325                 330


<210> SEQ ID NO 20
<211> LENGTH: 1002
<212> TYPE: DNA
<213> ORGANISM: Lactobacillus delbrueckii subsp. bulgaicus

<400> SEQUENCE: 20

atgactaaaa tcttcgctta cgctataaga gaggacgaaa agccattttt gaaagagtgg      60

gaggatgcgc ataaagatgt tgaagttgag tacacggata aacttttaac tcctgaaact     120

gctgcattgg caaagggtgc agacggcgta gtagtatatc aacagcttga ttatacagct     180

gaaaccctcc aagctctcgc tgataatggg attacaaaaa tgtctttgcg taatgtaggt     240

gttgacaaca tagacatggc caaagcaaag gaactaggct ttcaaatcac aaatgtgcct     300

gtgtactcac caaatgctat cgctgaacac gctgccatac aagccgctag aatcttaaga     360

caggcgaagg ctatggatga aaaggttgca agacatgatc taagatgggc tcctactatc     420

ggtagggaag taagagatca agttgtcggt gtggtgggaa caggacatat tggccaagtt     480

ttcatgcaga ttatggaagg attcggggca aaagtcattg cctacgacat ttttcgaaac     540

cctgagctgg agaaaaaggg ttactacgtt gattctctgg atgacctata caaacaagca     600

gatgttattt ctcttcatgt gccagatgtc ccagcaaatg tccacatgat caacgacaaa     660

tcaattgcca agatgaaaca agatgtcgta atcgttaatg tgagtagagg gcctttggtt     720

gacaccgacg ctgttataag gggtttggat tccggtaaag tatttggata tgcgatggat     780

gtttacgaag gtgaagtcgg tgtctttaac gaagattggg aaggcaaaga gttcccagac     840

gcaagattag ccgatttgat cgcaagacca aatgttttag taacaccaca cactgccttc     900

tatacaacac atgccgtgag aaacatggtt attaaggcat ttgataataa cttagaattg     960

atcgaaggca aggaagctga aactccagtt aaggtcggtt aa                       1002


<210> SEQ ID NO 21
<211> LENGTH: 332
<212> TYPE: PRT
```

-continued

<213> ORGANISM: Bos Taurus

<400> SEQUENCE: 21

```
Met Ala Thr Leu Lys Asp Gln Leu Ile Gln Asn Leu Leu Lys Glu Glu
  1               5                  10                  15

His Val Pro Gln Asn Lys Ile Thr Ile Val Gly Val Gly Ala Val Gly
             20                  25                  30

Met Ala Cys Ala Ile Ser Ile Leu Met Lys Asp Leu Ala Asp Glu Val
         35                  40                  45

Ala Leu Val Asp Val Met Glu Asp Lys Leu Lys Gly Glu Met Met Asp
     50                  55                  60

Leu Gln His Gly Ser Leu Phe Leu Arg Thr Pro Lys Ile Val Ser Gly
 65                  70                  75                  80

Lys Asp Tyr Asn Val Thr Ala Asn Ser Arg Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Ile Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu Gln Trp Lys Ala Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr His Glu Glu Glu Ala Cys Leu Lys Lys Ser Ala
305                 310                 315                 320

Asp Thr Leu Trp Gly Ile Gln Lys Glu Leu Gln Phe
                325                 330
```

<210> SEQ ID NO 22
<211> LENGTH: 332
<212> TYPE: PRT
<213> ORGANISM: Pelodiscus sinensis japonicus

<400> SEQUENCE: 22

```
Met Ser Val Lys Glu Leu Leu Ile Gln Asn Val His Lys Glu Glu His
  1               5                  10                  15

Ser His Ala His Asn Lys Ile Thr Val Val Gly Val Gly Ala Val Gly
```

-continued

```
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Arg Gly Glu Met Leu Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala His Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
    130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
    210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
            260                 265                 270

Ile Ser Thr Met Val Lys Gly Met Tyr Gly Val Ser Ser Asp Val Phe
        275                 280                 285

Leu Ser Val Pro Cys Val Leu Gly Tyr Ala Gly Ile Thr Asp Val Val
    290                 295                 300

Lys Met Thr Leu Lys Ser Glu Glu Glu Glu Lys Leu Arg Lys Ser Ala
305                 310                 315                 320

Asp Thr Leu Trp Gly Ile Gln Lys Glu Leu Gln Phe
                325                 330


<210> SEQ ID NO 23
<211> LENGTH: 332
<212> TYPE: PRT
<213> ORGANISM: Ornithorhynchus anatinus

<400> SEQUENCE: 23

Met Ala Gly Val Lys Glu Gln Leu Ile Gln Asn Leu Leu Lys Glu Glu
  1               5                  10                  15

Tyr Ala Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60
```

-continued

```
Leu Gln His Gly Ser Leu Phe Leu Arg Thr Pro Lys Ile Val Ser Gly
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Ile His Ser Thr Ser Cys His Gly Trp Val Ile Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Asp Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
            260                 265                 270

Ile Ser Thr Met Ile Lys Gly Leu Tyr Gly Ile Lys Asp Glu Val Phe
        275                 280                 285

Leu Ser Val Pro Cys Val Leu Gly Gln Asn Gly Ile Ser Asp Val Val
    290                 295                 300

Lys Ile Thr Leu Lys Ser Glu Glu Glu Ala His Leu Lys Lys Ser Ala
305                 310                 315                 320

Asp Thr Leu Trp Gly Ile Gln Lys Glu Leu Gln Phe
                325                 330


<210> SEQ ID NO 24
<211> LENGTH: 332
<212> TYPE: PRT
<213> ORGANISM: Tursiops truncatus

<400> SEQUENCE: 24

Met Ala Thr Val Lys Asp Gln Leu Ile Gln Asn Leu Leu Lys Glu Glu
  1               5                  10                  15

His Val Pro Gln Asn Lys Ile Thr Val Val Gly Val Gly Ala Val Gly
             20                  25                  30

Met Ala Cys Ala Ile Ser Ile Leu Met Lys Asp Leu Ala Asp Glu Leu
         35                  40                  45

Ala Leu Val Asp Val Ile Glu Asp Lys Leu Lys Gly Glu Met Met Asp
     50                  55                  60

Leu Gln His Gly Ser Leu Phe Leu Arg Thr Pro Lys Ile Val Ser Gly
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110
```

-continued

```
Asn Val Asn Ile Phe Lys Phe Ile Val Pro Asn Ile Val Lys Tyr Ser
        115                 120                 125

Pro His Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu His Trp Lys Ala Ile His Lys Gln Val Val Asp Ser Ala Tyr Glu
225                 230                 235                 240

Val Ile Lys Leu Lys Gly Tyr Thr Ser Trp Ala Val Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
                325                 330


<210> SEQ ID NO 25
<211> LENGTH: 332
<212> TYPE: PRT
<213> ORGANISM: Artificial Sequence
<220> FEATURE:
<223> OTHER INFORMATION: Rattus norvegicus

<400> SEQUENCE: 25

Met Ala Ala Leu Lys Asp Gln Leu Ile Val Asn Leu Leu Lys Glu Glu
  1               5                  10                  15

Gln Val Pro Gln Asn Lys Ile Thr Val Val Gly Val Gly Ala Val Gly
             20                  25                  30

Met Ala Cys Ala Ile Ser Ile Leu Met Lys Asp Leu Ala Asp Glu Leu
         35                  40                  45

Ala Leu Val Asp Val Ile Glu Asp Lys Leu Lys Gly Glu Met Met Asp
     50                  55                  60

Leu Gln His Gly Ser Leu Phe Leu Lys Thr Pro Lys Ile Val Ser Ser
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Gln Cys Lys Leu Leu Ile Val Ser Asn Pro Val Asp Ile Leu Thr
    130                 135                 140
```

-continued

```
Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Val Asn Val Ala Gly
        195                 200                 205

Val Ser Leu Lys Ser Leu Asn Pro Gln Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Asp Glu Glu Ala Arg Leu Lys Lys Ser Ala
305                 310                 315                 320

Asp Thr Leu Trp Gly Ile Gln Lys Glu Leu Gln Phe
                325                 330


<210> SEQ ID NO 26
<211> LENGTH: 999
<212> TYPE: DNA
<213> ORGANISM: Bos Taurus

<400> SEQUENCE: 26

atggcaacat taaaagatca actaatccag aatttgttga aagaggagca tgttccacaa     60

aacaaaatca caatcgtcgg cgtaggtgca gtaggtatgg cttgtgccat atccatcttg    120

atgaaagact tagctgatga ggtcgcgctg gttgatgtaa tggaggacaa acttaaagga    180

gaaatgatgg atcttcaaca tggttcactc tttttgagaa ctcctaaaat tgtatccggg    240

aaagattata acgttaccgc caattctaga cttgttataa tcacggctgg tgcaagacaa    300

caggaaggcg aatcaagact taacttagtt cagagaaacg taaacatttt caagtttatc    360

atcccaaata ttgtaaaata ctccccaaat tgcaagttgc tggttgtttc aaatcctgtt    420

gacatattga cttacgttgc ttggaagatt tcaggtttcc caaagaatag agtaatcgga    480

tctggttgca atctcgattc tgctcgtttt aggtatctga tgggtgaaag attaggggtt    540

catccattga gttgtcacgg atggattcta ggtgaacatg gagatagttc tgtgcctgtt    600

tggtcaggtg tcaacgtagc aggtgtctct ttgaaaaatc tacacccaga actaggaaca    660

gatgccgaca aggaacaatg gaaggccgtc cacaaacaag tggtggattc tgcctacgaa    720

gtcatcaaat tgaagggcta cacatcttgg gcaattggct tatccgtcgc tgatctggct    780

gaatcaataa tgaaaaacct ccgtagagtg catcctataa gtactatgat taagggttta    840

tacgggatca aggaagatgt ttttctatct gtgccatgta ttttgggcca aaatggaatt    900

tctgacgttg ttaaagtgac acttactcat gaagaggaag cgtgtttgaa aaagagcgca    960

gacaccttat ggggcatcca aaaggaatta caattctaa                           999
```

<210> SEQ ID NO 27
<211> LENGTH: 563
<212> TYPE: PRT
<213> ORGANISM: Saccharomyces cerevisiae

<400> SEQUENCE: 27

```
Met Ser Glu Ile Thr Leu Gly Lys Tyr Leu Phe Glu Arg Leu Lys Gln
  1               5                  10                  15

Val Asn Val Asn Thr Val Phe Gly Leu Pro Gly Asp Phe Asn Leu Ser
             20                  25                  30

Leu Leu Asp Lys Ile Tyr Glu Val Glu Gly Met Arg Trp Ala Gly Asn
         35                  40                  45

Ala Asn Glu Leu Asn Ala Ala Tyr Ala Ala Asp Gly Tyr Ala Arg Ile
     50                  55                  60

Lys Gly Met Ser Cys Ile Ile Thr Thr Phe Gly Val Gly Glu Leu Ser
 65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
    370                 375                 380
```

-continued

```
Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
    530                 535                 540

Ala Pro Gln Asn Leu Val Glu Gln Ala Lys Leu Thr Ala Ala Thr Asn
545                 550                 555                 560

Ala Lys Gln
```

<210> SEQ ID NO 28
<211> LENGTH: 1692
<212> TYPE: DNA
<213> ORGANISM: Saccharomyces cerevisiae

<400> SEQUENCE: 28

```
atgtctgaaa ttactttggg taaatatttg ttcgaaagat taaagcaagt caacgttaac     60

accgttttcg gtttgccagg tgacttcaac ttgtccttgt tggacaagat ctacgaagtt    120

gaaggtatga gatgggctgg taacgccaac gaattgaacg ctgcttacgc cgctgatggt    180

tacgctcgta tcaagggtat gtcttgtatc atcaccacct tcggtgtcgg tgaattgtct    240

gctttgaacg gtattgccgg ttcttacgct gaacacgtcg gtgttttgca cgttgttggt    300

gtcccatcca tctctgctca agctaagcaa ttgttgttgc accacacctt gggtaacggt    360

gacttcactg ttttccacag aatgtctgcc aacatttctg aaaccactgc tatgatcact    420

gacattgcta ccgccccagc tgaaattgac agatgtatca gaaccactta cgtcacccaa    480

agaccagtct acttaggttt gccagctaac ttggtcgact tgaacgtccc agctaagttg    540

ttgcaaactc caattgacat gtctttgaag ccaaacgatg ctgaatccga aaaggaagtc    600

attgacacca tcttggcttt ggtcaaggat gctaagaacc cagttatctt ggctgatgct    660

tgttgttcca gacacgacgt caaggctgaa actaagaagt tgattgactt gactcaattc    720

ccagctttcg tcaccccaat gggtaagggt tccattgacg aacaacaccc aagatacggt    780

ggtgtttacg tcggtacctt gtccaagcca gaagttaagg aagccgttga atctgctgac    840

ttgattttgt ctgtcggtgc tttgttgtct gatttcaaca ccggttcttt ctcttactct    900

tacaagacca agaacattgt cgaattccac tccgaccaca tgaagatcag aaacgccact    960

ttcccaggtg tccaaatgaa attcgttttg caaaagttgt tgaccactat tgctgacgcc   1020

gctaagggtt acaagccagt tgctgtccca gctagaactc cagctaacgc tgctgtccca   1080
```

-continued

```
gcttctaccc cattgaagca agaatggatg tggaaccaat tgggtaactt cttgcaagaa   1140

ggtgatgttg tcattgctga aaccggtacc tccgctttcg gtatcaacca aaccactttc   1200

ccaaacaaca cctacggtat ctctcaagtc ttatggggtt ccattggttt caccactggt   1260

gctaccttgg gtgctgcttt cgctgctgaa gaaattgatc caaagaagag agttatctta   1320

ttcattggtg acggttcttt gcaattgact gttcaagaaa tctccaccat gatcagatgg   1380

ggcttgaagc catacttgtt cgtcttgaac aacgatggtt acaccattga aaagttgatt   1440

cacggtccaa aggctcaata caacgaaatt caaggttggg accacctatc cttgttgcca   1500

actttcggtg ctaaggacta tgaaacccac agagtcgcta ccaccggtga atgggacaag   1560

ttgacccaag acaagtcttt caacgacaac tctaagatca gaatgattga aatcatgttg   1620

ccagtcttcg atgctccaca aaacttggtt gaacaagcta agttgactgc tgctaccaac   1680

gctaagcaat aa                                                       1692


<210> SEQ ID NO 29
<211> LENGTH: 563
<212> TYPE: PRT
<213> ORGANISM: Saccharomyces cerevisiae

<400> SEQUENCE: 29

Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255
```

-continued

```
Pro Arg Tyr Gly Gly Val Tyr Val Gly Thr Leu Ser Lys Pro Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp Tyr Val Lys Val Lys Asn Ala Thr
305                 310                 315                 320

Phe Pro Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Asn Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile Arg Leu Ile Glu Leu Lys Leu Pro Val Phe Asp
    530                 535                 540

Ala Pro Glu Ser Leu Ile Lys Gln Ala Gln Leu Thr Ala Ala Thr Asn
545                 550                 555                 560

Ala Lys Gln
```

<210> SEQ ID NO 30
<211> LENGTH: 1693
<212> TYPE: DNA
<213> ORGANISM: Saccharomyces cerevisiae

<400> SEQUENCE: 30

```
atgtctgaaa ttactcttgg aaaatactta tttgaaagat tgaagcaagt taatgttaac      60

accatttttg ggctaccagg cgacttcaac ttgtccctat tggacaagat ttacgaggta     120

gatggattga gatgggctgg taatgcaaat gagctgaacg ccgcctatgc cgccgatggt     180

tacgcacgca tcaagggttt atctgtgctg gtaactactt ttggcgtagg tgaattatct     240

gccttgaatg gtattgcagg atcgtatgca gaacacgtcg gtgtactgca tgttgttggt     300

gtcccctcta tctccgctca ggctaagcaa ttgttgttgc atcatacctt gggtaacggt     360
```

-continued

```
gattttaccg tttttcacag gatgtccgcc aatatctcag aaactacatc aatgattaca    420

gacattgcta cagccccttc agaaatcgat aggttgatca ggacaacatt tataacacaa    480

aggcctagct acttggggtt gccagcgaat ttggtagatc taaaggttcc tggttctctt    540

ttggaaaaac cgattgatct atcattaaaa cctaacgatc ctgaagctga aaaggaagtt    600

attgataccg tactagaatt gatccagaat tcgaaaaacc ctgtcatact atcggatgcc    660

tgtgcttcta ggcacaacgt taaaaaggaa acccagaagt taattgattt gacgcaattc    720

ccagcttttg tgacaccttt aggtaaaggg tcaatagatg aacagcatcc cagatatggc    780

ggtgtttatg tgggaacgct gtccaaacca gacgtgaaac aggccgttga gtcggctgat    840

ttgatccttt cggtcggtgc tttgctctct gattttaaca caggttcgtt ttcctactcc    900

tacaagacta aaaatgtagt ggagtttcat tccgattacg taaaggtgaa gaacgctacg    960

ttccccggcg tacaaatgaa atttgcacta caaaacttac tgaaggttat tcccgatgtt   1020

gttaagggct acaagagcgt tcccgtacca accaaaactc ccgcaaacaa aggtgtacct   1080

gctagcacgc ccttgaaaca agagtggttg tggaacgaat tgtccaagtt cttgcaagaa   1140

ggtgatgtta tcatttccga gaccggcacg tctgccttcg gtatcaatca aactatcttt   1200

cctaaggacg cctacggtat ctcgcaagtg ttgtgggggt ctatcggttt tacaacagga   1260

gcaactttag gtgctgcctt tgccgctgag gagattgacc ccaacaagag agtcatctta   1320

ttcataggtg acgggtcttt gcagttaacc gtccaagaaa tctccaccat gatcagatgg   1380

gggttaaagc cgtatctttt tgtccttaac aacgacggct acactatcga aaagctgatt   1440

catgggcctc acgcagagta caacgaaatc cagacctggg atcacctcgc cctgttgccc   1500

gcatttggtg cgaaaaagta cgaaaatcac aagatcgcca ctacgggcga gtgggacgcc   1560

ttaaccactg attcagagtt ccagaaaaac tcggtgatca gactaattga actgaaactg   1620

cccgtctttg atgctccgga aagtttgatc aaacaagcgc aattgactgc cgctacaaat   1680

gccaaacaat aaa                                                      1693


<210> SEQ ID NO 31
<211> LENGTH: 391
<212> TYPE: PRT
<213> ORGANISM: Saccharomyces cerevisiae

<400> SEQUENCE: 31

Met Ser Ala Ala Ala Asp Arg Leu Asn Leu Thr Ser Gly His Leu Asn
  1               5                  10                  15

Ala Gly Arg Lys Arg Ser Ser Ser Ser Val Ser Leu Lys Ala Ala Glu
             20                  25                  30

Lys Pro Phe Lys Val Thr Val Ile Gly Ser Gly Asn Trp Gly Thr Thr
         35                  40                  45

Ile Ala Lys Val Val Ala Glu Asn Cys Lys Gly Tyr Pro Glu Val Phe
     50                  55                  60

Ala Pro Ile Val Gln Met Trp Val Phe Glu Glu Glu Ile Asn Gly Glu
 65                  70                  75                  80

Lys Leu Thr Glu Ile Ile Asn Thr Arg His Gln Asn Val Lys Tyr Leu
                 85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
```

-continued

```
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 32
<211> LENGTH: 1176
<212> TYPE: DNA
<213> ORGANISM: Saccharomyces cerevisiae

<400> SEQUENCE: 32

```
atgtctgctg ctgctgatag attaaactta acttccggcc acttgaatgc tggtagaaag     60

agaagttcct cttctgtttc tttgaaggct gccgaaaagc ctttcaaggt tactgtgatt    120

ggatctggta actggggtac tactattgcc aaggtggttg ccgaaaattg taagggatac    180

ccagaagttt tcgctccaat agtacaaatg tgggtgttcg aagaagagat caatggtgaa    240

aaattgactg aaatcataaa tactagacat caaaacgtga aatacttgcc tggcatcact    300

ctacccgaca atttggttgc taatccagac ttgattgatt cagtcaagga tgtcgacatc    360

atcgttttca acattccaca tcaatttttg ccccgtatct gtagccaatt gaaaggtcat    420

gttgattcac acgtcagagc tatctcctgt ctaaagggtt ttgaagttgg tgctaaaggt    480

gtccaattgc tatcctctta catcactgag gaactaggta ttcaatgtgg tgctctatct    540

ggtgctaaca ttgccaccga agtcgctcaa gaacactggt ctgaaacaac agttgcttac    600

cacattccaa aggatttcag aggcgagggc aaggacgtcg accataaggt tctaaaggcc    660
```

-continued

```
ttgttccaca gaccttactt ccacgttagt gtcatcgaag atgttgctgg tatctccatc    720

tgtggtgctt tgaagaacgt tgttgcctta ggttgtggtt tcgtcgaagg tctaggctgg    780

ggtaacaacg cttctgctgc catccaaaga gtcggtttgg gtgagatcat cagattcggt    840

caaatgtttt tcccagaatc tagagaagaa acatactacc aagagtctgc tggtgttgct    900

gatttgatca ccacctgcgc tggtggtaga aacgtcaagg ttgctaggct aatggctact    960

tctggtaagg acgcctggga atgtgaaaag gagttgttga atggccaatc cgctcaaggt   1020

ttaattacct gcaaagaagt tcacgaatgg ttggaaacat gtggctctgt cgaagacttc   1080

ccattatttg aagccgtata ccaaatcgtt tacaacaact acccaatgaa gaacctgccg   1140

gacatgattg aagaattaga tctacatgaa gattag                             1176
```

<210> SEQ ID NO 33
<211> LENGTH: 587
<212> TYPE: PRT
<213> ORGANISM: Saccharomyces cerevisiae

<400> SEQUENCE: 33

```
Met Leu Trp Lys Arg Thr Cys Thr Arg Leu Ile Lys Pro Ile Ala Gln
  1               5                  10                  15

Pro Arg Gly Arg Leu Val Arg Arg Ser Cys Tyr Arg Tyr Ala Ser Thr
             20                  25                  30

Gly Thr Gly Ser Thr Asp Ser Ser Ser Gln Trp Leu Lys Tyr Ser Val
         35                  40                  45

Ile Ala Ser Ser Ala Thr Leu Phe Gly Tyr Leu Phe Ala Lys Asn Leu
     50                  55                  60

Tyr Ser Arg Glu Thr Lys Glu Asp Leu Ile Glu Lys Leu Glu Met Val
 65                  70                  75                  80

Lys Lys Ile Asp Pro Val Asn Ser Thr Leu Lys Leu Ser Ser Leu Asp
                 85                  90                  95

Ser Pro Asp Tyr Leu His Asp Pro Val Lys Ile Asp Lys Val Val Glu
            100                 105                 110

Asp Leu Lys Gln Val Leu Gly Asn Lys Pro Glu Asn Tyr Ser Asp Ala
        115                 120                 125

Lys Ser Asp Leu Asp Ala His Ser Asp Thr Tyr Phe Asn Thr His His
    130                 135                 140

Pro Ser Pro Glu Gln Arg Pro Arg Ile Ile Leu Phe Pro His Thr Thr
145                 150                 155                 160

Glu Glu Val Ser Lys Ile Leu Lys Ile Cys His Asp Asn Asn Met Pro
                165                 170                 175

Val Val Pro Phe Ser Gly Gly Thr Ser Leu Glu Gly His Phe Leu Pro
            180                 185                 190

Thr Arg Ile Gly Asp Thr Ile Thr Val Asp Leu Ser Lys Phe Met Asn
        195                 200                 205

Asn Val Val Lys Phe Asp Lys Leu Asp Leu Asp Ile Thr Val Gln Ala
    210                 215                 220

Gly Leu Pro Trp Glu Asp Leu Asn Asp Tyr Leu Ser Asp His Gly Leu
225                 230                 235                 240

Met Phe Gly Cys Asp Pro Gly Pro Gly Ala Gln Ile Gly Gly Cys Ile
                245                 250                 255

Ala Asn Ser Cys Ser Gly Thr Asn Ala Tyr Arg Tyr Gly Thr Met Lys
            260                 265                 270

Glu Asn Ile Ile Asn Met Thr Ile Val Leu Pro Asp Gly Thr Ile Val
```

-continued

```
        275                 280                 285

Lys Thr Lys Lys Arg Pro Arg Lys Ser Ser Ala Gly Tyr Asn Leu Asn
    290                 295                 300

Gly Leu Phe Val Gly Ser Glu Gly Thr Leu Gly Ile Val Thr Glu Ala
305                 310                 315                 320

Thr Val Lys Cys His Val Lys Pro Lys Ala Glu Thr Val Ala Val Val
                325                 330                 335

Ser Phe Asp Thr Ile Lys Asp Ala Ala Ala Cys Ala Ser Asn Leu Thr
            340                 345                 350

Gln Ser Gly Ile His Leu Asn Ala Met Glu Leu Leu Asp Glu Asn Met
        355                 360                 365

Met Lys Leu Ile Asn Ala Ser Glu Ser Thr Asp Arg Cys Asp Trp Val
    370                 375                 380

Glu Lys Pro Thr Met Phe Phe Lys Ile Gly Gly Arg Ser Pro Asn Ile
385                 390                 395                 400

Val Asn Ala Leu Val Asp Glu Val Lys Ala Val Ala Gln Leu Asn His
                405                 410                 415

Cys Asn Ser Phe Gln Phe Ala Lys Asp Asp Asp Glu Lys Leu Glu Leu
            420                 425                 430

Trp Glu Ala Arg Lys Val Ala Leu Trp Ser Val Leu Asp Ala Asp Lys
        435                 440                 445

Ser Lys Asp Lys Ser Ala Lys Ile Trp Thr Thr Asp Val Ala Val Pro
    450                 455                 460

Val Ser Gln Phe Asp Lys Val Ile His Glu Thr Lys Lys Asp Met Gln
465                 470                 475                 480

Ala Ser Lys Leu Ile Asn Ala Ile Val Gly His Ala Gly Asp Gly Asn
                485                 490                 495

Phe His Ala Phe Ile Val Tyr Arg Thr Pro Glu Glu His Glu Thr Cys
            500                 505                 510

Ser Gln Leu Val Asp Arg Met Val Lys Arg Ala Leu Asn Ala Glu Gly
        515                 520                 525

Thr Cys Thr Gly Glu His Gly Val Gly Ile Gly Lys Arg Glu Tyr Leu
    530                 535                 540

Leu Glu Glu Leu Gly Glu Ala Pro Val Asp Leu Met Arg Lys Ile Lys
545                 550                 555                 560

Leu Ala Ile Asp Pro Lys Arg Ile Met Asn Pro Asp Lys Ile Phe Lys
                565                 570                 575

Thr Asp Pro Asn Glu Pro Ala Asn Asp Tyr Arg
            580                 585
```

<210> SEQ ID NO 34
<211> LENGTH: 1764
<212> TYPE: DNA
<213> ORGANISM: Saccharomyces cerevisiae

<400> SEQUENCE: 34

```
atgttgtgga agcgtacttg cacaaggcta ataaagccta ttgcacaacc tagaggaagg      60

ctggtgagaa gatcatgcta cagatacgcc tcaacaggca caggcagcac cgacagcagc     120

agccagtggt taaaatactc tgtcatcgcc tcttcagcta ctctattcgg ttatttgttc     180

gctaagaacc tctattctag ggagactaag gaagatttga tagagaagct ggaaatggtc     240

aaaaagatcg acccagtaaa ttctacgtta aagctgtcct cattggactc accagactat     300

ttgcacgacc cggttaagat cgataaggtt gttgaggacc tgaagcaggt gctgggaaac     360
```

```
aagcctgaaa actactctga tgcgaaatcc gatttggacg cccattcaga tacctacttc    420

aacacgcatc acccctctcc cgagcaaaga cctaggatta tattattccc tcatactacc    480

gaagaagttt ccaaaatttt gaaaatatgt cacgataaca acatgccagt tgtacccttc    540

tcgggcggaa cgtccttgga ggggcacttc ctgcctacaa gaattggaga taccataacc    600

gtagacctgt ccaagtttat gaataacgtc gtaaaatttg acaagctgga cctggacatc    660

accgtgcagg ccggtctacc ctgggaggat ttgaatgact atttgagcga ccacggtttg    720

atgtttggct gtgaccctgg tccaggtgca cagattggtg gttgcattgc taattcttgt    780

tcaggaacca acgcctaccg ttacggtacc atgaaggaga atattataaa catgactata    840

gtgttgccgg acgggaccat tgtcaagacg aagaaaagac ccagaaagtc gagcgctggc    900

tataacttaa atggtttatt tgtgggaagt gaaggtacct taggtattgt tactgaagct    960

actgtcaagt gtcatgtcaa gcccaaagct gaaactgttg cggtggtatc ctttgatact   1020

atcaaggatg cggccgcatg tgcttctaat ctgactcaga gtggtattca tttgaacgcc   1080

atggagttac tggatgaaaa tatgatgaag ttgatcaacg catctgaatc cacggacaga   1140

tgtgattggg tagagaaacc aactatgttt ttcaagattg gtgggagatc tcccaacatt   1200

gtcaatgctc ttgtggatga agttaaggct gtcgcccagt taaatcactg caacagtttt   1260

cagtttgcta aagatgatga cgaaaaattg gaattatggg aagctagaaa ggtcgcgcta   1320

tggtctgtgc tagacgctga taagagcaaa gacaaatcag ctaaaatttg gacaactgat   1380

gtagctgttc ctgtgtcgca gttcgacaag gttattcacg aaactaaaaa ggacatgcaa   1440

gctagtaagc tgatcaacgc cattgttggt catgcaggtg atggtaactt ccatgcattc   1500

atcgtctaca gaacccctga agaacacgaa acctgtagcc aacttgttga cagaatggtc   1560

aagagagcac tgaacgcaga aggcacttgc acgggtgaac acggtgttgg tattggtaaa   1620

agagagtact tgctcgaaga attaggtgaa gcacccgtcg atttgatgag aaagattaag   1680

ctagctattg acccaaagag aatcatgaac ccggacaaaa tctttaaaac tgatccaaac   1740

gagcccgcta atgattacag gtga                                          1764
```

```
<210> SEQ ID NO 35
<211> LENGTH: 591
<212> TYPE: PRT
<213> ORGANISM: Saccharomyces cerevisiae

<400> SEQUENCE: 35

Met Leu Lys Tyr Lys Pro Leu Leu Lys Ile Ser Lys Asn Cys Glu Ala
1               5                   10                  15

Ala Ile Leu Arg Ala Ser Lys Thr Arg Leu Asn Thr Ile Arg Ala Tyr
            20                  25                  30

Gly Ser Thr Val Pro Lys Ser Lys Ser Phe Glu Gln Asp Ser Arg Lys
        35                  40                  45

Arg Thr Gln Ser Trp Thr Ala Leu Arg Val Gly Ala Ile Leu Ala Ala
    50                  55                  60

Thr Ser Ser Val Ala Tyr Leu Asn Trp His Asn Gly Gln Ile Asp Asn
65                  70                  75                  80

Glu Pro Lys Leu Asp Met Asn Lys Gln Lys Ile Ser Pro Ala Glu Val
                85                  90                  95

Ala Lys His Asn Lys Pro Asp Asp Cys Trp Val Val Ile Asn Gly Tyr
            100                 105                 110

Val Tyr Asp Leu Thr Arg Phe Leu Pro Asn His Pro Gly Gly Gln Asp
        115                 120                 125
```

```
Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
    370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                405                 410                 415

Glu Leu Lys Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
        435                 440                 445

Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495

Asp Val Leu Lys Ala Leu Cys Leu Gly Ala Lys Gly Val Gly Leu Gly
            500                 505                 510

Arg Pro Phe Leu Tyr Ala Asn Ser Cys Tyr Gly Arg Asn Gly Val Glu
        515                 520                 525

Lys Ala Ile Glu Ile Leu Arg Asp Glu Ile Glu Met Ser Met Arg Leu
    530                 535                 540
```

-continued

```
Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
            580                 585                 590


<210> SEQ ID NO 36
<211> LENGTH: 1776
<212> TYPE: DNA
<213> ORGANISM: Saccharomyces cerevisiae

<400> SEQUENCE: 36

atgctaaaat acaaaccttt actaaaaatc tcgaagaact gtgaggctgc tatcctcaga     60

gcgtctaaga ctagattgaa cacaatccgc gcgtacggtt ctaccgttcc aaaatccaag    120

tcgttcgaac aagactcaag aaaacgcaca cagtcatgga ctgccttgag agtcggtgca    180

attctagccg ctactagttc cgtggcgtat ctaaactggc ataatggcca aatagacaac    240

gagccgaaac tggatatgaa taaacaaaag atttcgcccg ctgaagttgc caagcataac    300

aagcccgatg attgttgggt tgtgatcaat ggttacgtat acgacttaac gcgattccta    360

ccaaatcatc caggtgggca ggatgttatc aagtttaacg ccgggaaaga tgtcactgct    420

atttttgaac cactacatgc tcctaatgtc atcgataagt atatagctcc cgagaaaaaa    480

ttgggtcccc ttcaaggatc catgcctcct gaacttgtct gtcctcctta tgctcctggt    540

gaaactaagg aagatatcgc tagaaaagaa caactaaaat cgctgctacc tcctctagat    600

aatattatta acctttacga ctttgaatac ttggcctctc aaactttgac taaacaagcg    660

tgggcctact attcctccgg tgctaacgac gaagttactc acagagaaaa ccataatgct    720

tatcatagga ttttttcaa accaaagatc cttgtagatg tacgcaaagt agacatttca    780

actgacatgt tgggttctca tgtggatgtt cccttctacg tgtctgctac agctttgtgt    840

aaactgggaa acccccttaga aggtgaaaaa gatgtcgcca gaggttgtgg ccaaggtgtg    900

acaaaagtcc cacaaatgat atctactttg gcttcatgtt cccctgagga aattattgaa    960

gcagcaccct ctgataaaca aattcaatgg taccaactat atgttaactc tgatagaaag   1020

atcactgatg atttggttaa aaatgtagaa aagctgggtg taaaggcatt atttgtcact   1080

gtggatgctc caagtttagg tcaaagagaa aaagatatga agctgaaatt ttccaataca   1140

aaggctggtc caaaagcgat gaagaaaact aatgtagaag aatctcaagg tgcttcgaga   1200

gcgttatcaa agtttattga cccctctttg acttggaaag atatagaaga gttgaagaaa   1260

aagacaaaac tacctattgt tatcaaaggt gttcaacgta ccgaagatgt tatcaaagca   1320

gcagaaatcg gtgtaagtgg ggtggttcta tccaatcatg gtggtagaca attagatttt   1380

tcaagggctc ccattgaagt cctggctgaa accatgccaa tcctggaaca acgtaacttg   1440

aaggataagt tggaagtttt cgtggacggt ggtgttcgtc gtggtacaga tgtcttgaaa   1500

gcgttatgtc taggtgctaa aggtgttggt ttgggtagac cattcttgta tgcgaactca   1560

tgctatggtc gtaatggtgt tgaaaaagcc attgaaattt taagagatga aattgaaatg   1620

tctatgagac tattaggtgt tactagcatt gcggaattga agcctgatct tttagatcta   1680

tcaacactaa aggcaagaac agttggagta ccaaacgacg tgctgtataa tgaagtttat   1740

gagggaccta ctttaacaga atttgaggat gcatga                             1776


<210> SEQ ID NO 37
```

<211> LENGTH: 348
<212> TYPE: PRT
<213> ORGANISM: Saccharomyces cerevisiae

<400> SEQUENCE: 37

```
Met Ser Ile Pro Glu Thr Gln Lys Gly Val Ile Phe Tyr Glu Ser His
  1               5                  10                  15

Gly Lys Leu Glu Tyr Lys Asp Ile Pro Val Pro Lys Pro Lys Ala Asn
             20                  25                  30

Glu Leu Leu Ile Asn Val Lys Tyr Ser Gly Val Cys His Thr Asp Leu
         35                  40                  45

His Ala Trp His Gly Asp Trp Pro Leu Pro Val Lys Leu Pro Leu Val
     50                  55                  60

Gly Gly His Glu Gly Ala Gly Val Val Val Gly Met Gly Glu Asn Val
 65                  70                  75                  80

Lys Gly Trp Lys Ile Gly Asp Tyr Ala Gly Ile Lys Trp Leu Asn Gly
                 85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345
```

<210> SEQ ID NO 38
<211> LENGTH: 1047
<212> TYPE: DNA
<213> ORGANISM: Saccharomyces cerevisiae

<400> SEQUENCE: 38

-continued

```
atgtctatcc cagaaactca aaaaggtgtt atcttctacg aatcccacgg taagttggaa     60
tacaaagata ttccagttcc aaagccaaag gccaacgaat tgttgatcaa cgttaaatac    120
tctggtgtct gtcacactga cttgcacgct tggcacggtg actggccatt gccagttaag    180
ctaccattag tcggtggtca cgaaggtgcc ggtgtcgttg tcggcatggg tgaaaacgtt    240
aagggctgga agatcggtga ctacgccggt atcaaatggt tgaacggttc ttgtatggcc    300
tgtgaatact gtgaattggg taacgaatcc aactgtcctc acgctgactt gtctggttac    360
acccacgacg gttctttcca acaatacgct accgctgacg ctgttcaagc cgctcacatt    420
cctcaaggta ccgacttggc ccaagtcgcc cccatcttgt gtgctggtat caccgtctac    480
aaggctttga agtctgctaa cttgatggcc ggtcactggg ttgctatctc cggtgctgct    540
ggtggtctag gttctttggc tgttcaatac gccaaggcta tgggttacag agtcttgggt    600
attgacggtg gtgaaggtaa ggaagaatta ttcagatcca tcggtggtga agtcttcatt    660
gacttcacta aggaaaagga cattgtcggt gctgttctaa aggccactga cggtggtgct    720
cacggtgtca tcaacgtttc cgtttccgaa gccgctattg aagcttctac cagatacgtt    780
agagctaacg gtaccaccgt tttggtcggt atgccagctg gtgccaagtg ttgttctgat    840
gtcttcaacc aagtcgtcaa gtccatctct attgttggtt cttacgtcgg taacagagct    900
gacaccagag aagctttgga cttcttcgcc agaggtttgg tcaagtctcc aatcaaggtt    960
gtcggcttgt ctaccttgcc agaaatttac gaaaagatgg aaaagggtca aatcgttggt   1020
agatacgttg ttgacacttc taaataa                                       1047
```

```
<210> SEQ ID NO 39
<211> LENGTH: 351
<212> TYPE: PRT
<213> ORGANISM: Saccharomyces cerevisiae

<400> SEQUENCE: 39

Met Pro Ser Gln Val Ile Pro Glu Lys Gln Lys Ala Ile Val Phe Tyr
  1               5                  10                  15

Glu Thr Asp Gly Lys Leu Glu Tyr Lys Asp Val Thr Val Pro Glu Pro
             20                  25                  30

Lys Pro Asn Glu Ile Leu Val His Val Lys Tyr Ser Gly Val Cys His
         35                  40                  45

Ser Asp Leu His Ala Trp His Gly Asp Trp Pro Phe Gln Leu Lys Phe
     50                  55                  60

Pro Leu Ile Gly Gly His Glu Gly Ala Gly Val Val Val Lys Leu Gly
 65                  70                  75                  80

Ser Asn Val Lys Gly Trp Lys Val Gly Asp Phe Ala Gly Ile Lys Trp
                 85                  90                  95

Leu Asn Gly Thr Cys Met Ser Cys Glu Tyr Cys Glu Val Gly Asn Glu
            100                 105                 110

Ser Gln Cys Pro Tyr Leu Asp Gly Thr Gly Phe Thr His Asp Gly Thr
        115                 120                 125

Phe Gln Glu Tyr Ala Thr Ala Asp Ala Val Gln Ala Ala His Ile Pro
    130                 135                 140

Pro Asn Val Asn Leu Ala Glu Val Ala Pro Ile Leu Cys Ala Gly Ile
145                 150                 155                 160

Thr Val Tyr Lys Ala Leu Lys Arg Ala Asn Val Ile Pro Gly Gln Trp
                165                 170                 175

Val Thr Ile Ser Gly Ala Cys Gly Gly Leu Gly Ser Leu Ala Ile Gln
```

-continued

```
            180                 185                 190

Tyr Ala Leu Ala Met Gly Tyr Arg Val Ile Gly Ile Asp Gly Gly Asn
        195                 200                 205

Ala Lys Arg Lys Leu Phe Glu Gln Leu Gly Gly Glu Ile Phe Ile Asp
    210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
                245                 250                 255

Glu Ala Ser Thr Arg Tyr Cys Arg Pro Asn Gly Thr Val Val Leu Val
            260                 265                 270

Gly Met Pro Ala His Ala Tyr Cys Asn Ser Asp Val Phe Asn Gln Val
        275                 280                 285

Val Lys Ser Ile Ser Ile Val Gly Ser Cys Val Gly Asn Arg Ala Asp
    290                 295                 300

Thr Arg Glu Ala Leu Asp Phe Phe Ala Arg Gly Leu Ile Lys Ser Pro
305                 310                 315                 320

Ile His Leu Ala Gly Leu Ser Asp Val Pro Glu Ile Phe Ala Lys Met
                325                 330                 335

Glu Lys Gly Glu Ile Val Gly Arg Tyr Val Val Glu Thr Ser Lys
            340                 345                 350
```

<210> SEQ ID NO 40
<211> LENGTH: 1056
<212> TYPE: DNA
<213> ORGANISM: Saccharomyces cerevisiae

<400> SEQUENCE: 40

```
atgccttcgc aagtcattcc tgaaaaacaa aaggctattg tcttttatga gacagatgga      60

aaattggaat ataaagacgt cacagttccg gaacctaagc ctaacgaaat tttagtccac     120

gttaaatatt ctggtgtttg tcatagtgac ttgcacgcgt ggcacggtga ttggccattt     180

caattgaaat ttccattaat cggtggtcac gaaggtgctg gtgttgttgt taagttggga     240

tctaacgtta agggctggaa agtcggtgat tttgcaggta taaaatggtt gaatgggact     300

tgcatgtcct gtgaatattg tgaagtaggt aatgaatctc aatgtcctta tttggatggt     360

actggcttca cacatgatgg tacttttcaa gaatacgcaa ctgccgatgc cgttcaagct     420

gcccatattc caccaaacgt caatcttgct gaagttgccc caatcttgtg tgcaggtatc     480

actgtttata aggcgttgaa aagagccaat gtgataccag gccaatgggt cactatatcc     540

ggtgcatgcg gtggcttggg ttctctggca atccaatacg cccttgctat gggttacagg     600

gtcattggta tcgatggtgg taatgccaag cgaaagttat ttgaacaatt aggcggagaa     660

atattcatcg atttcacgga agaaaaagac attgttggtg ctataataaa ggccactaat     720

ggcggttctc atggagttat taatgtgtct gtttctgaag cagctatcga ggcttctacg     780

aggtattgta ggcccaatgg tactgtcgtc ctggttggta tgccagctca tgcttactgc     840

aattccgatg ttttcaatca agttgtaaaa tcaatctcca tcgttggatc ttgtgttgga     900

aatagagctg atacaaggga ggctttagat ttcttcgcca gaggtttgat caaatctccg     960

atccacttag ctggcctatc ggatgttcct gaaatttttg caaagatgga gaagggtgaa    1020

attgttggta gatatgttgt tgagacttct aaatga                              1056
```

<210> SEQ ID NO 41
<211> LENGTH: 500

<212> TYPE: PRT
<213> ORGANISM: Saccharomyces cerevisiae

<400> SEQUENCE: 41

```
Met Thr Lys Leu His Phe Asp Thr Ala Glu Pro Val Lys Ile Thr Leu
  1               5                  10                  15

Pro Asn Gly Leu Thr Tyr Glu Gln Pro Thr Gly Leu Phe Ile Asn Asn
             20                  25                  30

Lys Phe Met Lys Ala Gln Asp Gly Lys Thr Tyr Pro Val Glu Asp Pro
         35                  40                  45

Ser Thr Glu Asn Thr Val Cys Glu Val Ser Ser Ala Thr Thr Glu Asp
     50                  55                  60

Val Glu Tyr Ala Ile Glu Cys Ala Asp Arg Ala Phe His Asp Thr Glu
 65                  70                  75                  80

Trp Ala Thr Gln Asp Pro Arg Glu Arg Gly Arg Leu Leu Ser Lys Leu
                 85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380

Phe Ile Arg Pro Thr Val Phe Tyr Asp Val Asn Glu Asp Met Arg Ile
385                 390                 395                 400
```

```
Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500


<210> SEQ ID NO 42
<211> LENGTH: 1503
<212> TYPE: DNA
<213> ORGANISM: Saccharomyces cerevisiae

<400> SEQUENCE: 42

atgactaagc tacactttga cactgctgaa ccagtcaaga tcacacttcc aaatggtttg      60

acatacgagc aaccaaccgg tctattcatt aacaacaagt ttatgaaagc tcaagacggt     120

aagacctatc ccgtcgaaga tccttccact gaaaacaccg tttgtgaggt ctcttctgcc     180

accactgaag atgttgaata tgctatcgaa tgtgccgacc gtgctttcca cgacactgaa     240

tgggctaccc aagacccaag agaaagaggc cgtctactaa gtaagttggc tgacgaattg     300

gaaagccaaa ttgacttggt ttcttccatt gaagctttgg acaatggtaa aactttggcc     360

ttagcccgtg ggatgttac cattgcaatc aactgtctaa gagatgctgc tgcctatgcc      420

gacaaagtca acggtagaac aatcaacacc ggtgacggct acatgaactt caccacctta     480

gagccaatcg gtgtctgtgg tcaaattatt ccatggaact ttccaataat gatgttggct     540

tggaagatcg ccccagcatt ggccatgggt aacgtctgta tcttgaaacc cgctgctgtc     600

acacctttaa atgccctata ctttgcttct ttatgtaaga aggttggtat tccagctggt     660

gtcgtcaaca tcgttccagg tcctggtaga actgttggtg ctgctttgac caacgaccca     720

agaatcagaa agctggcttt taccggttct acagaagtcg gtaagagtgt tgctgtcgac     780

tcttctgaat ctaacttgaa gaaaatcact ttggaactag gtggtaagtc cgcccatttg     840

gtctttgacg atgctaacat taagaagact ttaccaaatc tagtaaacgg tattttcaag     900

aacgctggtc aaatttgttc ctctggttct agaatttacg ttcaagaagg tatttacgac     960

gaactattgg ctgctttcaa ggcttacttg gaaaccgaaa tcaaagttgg taatccattt    1020

gacaaggcta acttccaagg tgctatcact aaccgtcaac aattcgacac aattatgaac    1080

tacatcgata tcggtaagaa agaaggcgcc aagatcttaa ctggtggcga aaaagttggt    1140

gacaagggtt acttcatcag accaaccgtt ttctacgatg ttaatgaaga catgagaatt    1200

gttaaggaag aaatttttgg accagttgtc actgtcgcaa agttcaagac tttagaagaa    1260

ggtgtcgaaa tggctaacag ctctgaattc ggtctaggtt ctggtatcga aacagaatct    1320

ttgagcacag gtttgaaggt ggccaagatg ttgaaggccg gtaccgtctg gatcaacaca    1380

tacaacgatt ttgactccag agttccattc ggtggtgtta agcaatctgg ttacggtaga    1440

gaaatgggtg aagaagtcta ccatgcatac actgaagtaa aagctgtcag aattaagttg    1500
```

taa 1503

<210> SEQ ID NO 43
<211> LENGTH: 316
<212> TYPE: PRT
<213> ORGANISM: Escherichia coli

<400> SEQUENCE: 43

Met Ser Lys Arg Lys Val Ala Ile Ile Gly Ser Gly Asn Ile Gly Thr
1 5 10 15

Asp Leu Met Ile Lys Ile Leu Arg His Gly Gln His Leu Glu Met Ala
20 25 30

Val Met Val Gly Ile Asp Pro Gln Ser Asp Gly Leu Ala Arg Ala Arg
35 40 45

Arg Met Gly Val Ala Thr Thr His Glu Gly Val Ile Gly Leu Met Asn
50 55 60

Met Pro Glu Phe Ala Asp Ile Asp Ile Val Phe Asp Ala Thr Ser Ala
65 70 75 80

Gly Ala His Val Lys Asn Asp Ala Ala Leu Arg Glu Ala Lys Pro Asp
85 90 95

Ile Arg Leu Ile Asp Leu Thr Pro Ala Ala Ile Gly Pro Tyr Cys Val
100 105 110

Pro Val Val Asn Leu Glu Ala Asn Val Asp Gln Leu Asn Val Asn Met
115 120 125

Val Thr Cys Gly Gly Gln Ala Thr Ile Pro Met Val Ala Ala Val Ser
130 135 140

Arg Val Ala Arg Val His Tyr Ala Glu Ile Ile Ala Ser Ile Ala Ser
145 150 155 160

Lys Ser Ala Gly Pro Gly Thr Arg Ala Asn Ile Asp Glu Phe Thr Glu
165 170 175

Thr Thr Ser Arg Ala Ile Glu Val Val Gly Gly Ala Ala Lys Gly Lys
180 185 190

Ala Ile Ile Val Leu Asn Pro Ala Glu Pro Pro Leu Met Met Arg Asp
195 200 205

Thr Val Tyr Val Leu Ser Asp Glu Ala Ser Gln Asp Asp Ile Glu Ala
210 215 220

Ser Ile Asn Glu Met Ala Glu Ala Val Gln Ala Tyr Val Pro Gly Tyr
225 230 235 240

Arg Leu Lys Gln Arg Val Gln Phe Glu Val Ile Pro Gln Asp Lys Pro
245 250 255

Val Asn Leu Pro Gly Val Gly Gln Phe Ser Gly Leu Lys Thr Ala Val
260 265 270

Trp Leu Glu Val Glu Gly Ala Ala His Tyr Leu Pro Ala Tyr Ala Gly
275 280 285

Asn Leu Asp Ile Met Thr Ser Ser Ala Leu Ala Thr Ala Glu Lys Met
290 295 300

Ala Gln Ser Leu Ala Arg Lys Ala Gly Glu Ala Ala
305 310 315

<210> SEQ ID NO 44
<211> LENGTH: 951
<212> TYPE: DNA
<213> ORGANISM: Escherichia coli

<400> SEQUENCE: 44

-continued

```
atgagtaagc gtaaagtcgc cattatcggt tctggcaaca ttggtaccga tctgatgatt      60

aaaattttgc gtcacggtca gcatctggag atggcggtga tggttggcat tgatcctcag     120

tccgacggtc tggcgcgcgc cagacgtatg ggcgtcgcca ccacccatga aggggtgatc     180

ggactgatga acatgcctga atttgctgat atcgacattg tatttgatgc gaccagcgcc     240

ggtgctcatg tgaaaaacga tgccgcttta cgcgaagcga aaccggatat tcgcttaatt     300

gacctgacgc ctgctgccat cggcccttac tgcgtgccgg tggttaacct cgaggcgaac     360

gtcgatcaac tgaacgtcaa catggtcacc tgcggcggcc aggccaccat tccaatggtg     420

gcggcagttt cacgcgtggc gcgtgttcat tacgccgaaa ttatcgcttc tatcgccagt     480

aaatctgccg gacctggcac gcgtgccaat atcgatgaat ttacggaaac cacttcccga     540

gccattgaag tggtgggcgg cgcggcaaaa gggaaggcga ttattgtgct taacccagca     600

gagccaccgt tgatgatgcg tgacacggtg tatgtattga gcgacgaagc ttcacaagat     660

gatatcgaag cctcaatcaa tgaaatggct gaggcggtgc aggcttacgt accgggttat     720

cgcctgaaac agcgcgtgca gtttgaagtt atcccgcagg ataaaccggt caatttaccg     780

ggcgtggggc aattctccgg actgaaaaca gcggtctggc tggaagtcga aggcgcagcg     840

cattatctgc ctgcctatgc gggcaacctc gacattatga cttccagtgc gctggcgaca     900

gcggaaaaaa tggcccagtc actggcgcgc aaggcaggag aagcggcatg a              951
```

```
<210> SEQ ID NO 45
<211> LENGTH: 512
<212> TYPE: PRT
<213> ORGANISM: Saccharomyces cerevisiae

<400> SEQUENCE: 45

Met Ser Val Asn Pro Glu Phe Ile Ala Asp Gly Ile Asp Phe Tyr Pro
  1               5                  10                  15

Thr Thr Pro Asp Ala Ala Tyr Phe Asn Ala Ala Asp Gly Lys Asn Lys
             20                  25                  30

Val Asn Arg Ile Asn Gly Asn Ser Glu Asn Leu His His Ser Phe Ala
         35                  40                  45

Ser Gly Cys Arg Arg Ser Ser Leu Ser Val Asp Phe Asn Val Thr Ser
     50                  55                  60

Ser Asp Ser Glu Lys Ser Glu Gln Ser Cys Leu Glu Asn Asn Ser Gln
 65                  70                  75                  80

Glu Asp Glu Tyr Phe Cys Asp Ile Phe Ser Thr Glu Leu Lys Leu Asp
                 85                  90                  95

Glu Thr Ser Asn Lys Ser Thr Asp Tyr Ser Ser Ser Asn His Gln Tyr
            100                 105                 110

Pro Glu Gln Leu Glu Leu His Asn Tyr Lys Leu Leu Asn Lys Ile Gly
        115                 120                 125

Glu Gly Ala Phe Ser Arg Val Phe Lys Ala Val Gly Ile Asn Thr Asp
    130                 135                 140

Asp Gln Ala Pro Val Ala Ile Lys Ala Ile Ile Lys Lys Gly Ile Ser
145                 150                 155                 160

Ser Asp Ala Ile Leu Lys Gly Asn Asp Arg Ile Gln Gly Ser Ser Arg
                165                 170                 175

Lys Lys Val Leu Asn Glu Val Ala Ile His Lys Leu Val Ser Lys Asn
            180                 185                 190

Asn Pro His Cys Thr Lys Phe Ile Ala Phe Gln Glu Ser Ala Asn Tyr
        195                 200                 205
```

```
Tyr Tyr Leu Val Thr Glu Leu Val Thr Gly Gly Glu Ile Phe Asp Arg
    210                 215                 220

Ile Val Gln Leu Thr Cys Phe Ser Glu Asp Leu Ala Arg His Val Ile
225                 230                 235                 240

Thr Gln Val Ala Ile Ala Ile Lys His Met His Tyr Met Gly Ile Val
                245                 250                 255

His Arg Asp Val Lys Pro Glu Asn Leu Leu Phe Glu Pro Ile Pro Phe
            260                 265                 270

Tyr Gly Leu Asp Gly Asp Met Gln Lys Glu Asp Glu Phe Thr Leu Gly
        275                 280                 285

Val Gly Gly Gly Gly Ile Gly Leu Val Lys Leu Met Asp Phe Gly Leu
    290                 295                 300

Ala Lys Lys Leu Arg Asn Asn Thr Ala Lys Thr Pro Cys Gly Thr Ile
305                 310                 315                 320

Glu Tyr Val Ala Ser Glu Val Phe Thr Ser Lys Arg Tyr Ser Met Lys
                325                 330                 335

Val Asp Met Trp Ser Ile Gly Cys Val Leu Phe Thr Leu Leu Cys Gly
            340                 345                 350

Tyr Pro Pro Phe Tyr Glu Lys Asn Glu Lys Thr Leu Leu Lys Lys Ile
        355                 360                 365

Ser Arg Gly Asp Tyr Glu Phe Leu Ala Pro Trp Trp Asp Asn Ile Ser
    370                 375                 380

Ser Gly Ala Lys Asn Ala Val Thr His Leu Leu Glu Val Asp Pro Asn
385                 390                 395                 400

Lys Arg Tyr Asp Ile Asp Asp Phe Leu Asn Asp Pro Trp Leu Asn Ser
                405                 410                 415

Tyr Asp Cys Leu Lys Asp Ser Asn Ser Asn Ser Tyr Ala Ser Val Gln
            420                 425                 430

Ser Ile Leu Asn Asp Ser Phe Asp Glu Arg Ala Glu Thr Leu His Cys
        435                 440                 445

Ala Leu Ser Cys Gln Ser Glu Lys Gln Asp Asp Thr Glu Phe Ser Arg
    450                 455                 460

Ser Glu Ser Ser Glu Tyr Ile Phe Met Thr Glu Glu Asp Arg Asn Leu
465                 470                 475                 480

Arg Gly Ser Trp Ile Gly Glu Pro Lys Glu Cys Phe Thr Leu Asp Leu
                485                 490                 495

Ala Thr Ser Ser Ile Tyr Arg Arg Arg Lys Asn Lys Ile Phe Phe Trp
            500                 505                 510


<210> SEQ ID NO 46
<211> LENGTH: 610
<212> TYPE: PRT
<213> ORGANISM: Saccharomyces cerevisiae

<400> SEQUENCE: 46

Met Leu Lys Ile Lys Ala Leu Phe Ser Lys Lys Lys Pro Asp Gln Ala
  1               5                  10                  15

Asp Leu Ser Gln Glu Ser Lys Lys Pro Phe Lys Gly Lys Thr Arg Ser
             20                  25                  30

Ser Gly Thr Asn Asn Lys Asp Val Ser Gln Ile Thr Ser Ser Pro Lys
         35                  40                  45

Lys Ser Phe Gln Asp Lys Asn Ile Val Gln Tyr Pro Ser Val Val Ala
     50                  55                  60

Asp Asp His His Met Lys Ser Leu Thr Asp Glu Leu Val Thr Thr Ile
 65                  70                  75                  80
```

-continued

```
Asp Ser Asp Ser Ser Pro Ser Asp Asn Ile Thr Thr Glu Asn Val Glu
                85                  90                  95

Thr Val Thr Ser Val Pro Ala Ile Asp Val His Glu Ser Ser Glu Gly
            100                 105                 110

Gln Leu Ser Ser Asp Pro Leu Ile Ser Asp Glu Ser Leu Ser Glu Gln
        115                 120                 125

Ser Glu Ile Ile Ser Asp Ile Gln Asp Asp Ser Thr Asp Asp Asp Asn
    130                 135                 140

Met Glu Asp Glu Ile Pro Glu Lys Ser Phe Leu Glu Gln Lys Glu Leu
145                 150                 155                 160

Ile Gly Tyr Lys Leu Ile Asn Lys Ile Gly Glu Gly Ala Phe Ser Lys
                165                 170                 175

Val Phe Arg Ala Ile Pro Ala Lys Asn Ser Ser Asn Glu Phe Leu Thr
            180                 185                 190

Lys Asn Tyr Lys Ala Val Ala Ile Lys Val Ile Lys Lys Ala Asp Leu
        195                 200                 205

Ser Ser Ile Asn Gly Asp His Arg Lys Lys Asp Lys Gly Lys Asp Ser
    210                 215                 220

Thr Lys Thr Ser Ser Arg Asp Gln Val Leu Lys Glu Val Ala Leu His
225                 230                 235                 240

Lys Thr Val Ser Ala Gly Cys Ser Gln Ile Val Ala Phe Ile Asp Phe
                245                 250                 255

Gln Glu Thr Asp Ser Tyr Tyr Tyr Ile Ile Gln Glu Leu Leu Thr Gly
            260                 265                 270

Gly Glu Ile Phe Gly Glu Ile Val Arg Leu Thr Tyr Phe Ser Glu Asp
        275                 280                 285

Leu Ser Arg His Val Ile Lys Gln Leu Ala Leu Ala Val Lys His Met
    290                 295                 300

His Ser Leu Gly Val Val His Arg Asp Ile Lys Pro Glu Asn Leu Leu
305                 310                 315                 320

Phe Glu Pro Ile Glu Phe Thr Arg Ser Ile Lys Pro Lys Leu Arg Lys
                325                 330                 335

Ser Asp Asp Pro Gln Thr Lys Ala Asp Glu Gly Ile Phe Thr Pro Gly
            340                 345                 350

Val Gly Gly Gly Gly Ile Gly Ile Val Lys Leu Ala Asp Phe Gly Leu
        355                 360                 365

Ser Lys Gln Ile Phe Ser Lys Asn Thr Lys Thr Pro Cys Gly Thr Val
    370                 375                 380

Gly Tyr Thr Ala Pro Glu Val Val Lys Asp Glu His Tyr Ser Met Lys
385                 390                 395                 400

Val Asp Met Trp Gly Ile Gly Cys Val Leu Tyr Thr Met Leu Cys Gly
                405                 410                 415

Phe Pro Pro Phe Tyr Asp Glu Lys Ile Asp Thr Leu Thr Glu Lys Ile
            420                 425                 430

Ser Arg Gly Glu Tyr Thr Phe Leu Lys Pro Trp Trp Asp Glu Ile Ser
        435                 440                 445

Ala Gly Ala Lys Asn Ala Val Ala Lys Leu Leu Glu Leu Glu Pro Ser
    450                 455                 460

Lys Arg Tyr Asp Ile Asp Gln Phe Leu Asp Asp Pro Trp Leu Asn Thr
465                 470                 475                 480

Phe Asp Cys Leu Pro Lys Glu Gly Glu Ser Ser Gln Lys Lys Ala Gly
                485                 490                 495
```

-continued

```
Thr Ser Glu Arg Arg His Pro His Lys Lys Gln Phe Gln Leu Phe Gln
            500                 505                 510

Arg Asp Ser Ser Leu Leu Phe Ser Pro Ala Ala Val Ala Met Arg Asp
        515                 520                 525

Ala Phe Asp Ile Gly Asn Ala Val Lys Arg Thr Glu Glu Asp Arg Met
    530                 535                 540

Gly Thr Arg Gly Gly Leu Gly Ser Leu Ala Glu Asp Glu Glu Leu Glu
545                 550                 555                 560

Asp Ser Tyr Ser Gly Ala Gln Gly Asp Glu Gln Leu Glu Gln Asn Met
                565                 570                 575

Phe Gln Leu Thr Leu Asp Thr Ser Thr Ile Leu Gln Arg Arg Lys Lys
            580                 585                 590

Val Gln Glu Asn Asp Val Gly Pro Thr Ile Pro Ile Ser Ala Thr Ile
        595                 600                 605

Arg Glu
    610


<210> SEQ ID NO 47
<211> LENGTH: 1539
<212> TYPE: DNA
<213> ORGANISM: Saccharomyces cerevisiae

<400> SEQUENCE: 47

atgtcagtaa acccagaatt tatagccgat ggcatcgatt tttatccaac aacgcccgat      60

gccgcgtatt tcaatgccgc tgatggtaaa aataaagtta acaggataaa tggtaactca     120

gaaaatttac accactcctt tgcatcgggt tgccgtagat catctctttc agtcgacttt     180

aatgttacct cgtccgattc agaaaaaagt gaacagagct gcttggaaaa caactctcaa     240

gaagacgaat atttttgtga cattttttcc actgaattaa aattagatga aacttctaac     300

aagtcaaccg attattccag ttcaaatcac cagtatcctg aacaactgga gttgcacaat     360

tataaactgc tcaataaaat tggtgaaggg gcattttcca gagtatttaa agcagtaggc     420

atcaacacgg atgaccaagc tcctgttgcc atcaaagcaa tcataaagaa aggcatttcg     480

agcgatgcca tcttaaaagg gaatgataga atccaaggtt ccagcagaaa gaaagtctta     540

aacgaagttg ccatccacaa actggtttcg aaaaataatc cgcattgtac aaaatttatc     600

gcattccagg aatcggcgaa ctactattac ttagtgacgg agttagtcac aggtggggaa     660

atatttgata ggatcgtcca actaacatgc tttagtgaag acttagctcg tcatgtcatt     720

actcaggtag caattgcaat taaacatatg cactacatgg gtattgtgca tcgtgatgtc     780

aaaccagaaa acctactatt tgaacctatc ccattttatg gccttgatgg ggacatgcaa     840

aaagaagacg agtttacatt aggtgtcggc ggaggcggta ttggtttagt gaagctaatg     900

gacttcggac tagccaagaa acttcggaac aataccgcaa aaactccctg cggaacgata     960

gaatacgtcg catcagaagt attcacctcc aaacgatatt ccatgaaagt tgatatgtgg    1020

agtattggct gcgtactatt cacgttattg tgtggatatc ctccgtttta cgaaaagaac    1080

gaaaaaacat tattgaagaa aatatcgaga ggagattacg aattcttggc gccatggtgg    1140

gacaacataa gttctggcgc taagaacgca gttacccatc ttttggaggt tgacccaaac    1200

aagagatacg atatcgatga cttcctaaat gatccttggt taaattcgta cgattgtttg    1260

aaggattcaa actcaaattc ttatgccagc gtgcaaagca tactaaatga ttcattcgat    1320

gagagagcag agaccctaca ttgtgcatta agctgccaat ctgaaaaaca agatgacacc    1380

gagttttcca gaagtgaaag ctcggaatac atatttatga cggaagaaga cagaaaccta    1440
```

```
cggggcagtt ggatcggtga gccaaaagag tgttttacct tagaccttgc aacatcttct   1500

atataccgaa gaaggaagaa caagatattc ttctggtaa                          1539


<210> SEQ ID NO 48
<211> LENGTH: 1833
<212> TYPE: DNA
<213> ORGANISM: Saccharomyces cerevisiae

<400> SEQUENCE: 48

atgcttaaaa taaaggccct tttctcgaaa aagaaaccgg atcaggcaga tttgtctcag     60

gaatctaaaa aaccattcaa gggtaagacc aggtcaagcg gtacaaataa caaagatgtt    120

tcccagatta cttcttcccc taagaaaagc tttcaggaca aaaatatagt tcagtacccg    180

agtgttgtcg cagatgacca tcatatgaag tctttaaccg atgaattagt aaccacgata    240

gactcggact cttcaccgag tgataatatt accacggaaa atgtggaaac agttacttcc    300

gtgccagcta tcgatgtcca tgaaagtagt gaaggtcaat taagttccga ccccttaata    360

tctgacgaat ctctttcgga acaaagcgag attatcagtg atatccagga tgacagtact    420

gatgatgaca atatggaaga tgaaattccg gaaaaatcct tcctcgaaca aaaggaattg    480

ataggttaca agctgatcaa taaaatcggt gaaggtgctt tttcaaaagt ctttagagcc    540

atacctgcta aaaatagttc taatgaattt ttaactaaaa actataaagc tgttgccatt    600

aaagttatca aaaaggcaga tttatcctcg attaatggtg atcatcgtaa gaaggacaaa    660

gggaaggaca gcactaaaac ttcttccaga gatcaagtct tgaaggaagt tgcactacat    720

aagacggttt ccgctggttg ttcacaaatt gtcgcgttca tagacttcca agaaacagat    780

agctattatt atattattca agagttacta accggtgggg aaatcttcgg cgaaattgtt    840

aggttgacct atttcagtga agatttatca aggcatgtaa tcaaacaatt agcactggct    900

gttaaacata tgcattcact aggtgtagtg catcgtgata taaaacctga gaatcttctt    960

tttgaaccga ttgaattcac acgctctata aaaccaaaat tgaggaaatc ggatgatccg   1020

caaacaaagg cagacgaggg aattttcaca ccaggagttg gtggtggtgg aattggtata   1080

gtaaaactag ctgattttgg tttgtctaaa caaatatttt ccaagaacac caagactcct   1140

tgtggtacag tcggttacac tgcccctgaa gttgtcaaag atgagcatta ttctatgaaa   1200

gtggatatgt gggggattgg ttgcgttttg tacacaatgt tatgtgggtt cccgccattc   1260

tatgatgaga aaattgacac tttaactgaa aaaatatcaa ggggtgagta tacctttctg   1320

aaaccttggt gggatgaaat cagcgccggt gccaagaatg ccgtggctaa gctattagaa   1380

ctagagccgt ctaaaagata cgacattgac cagtttttgg acgacccatg gttaaataca   1440

ttcgattgtt taccaaagga gggcgaatct tcacaaaaga aagcaggtac ttccgaaaga   1500

cgccatccgc ataagaaaca attccaacta tttcaaagag actcctcgct actgttttca   1560

ccagctgctg ttgctatgcg tgacgccttt gatattggta atgctgtgaa acgtaccgaa   1620

gaagaccgta tgggaacacg tggaggatta ggctcgcttg ctgaggacga agaattggaa   1680

gatagttaca gtggcgccca aggcgatgaa cagctggaac aaaatatgtt ccaattaacg   1740

ctggatacgt ccacgattct gcaaagaaga aaaaaagttc aagaaaatga cgtagggcct   1800

acaattccaa taagcgccac tatcagggaa tag                                1833


<210> SEQ ID NO 49
<211> LENGTH: 289
<212> TYPE: DNA
```

<213> ORGANISM: Artificial Sequence
<220> FEATURE:
<223> OTHER INFORMATION: Synthetic CYC promoter

<400> SEQUENCE: 49
atttggcgag cgttggttgg tggatcaagc ccacgcgtag gcaatcctcg agcagatccg 60
ccaggcgtgt atatatagcg tggatggcca ggcaacttta gtgctgacac atacaggcat 120
atatatatgt gtgcgacgac acatgatcat atggcatgca tgtgctctgt atgtatataa 180
aactcttgtt ttcttctttt ctctaaatat tctttcctta tacattagga cctttgcagc 240
ataaattact atacttctat agacacgcaa acacaaatac acacactaa 289

<210> SEQ ID NO 50
<211> LENGTH: 401
<212> TYPE: DNA
<213> ORGANISM: Artificial Sequence
<220> FEATURE:
<223> OTHER INFORMATION: Synthetic TEF promoter

<400> SEQUENCE: 50
atagcttcaa aatgtttcta ctcctttttt actcttccag attttctcgg actccgcgca 60
tcgccgtacc acttcaaaac acccaagcac agcatactaa atttcccctc tttcttcctc 120
tagggtgtcg ttaattaccc gtactaaagg tttggaaaag aaaaaagaga ccgcctcgtt 180
tctttttctt cgtcgaaaaa ggcaataaaa atttttatca cgtttctttt tcttgaaaat 240
tttttttttg atttttttct ctttcgatga cctcccattg atatttaagt taataaacgg 300
tcttcaattt ctcaagtttc agtttcattt ttcttgttct attacaactt tttttacttc 360
ttgctcatta gaaagaaagc atagcaatct aatctaagtt t 401

<210> SEQ ID NO 51
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 51
agtttatcat tatcaatact cgccatttca aagaatacgt aaataattaa tagtagtgat 60
tttcctaact ttatttagtc aaaaaattag ccttttaatt ctgctgtaac ccgtacatgc 120
ccaaaatagg gggcgggtta cacagaatat ataacatcgt aggtgtctgg gtgaacagtt 180
tattcctggc atccactaaa tataatggag cccgcttttt aagctggcat ccagaaaaaa 240
aaagaatccc agcaccaaaa tattgttttc ttcaccaacc atcagttcat aggtccattc 300
tcttagcgca actacagaga acaggggcac aaacaggcaa aaaacgggca caacctcaat 360
ggagtgatgc aacctgcctg gagtaaatga tgacacaagg caattgaccc acgcatgtat 420
ctatctcatt ttcttacacc ttctattacc ttctgctctc tctgatttgg aaaaagctga 480
aaaaaaaggt tgaaaccagt tccctgaaat tattccccta cttgactaat aagtatataa 540
agacggtagg tattgattgt aattctgtaa atctatttct taaacttctt aaattctact 600
tttatagtta gtcttttttt tagttttaaa acaccagaac ttagtttcga cggat 655

<210> SEQ ID NO 52
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 52
gccgggatcg aagaaatgat ggtaaatgaa ataggaaatc aaggagcatg aaggcaaaag 60
acaaatataa gggtcgaacg aaaaataaag tgaaaagtgt tgatatgatg tatttggctt 120
tgcggcgccg aaaaaacgag tttacgcaat tgcacaatca tgctgactct gtggcggacc 180
cgcgctcttg ccggcccggc gataacgctg ggcgtgaggc tgtgcccggc ggagtttttt 240
gcgcctgcat tttccaaggt ttaccctgcg ctaaggggcg agattggaga agcaataaga 300
atgccggttg gggttgcgat gatgacgacc acgacaactg gtgtcattat ttaagttgcc 360
gaaagaacct gagtgcattt gcaacatgag tatactagaa gaatgagcca agacttgcga 420
gacgcgagtt tgccggtggt gcgaacaata gagcgaccat gaccttgaag gtgagacgcg 480
cataaccgct agagtacttt gaagaggaaa cagcaatagg gttgctacca gtataaatag 540
acaggtacat acaacactgg aaatggttgt ctgtttgagt acgctttcaa ttcatttggg 600
tgtgcacttt attatgttac aatatggaag ggaactttac acttctccta tgcacatata 660
ttaattaaag tccaatgcta gtagagaagg ggggtaacac ccctccgcgc tcttttccga 720 ttttttttcta aaccgtggaa tatttcggat atccttttgt tgtttccggg tgtacaatat 780
ggacttcctc ttttctggca accaaaccca tacatcggga ttcctataat accttcgttg 840
gtctccctaa catgtaggtg gcggagggga gatatacaat agaacagata ccagacaaga 900
cataatgggc taaacaagac tacaccaatt acactgcctc attgatggtg gtacataacg 960
aactaatact gtagccctag acttgatagc catcatcata tcgaagtttc actacccttt 1020
ttccatttgc catctattga agtaataata ggcgcatgca acttcttttc tttttttttc 1080
ttttctctct cccccgttgt tgtctcacca tatccgcaat gacaaaaaaa tgatggaaga 1140
cactaaagga aaaaattaac gacaaagaca gcaccaacag atgtcgttgt tccagagctg 1200
atgaggggta tctcgaagca cacgaaactt tttccttcct tcattcacgc acactactct 1260
ctaatgagca acggtatacg gccttccttc cagttacttg aatttgaaat aaaaaaaagt 1320
ttgctgtctt gctatcaagt ataaatagac ctgcaattat taatcttttg tttcctcgtc 1380
attgttctcg ttccctttct tccttgtttc tttttctgca caatatttca agctatacca 1440
agcatacaat caactccaag ctggccgc 1468

<210> SEQ ID NO 53
<211> LENGTH: 292
<212> TYPE: DNA
<213> ORGANISM: Artificial Sequence
<220> FEATURE:
<223> OTHER INFORMATION: Synthetic CCW12 promoter

<400> SEQUENCE: 53
ttcgcggcca cctacgccgc tatctttgca acaactatct gcgataactc agcaaatttt 60
gcatattcgt gttgcagtat tgcgataatg ggagtcttac ttccaacata acggcagaaa 120
gaaatgtgag aaaattttgc atcctttgcc tccgttcaag tatataaagt cggcatgctt 180
gataatcttt ctttccatcc tacattgttc taattattct tattctcctt tattctttcc 240
taacatacca agaaattaat cttctgtcat tcgcttaaac actatatcaa ta 292

<210> SEQ ID NO 54
<211> LENGTH: 676
<212> TYPE: DNA
<213> ORGANISM: Artificial Sequence
<220> FEATURE:

<223> OTHER INFORMATION: Synthetic HHT2 promoter

<400> SEQUENCE: 54

```
attttattgt attgattgtt gtttttgcta ctcttttgaa caagatgtag gaaaaaagat     60
agagaaaaga ataaattaag cgaaaaaaaa aaaatctctt tcaccgcctc atcctaatat    120
acttatatat gatataacta catacgcaca aacacgtatg tatctagccg aataacaaca    180
gcccaggcgc gagtgaacaa catattaaat taaacgcctt cttgtcagtt gttttgttct    240
ggtctggtct gcatttcgcg cccgaaaaag cttgagacgc gaagctccca gaacgtcctg    300
ccatacaaat gcgaaactct cggtctagta ccactttccc ggtgccaaac gaccacagtt    360
gtccgttccg agcacttcgc attaagcgcg tgaaactatt ggcacgccct aaggggctcc    420
tacggatggg agttggtcat ttagcgttca ttatcgccca atgtgacgca caatcacggc    480
tatggctcgg tgtcaaaaca tagtttgcgt gataacagcg tgttgtgctc tctcgcgttg    540
cttcttgtga ccgcagttgt atataaataa tctttttctt gttcttttat ataggaccac    600
tgttttgtga cttccacttt ggcccttcca actgttcttc ccttttact aaaggatcca    660
agcaaacact ccacaa                                                    676
```

<210> SEQ ID NO 55
<211> LENGTH: 252
<212> TYPE: DNA
<213> ORGANISM: Artificial Sequence
<220> FEATURE:
<223> OTHER INFORMATION: Synthetic CYC1 terminator

<400> SEQUENCE: 55

```
tcatgtaatt agttatgtca cgcttacatt cacgccctcc ccccacatcc gctctaaccg     60
aaaaggaagg agttagacaa cctgaagtct aggtccctat ttattttttt atagttatgt    120
tagtattaag aacgttattt atatttcaaa tttttctttt ttttctgtac agacgcgtgt    180
acgcatgtaa cattatactg aaaaccttgc ttgagaaggt tttgggacgc tcgaaggctt    240
taatttgcgg cc                                                        252
```

<210> SEQ ID NO 56
<211> LENGTH: 31
<212> TYPE: DNA
<213> ORGANISM: Artificial Sequence
<220> FEATURE:
<223> OTHER INFORMATION: primer

<400> SEQUENCE: 56

```
cgagctcttc gcggccacct acgccgctat c                                    31
```

<210> SEQ ID NO 57
<211> LENGTH: 32
<212> TYPE: DNA
<213> ORGANISM: Artificial Sequence
<220> FEATURE:
<223> OTHER INFORMATION: primer

<400> SEQUENCE: 57

```
gctctagata ttgatatagt gtttaagcga at                                   32
```

<210> SEQ ID NO 58
<211> LENGTH: 27
<212> TYPE: DNA
<213> ORGANISM: Artificial Sequence
<220> FEATURE:
<223> OTHER INFORMATION: primer

<400> SEQUENCE: 58
cggccatggc gggagctcgc atgcaag 27

<210> SEQ ID NO 59
<211> LENGTH: 28
<212> TYPE: DNA
<213> ORGANISM: Artificial Sequence
<220> FEATURE:
<223> OTHER INFORMATION: primer

<400> SEQUENCE: 59
cgggatatca ctagtgagct cgctccgc 28

<210> SEQ ID NO 60
<211> LENGTH: 2321
<212> TYPE: DNA
<213> ORGANISM: Artificial Sequence
<220> FEATURE:
<223> OTHER INFORMATION: Synthetic HPH cassette

<400> SEQUENCE: 60
gccgggagag ctcgcatgca agtaacctat tcaaagtaat atctcataca tgtttcatga 60
gggtaacaac atgcgactgg gtgagcatat gttccgctga tgtgatgtgc aagataaaca 120
agcaaggcag aaactaactt cttcttcatg taataaacac accccgcgtt tatttaccta 180
tctctaaact tcaacacctt atatcataac taatatttct tgagataagc acactgcacc 240
cataccttcc ttaaaaacgt agcttccagt ttttggtggt tccggcttcc ttcccgattc 300
cgcccgctaa acgcatattt ttgttgcctg gtggcatttg caaaatgcat aacctatgca 360
tttaaaagat tatgtatgct cttctgactt ttcgtgtgat gaggctcgtg gaaaaaatga 420
ataatttatg aatttgagaa caattttgtg ttgttacggt attttactat ggaataatca 480
atcaattgag gattttatgc aaatatcgtt tgaatatttt tccgaccctt tgagtacttt 540
tcttcataat tgcataatat tgtccgctgc cccttttttct gttagacggt gtcttgatct 600
acttgctatc gttcaacacc accttatttt ctaactattt ttttttagc tcatttgaat 660 cagcttatgg tgatggcaca tttttgcata aacctagctg tcctcgttga acataggaaa 720
aaaaaatata taaacaaggc tctttcactc tccttgcaat cagatttggg tttgttccct 780
ttattttcat atttcttgtc atattccttt ctcaattatt attttctact cataacctca 840
cgcaaaataa cacagtcaaa tcctcgagat gaaaaagcct gaactcaccg cgacgtctgt 900
cgagaagttt ctgatcgaaa agttcgacag cgtctccgac ctgatgcagc tctcggaggg 960
cgaagaatct cgtgctttca gcttcgatgt aggagggcgt ggatatgtcc tgcgggtaaa 1020
tagctgcgcc gatggtttct acaaagatcg ttatgtttat cggcactttg catcggccgc 1080
gctcccgatt ccggaagtgc ttgacattgg ggaattcagc gagagcctga cctattgcat 1140
ctcccgccgt gcacagggtg tcacgttgca agacctgcct gaaaccgaac tgcccgctgt 1200
tctgcagccg gtcgcggagg ccatggatgc gatcgctgcg gccgatctta gccagacgag 1260
cgggttcggc ccattcggac cgcaaggaat cggtcaatac actacatggc gtgatttcat 1320
atgcgcgatt gctgatcccc atgtgtatca ctggcaaact gtgatggacg acaccgtcag 1380
tgcgtccgtc gcgcaggctc tcgatgagct gatgctttgg gccgaggact gccccgaagt 1440
ccggcacctc gtgcacgcgg atttcggctc caacaatgtc ctgacggaca atggccgcat 1500
aacagcggtc attgactgga gcgaggcgat gttcggggat tcccaatacg aggtcgccaa 1560

-continued catcttcttc tggaggccgt ggttggcttg tatggagcag cagacgcgct acttcgagcg 1620
gaggcatccg gagcttgcag gatcgccgcg gctccgggcg tatatgctcc gcattggtct 1680
tgaccaactc tatcagagct tggttgacgg caatttcgat gatgcagctt gggcgcaggg 1740
tcgatgcgac gcaatcgtcc gatccggagc cgggactgtc gggcgtacac aaatcgcccg 1800
cagaagcgcg gccgtctgga ccgatggctg tgtagaagta ctcgccgata gtggaaaccg 1860
acgccccagc actcgtccgg atcgggagat gggggaggct aactgaggat ccgtagatac 1920
attgatgcta tcaatcaaga gaactggaaa gattgtgtaa ccttgaaaaa cggtgaaact 1980
tacgggtcca agattgtcta cagattttcc tgatttgcca gcttactatc cttcttgaaa 2040
atatgcactc tatatctttt agttcttaat tgcaacacat agatttgctg tataacgaat 2100
tttatgctat tttttaaatt tggagttcag tgataaaagt gtcacagcga atttcctcac 2160
atgtagggac cgaattgttt acaagttctc tgtaccacca tggagacatc aaaaattgaa 2220
aatctatgga aagatatgga cggtagcaac aagaatatag cacgagccgc ggagcgagct 2280
cggccgcact agtgatatcc cgcggccatg gcggccggga g 2321

<210> SEQ ID NO 61
<211> LENGTH: 18
<212> TYPE: DNA
<213> ORGANISM: Artificial Sequence
<220> FEATURE:
<223> OTHER INFORMATION: primer

<400> SEQUENCE: 61
gaaacagcta tgaccatg 18

<210> SEQ ID NO 62
<211> LENGTH: 32
<212> TYPE: DNA
<213> ORGANISM: Artificial Sequence
<220> FEATURE:
<223> OTHER INFORMATION: primer

<400> SEQUENCE: 62
gacatgacga gctcgaattg ggtaccggcc gc 32

<210> SEQ ID NO 63
<211> LENGTH: 4173
<212> TYPE: DNA
<213> ORGANISM: Artificial Sequence
<220> FEATURE:
<223> OTHER INFORMATION: Synthetic pUC57-Ura3HA vector

<400> SEQUENCE: 63
gatgacggtg aaaacctctg acacatgcag ctcccggaga cggtcacagc ttgtctgtaa 60
gcggatgccg ggagcagaca agcccgtcag ggcgcgtcag cgggtgttgg cgggtgtcgg 120
ggctggctta actatgcggc atcagagcag attgtactga gagtgcacca tatgcggtgt 180
gaaataccgc acagatgcgt aaggagaaaa taccgcatca ggcgccattc gccattcagg 240
ctgcgcaact gttgggaagg gcgatcggtg cgggcctctt cgctattacg ccagctggcg 300
aaagggggat gtgctgcaag gcgattaagt tgggtaacgc cagggttttc ccagtcacga 360
cgttgtaaaa cgacggccag tgaattcgag ctcggtacct cgcgaatgca tctagatatc 420
ggatcccgac gagctgcacc gcggtggcgg ccgtatcttt tacccatacg atgttcctga 480
ctatgcgggc tatccctatg acgtcccgga ctatgcagga tcctatccat atgacgttcc 540
agattacgct gctcagtgcg gccgcctgag agtgcaccat accacagctt ttcaattcaa 600

-continued ttcatcattt ttttttatt ctttttttg atttcggttt ctttgaaatt tttttgattc 660
ggtaatctcc gaacagaagg aagaacgaag gaaggagcac agacttagat tggtatatat 720
acgcatatgt agtgttgaag aaacatgaaa ttgcccagta ttcttaaccc aactgcacag 780
aacaaaaacc tgcaggaaac gaagataaat catgtcgaaa gctacatata aggaacgtgc 840
tgctactcat cctagtcctg ttgctgccaa gctatttaat atcatgcacg aaaagcaaac 900
aaacttgtgt gcttcattgg atgttcgtac caccaaggaa ttactggagt tagttgaagc 960
attaggtccc aaaatttgtt tactaaaaac acatgtggat atcttgactg atttttccat 1020
ggagggcaca gttaagccgc taaaggcatt atccgccaag tacaattttt tactcttcga 1080
agacagaaaa tttgctgaca ttggtaatac agtcaaattg cagtactctg cgggtgtata 1140
cagaatagca gaatgggcag acattacgaa tgcacacggt gtggtgggcc caggtattgt 1200
tagcggtttg aagcaggcgg cagaagaagt aacaaaggaa cctagaggcc ttttgatgtt 1260
agcagaattg tcatgcaagg gctccctatc tactggagaa tatactaagg gtactgttga 1320
cattgcgaag agcgacaaag attttgttat cggctttatt gctcaaagag acatgggtgg 1380
aagagatgaa ggttacgatt ggttgattat gacacccggt gtgggtttag atgacaaggg 1440
agacgcattg ggtcaacagt atagaaccgt ggatgatgtg gtctctacag gatctgacat 1500
tattattgtt ggaagaggac tatttgcaaa gggaagggat gctaaggtag agggtgaacg 1560
ttacagaaaa gcaggctggg aagcatattt gagaagatgc ggccagcaaa actaaaaaac 1620
tgtattataa gtaaatgcat gtatactaaa ctcacaaatt agagcttcaa tttaattata 1680
tcagttatta ccctatgcgg tgtgaaatac cgcacagatg cgtaaggaga aaataccgca 1740
tcaggaaatt gtagcggccg cgaatttgag cttatctttt acccatacga tgttcctgac 1800
tatgcgggct atccctatga cgtcccggac tatgcaggat cctatccata tgacgttcca 1860
gattacgcta ctagcggggg gcccggtgac gggcccgtcg actgcagagg cctgcatgca 1920
agcttggcgt aatcatggtc atagctgttt cctgtgtgaa attgttatcc gctcacaatt 1980
ccacacaaca tacgagccgg aagcataaag tgtaaagcct ggggtgccta atgagtgagc 2040
taactcacat taattgcgtt gcgctcactg cccgctttcc agtcgggaaa cctgtcgtgc 2100
cagctgcatt aatgaatcgg ccaacgcgcg gggagaggcg gtttgcgtat tgggcgctct 2160
tccgcttcct cgctcactga ctcgctgcgc tcggtcgttc ggctgcggcg agcggtatca 2220
gctcactcaa aggcggtaat acggttatcc acagaatcag gggataacgc aggaaagaac 2280
atgtgagcaa aaggccagca aaaggccagg aaccgtaaaa aggccgcgtt gctggcgttt 2340
ttccataggc tccgcccccc tgacgagcat cacaaaaatc gacgctcaag tcagaggtgg 2400
cgaaacccga caggactata aagataccag gcgtttcccc ctggaagctc cctcgtgcgc 2460
tctcctgttc cgaccctgcc gcttaccgga tacctgtccg cctttctccc ttcgggaagc 2520
gtggcgcttt ctcatagctc acgctgtagg tatctcagtt cggtgtaggt cgttcgctcc 2580
aagctgggct gtgtgcacga accccccgtt cagcccgacc gctgcgcctt atccggtaac 2640
tatcgtcttg agtccaaccc ggtaagacac gacttatcgc cactggcagc agccactggt 2700
aacaggatta gcagagcgag gtatgtaggc ggtgctacag agttcttgaa gtggtggcct 2760
aactacggct acactagaag aacagtattt ggtatctgcg ctctgctgaa gccagttacc 2820
ttcggaaaaa gagttggtag ctcttgatcc ggcaaacaaa ccaccgctgg tagcggtggt 2880 tttttgttt gcaagcagca gattacgcgc agaaaaaaag gatctcaaga agatcctttg 2940

```
atcttttcta cggggtctga cgctcagtgg aacgaaaact cacgttaagg gattttggtc   3000

atgagattat caaaaaggat cttcacctag atccttttaa attaaaaatg aagttttaaa   3060

tcaatctaaa gtatatatga gtaaacttgg tctgacagtt accaatgctt aatcagtgag   3120

gcacctatct cagcgatctg tctatttcgt tcatccatag ttgcctgact ccccgtcgtg   3180

tagataacta cgatacggga gggcttacca tctggcccca gtgctgcaat gataccgcga   3240

gacccacgct caccggctcc agatttatca gcaataaacc agccagccgg aagggccgag   3300

cgcagaagtg gtcctgcaac tttatccgcc tccatccagt ctattaattg ttgccgggaa   3360

gctagagtaa gtagttcgcc agttaatagt ttgcgcaacg ttgttgccat tgctacaggc   3420

atcgtggtgt cacgctcgtc gtttggtatg gcttcattca gctccggttc ccaacgatca   3480

aggcgagtta catgatcccc catgttgtgc aaaaaagcgg ttagctcctt cggtcctccg   3540

atcgttgtca gaagtaagtt ggccgcagtg ttatcactca tggttatggc agcactgcat   3600

aattctctta ctgtcatgcc atccgtaaga tgcttttctg tgactggtga gtactcaacc   3660

aagtcattct gagaatagtg tatgcggcga ccgagttgct cttgcccggc gtcaatacgg   3720

gataataccg cgccacatag cagaacttta aaagtgctca tcattggaaa acgttcttcg   3780

gggcgaaaac tctcaaggat cttaccgctg ttgagatcca gttcgatgta acccactcgt   3840

gcacccaact gatcttcagc atcttttact ttcaccagcg tttctgggtg agcaaaaaca   3900

ggaaggcaaa atgccgcaaa aaagggaata agggcgacac ggaaatgttg aatactcata   3960

ctcttccttt ttcaatatta ttgaagcatt tatcagggtt attgtctcat gagcggatac   4020

atatttgaat gtatttagaa aaataaacaa ataggggttc cgcgcacatt tccccgaaaa   4080

gtgccacctg acgtctaaga aaccattatt atcatgacat taacctataa aaataggcgt   4140

atcacgaggc cctttcgtct cgcgcgtttc ggt                                4173
```

<210> SEQ ID NO 64
<211> LENGTH: 62
<212> TYPE: DNA
<213> ORGANISM: Artificial Sequence
<220> FEATURE:
<223> OTHER INFORMATION: primer

<400> SEQUENCE: 64

```
gcttataaaa ctttaactaa taattagaga ttaaatcgct taaggtttcc cgactggaaa     60

gc                                                                    62
```

<210> SEQ ID NO 65
<211> LENGTH: 64
<212> TYPE: DNA
<213> ORGANISM: Artificial Sequence
<220> FEATURE:
<223> OTHER INFORMATION: primer

<400> SEQUENCE: 65

```
ctactcataa cctcacgcaa aataacacag tcaaatcaat caaaccagtc acgacgttgt     60

aaaa                                                                  64
```

<210> SEQ ID NO 66
<211> LENGTH: 20
<212> TYPE: DNA
<213> ORGANISM: Artificial Sequence
<220> FEATURE:
<223> OTHER INFORMATION: primer

<400> SEQUENCE: 66

-continued ggacgtaaag ggtagcctcc 20

<210> SEQ ID NO 67
<211> LENGTH: 22
<212> TYPE: DNA
<213> ORGANISM: Artificial Sequence
<220> FEATURE:
<223> OTHER INFORMATION: primer

<400> SEQUENCE: 67
gaagcggacc cagacttaag cc 22

<210> SEQ ID NO 68
<211> LENGTH: 70
<212> TYPE: DNA
<213> ORGANISM: Artificial Sequence
<220> FEATURE:
<223> OTHER INFORMATION: primer

<400> SEQUENCE: 68
ccctatgtct ctggccgatc acgcgccatt gtccctcaga aacaaatcaa ccagtcacga 60
cgttgtaaaa 70

<210> SEQ ID NO 69
<211> LENGTH: 70
<212> TYPE: DNA
<213> ORGANISM: Artificial Sequence
<220> FEATURE:
<223> OTHER INFORMATION: primer

<400> SEQUENCE: 69
tagaagcaac tgtgccgaca gcctctgaat gagtggtgtt gtaaccaccc aggtttcccg 60
actggaaagc 70

<210> SEQ ID NO 70
<211> LENGTH: 25
<212> TYPE: DNA
<213> ORGANISM: Artificial Sequence
<220> FEATURE:
<223> OTHER INFORMATION: primer

<400> SEQUENCE: 70
tcaatgagac tgttgtcctc ctact 25

<210> SEQ ID NO 71
<211> LENGTH: 24
<212> TYPE: DNA
<213> ORGANISM: Artificial Sequence
<220> FEATURE:
<223> OTHER INFORMATION: primer

<400> SEQUENCE: 71
tacatccttg tcgagccttg ggca 24

<210> SEQ ID NO 72
<211> LENGTH: 65
<212> TYPE: DNA
<213> ORGANISM: Artificial Sequence
<220> FEATURE:
<223> OTHER INFORMATION: primer

<400> SEQUENCE: 72
ccgaaatgat tccctttcct gcacaacacg agatctttca cgcatccagt cacgacgttg 60
taaaa 65

<210> SEQ ID NO 73
<211> LENGTH: 64
<212> TYPE: DNA
<213> ORGANISM: Artificial Sequence
<220> FEATURE:
<223> OTHER INFORMATION: primer

<400> SEQUENCE: 73
aaagtagcct taaagctagg ctataatcat gcatcctcaa attctaggtt tcccgacgga 60
aagc 64

<210> SEQ ID NO 74
<211> LENGTH: 25
<212> TYPE: DNA
<213> ORGANISM: Artificial Sequence
<220> FEATURE:
<223> OTHER INFORMATION: primer

<400> SEQUENCE: 74
cgcaagaacg tagtatccac atgcc 25

<210> SEQ ID NO 75
<211> LENGTH: 21
<212> TYPE: DNA
<213> ORGANISM: Artificial Sequence
<220> FEATURE:
<223> OTHER INFORMATION: primer

<400> SEQUENCE: 75
ggatatttac agaacgatgc g 21

<210> SEQ ID NO 76
<211> LENGTH: 37
<212> TYPE: DNA
<213> ORGANISM: Artificial Sequence
<220> FEATURE:
<223> OTHER INFORMATION: primer

<400> SEQUENCE: 76
caggaattca aaacgatgac taaaatcttc gcttacg 37

<210> SEQ ID NO 77
<211> LENGTH: 35
<212> TYPE: DNA
<213> ORGANISM: Artificial Sequence
<220> FEATURE:
<223> OTHER INFORMATION: primer

<400> SEQUENCE: 77
cgcttaagcc tcgagttaac cgaccttaac tggag 35

<210> SEQ ID NO 78
<211> LENGTH: 71
<212> TYPE: DNA
<213> ORGANISM: Artificial Sequence
<220> FEATURE:
<223> OTHER INFORMATION: primer

<400> SEQUENCE: 78
agtataaata aaaaacccaa gtaatatagc aaaaacatat tgccaacaaa ccagtcacga 60
cgttgtaaaa c 71

-continued

<210> SEQ ID NO 79
<211> LENGTH: 70
<212> TYPE: DNA
<213> ORGANISM: Artificial Sequence
<220> FEATURE:
<223> OTHER INFORMATION: primer

<400> SEQUENCE: 79
aatttattta tttgcaacaa taattcgttt ttgagtacac tactaatggc aggtttcccg 60
actggaaagc 70

<210> SEQ ID NO 80
<211> LENGTH: 19
<212> TYPE: DNA
<213> ORGANISM: Artificial Sequence
<220> FEATURE:
<223> OTHER INFORMATION: primer

<400> SEQUENCE: 80
ttgtgctatt gcagtcctc 19

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
ttgagtacac tactaatggc 20

<210> SEQ ID NO 82
<211> LENGTH: 80
<212> TYPE: DNA
<213> ORGANISM: Artificial Sequence
<220> FEATURE:
<223> OTHER INFORMATION: primer

<400> SEQUENCE: 82
caactatctc atatacaatg tctatcccag aaactcaaaa aggtgttatc ttctacgaat 60
ccagtcacga cgttgtaaaa 80

<210> SEQ ID NO 83
<211> LENGTH: 80
<212> TYPE: DNA
<213> ORGANISM: Artificial Sequence
<220> FEATURE:
<223> OTHER INFORMATION: primer

<400> SEQUENCE: 83
ataagaaatt cgcttattta gaagtgtcaa caacgtatct accaacgatt tgaccctttt 60
aggtttcccg actggaaagc 80

<210> SEQ ID NO 84
<211> LENGTH: 20
<212> TYPE: DNA
<213> ORGANISM: Artificial Sequence
<220> FEATURE:
<223> OTHER INFORMATION: primer

<400> SEQUENCE: 84
tcaagctata ccaagcatac 20

<210> SEQ ID NO 85

<211> LENGTH: 19
<212> TYPE: DNA
<213> ORGANISM: Artificial Sequence
<220> FEATURE:
<223> OTHER INFORMATION: primer

<400> SEQUENCE: 85
acctcatgct atacctgag 19

<210> SEQ ID NO 86
<211> LENGTH: 64
<212> TYPE: DNA
<213> ORGANISM: Artificial Sequence
<220> FEATURE:
<223> OTHER INFORMATION: primer

<400> SEQUENCE: 86
caagaaacat ctttaacata cacaaacaca tactatcaga atacccagtc acgacgttgt 60
aaaa 64

<210> SEQ ID NO 87
<211> LENGTH: 65
<212> TYPE: DNA
<213> ORGANISM: Artificial Sequence
<220> FEATURE:
<223> OTHER INFORMATION: primer

<400> SEQUENCE: 87
gtattttgtg tatatgacgg aaagaaatgc aggttggtac attacaggtt tcccgactgg 60
aaagc 65

<210> SEQ ID NO 88
<211> LENGTH: 24
<212> TYPE: DNA
<213> ORGANISM: Artificial Sequence
<220> FEATURE:
<223> OTHER INFORMATION: primer

<400> SEQUENCE: 88
gcatcgggaa cgtatgtaac attg 24

<210> SEQ ID NO 89
<211> LENGTH: 19
<212> TYPE: DNA
<213> ORGANISM: Artificial Sequence
<220> FEATURE:
<223> OTHER INFORMATION: primer

<400> SEQUENCE: 89
tgacgtaaga ccaagtaag 19

<210> SEQ ID NO 90
<211> LENGTH: 55
<212> TYPE: DNA
<213> ORGANISM: Artificial Sequence
<220> FEATURE:
<223> OTHER INFORMATION: primer

<400> SEQUENCE: 90
ctatagggcg aattggctag cttatcatta tcaatactcg ccatttcaaa gaata 55

<210> SEQ ID NO 91
<211> LENGTH: 66
<212> TYPE: DNA
<213> ORGANISM: Artificial Sequence
<220> FEATURE:
<223> OTHER INFORMATION: primer

<400> SEQUENCE: 91
ctcgaggggg ggcccggtac ctcgaaacta agttctggtg ttttaaaact aaaaaaaaga 60
ctaact 66

<210> SEQ ID NO 92
<211> LENGTH: 6110
<212> TYPE: DNA
<213> ORGANISM: Artificial Sequence
<220> FEATURE:
<223> OTHER INFORMATION: Synthetic pCS-Ex1 vector

<400> SEQUENCE: 92
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtacgcatt taagcataaa cacgcactat gccgttcttc tcatgtatat 180
atatatacag gcaacacgca gatataggtg cgacgtgaac agtgagctgt atgtgcgcag 240
ctcgcgttgc attttcggaa gcgctcgttt tcggaaacgc tttgaagttc ctattccgaa 300
gttcctattc tctagctaga aagtatagga acttcagagc gcttttgaaa accaaaagcg 360
ctctgaagac gcactttcaa aaaaccaaaa acgcaccgga ctgtaacgag ctactaaaat 420
attgcgaata ccgcttccac aaacattgct caaaagtatc tctttgctat atatctctgt 480
gctatatccc tatataacct acccatccac ctttcgctcc ttgaacttgc atctaaactc 540
gacctctaca ttttttatgt ttatctctag tattactctt tagacaaaaa aattgtagta 600
agaactattc atagagtgaa tcgaaaacaa tacgaaaatg taaacatttc ctatacgtag 660
tatatagaga caaaatagaa gaaaccgttc ataattttct gaccaatgaa gaatcatcaa 720
cgctatcact ttctgttcac aaagtatgcg caatccacat cggtatagaa tataatcggg 780
gatgccttta tcttgaaaaa atgcacccgc agcttcgcta gtaatcagta aacgcgggaa 840
gtggagtcag gcttttttta tggaagagaa aatagacacc aaagtagcct tcttctaacc 900
ttaacggacc tacagtgcaa aaagttatca agagactgca ttatagagcg cacaaaggag 960
aaaaaaagta atctaagatg ctttgttaga aaaatagcgc tctcgggatg catttttgta 1020
gaacaaaaaa gaagtataga ttctttgttg gtaaaatagc gctctcgcgt tgcatttctg 1080
ttctgtaaaa atgcagctca gattctttgt ttgaaaaatt agcgctctcg cgttgcattt 1140
ttgttttaca aaaatgaagc acagattctt cgttggtaaa atagcgcttt cgcgttgcat 1200
ttctgttctg taaaaatgca gctcagattc tttgtttgaa aaattagcgc tctcgcgttg 1260
catttttgtt ctacaaaatg aagcacagat gcttcgttaa tgtgctgcaa ggcgattaag 1320
ttgggtaacg ccagggtttt cccagtcacg acgttgtaaa acgacggcca gtgaattgta 1380
atacgactca ctatagggcg aattggctag cttatcatta tcaatactcg ccatttcaaa 1440
gaatacgtaa ataattaata gtagtgattt tcctaacttt atttagtcaa aaaattagcc 1500
ttttaattct gctgtaaccc gtacatgccc aaaatagggg gcgggttaca cagaatatat 1560
aacatcgtag gtgtctgggt gaacagttta ttcctggcat ccactaaata taatggagcc 1620
cgctttttaa gctggcatcc agaaaaaaaa agaatcccag caccaaaata ttgttttctt 1680
caccaaccat cagttcatag gtccattctc ttagcgcaac tacagagaac aggggcacaa 1740
acaggcaaaa aacgggcaca acctcaatgg agtgatgcaa cctgcctgga gtaaatgatg 1800

-continued

```
acacaaggca attgacccac gcatgtatct atctcatttt cttacacctt ctattacctt   1860
ctgctctctc tgatttggaa aaagctgaaa aaaaaggttg aaaccagttc cctgaaatta   1920
ttcccctact tgactaataa gtatataaag acggtaggta ttgattgtaa ttctgtaaat   1980
ctatttctta aacttcttaa attctacttt tatagttagt ctttttttta gttttaaaac   2040
accagaactt agtttcgagg taccgggccc cccctcgagg tcgacggtat cgataagctt   2100
gatatcgaat tcctgcagcc cgggggatcc actagttcta gagcggccgc caccgcggtg   2160
gagctcggtt ctgcttatcc ttacgacgtg cctgactacg cctgaacccg atgcaaatga   2220
gacgatcgtc tattcctggt ccggttttct ctgccctctc ttctattcac ttttttttata   2280
ctttatataa aattatataa atgacataac tgaaacgcca cacgtcctct cctattcgtt   2340
aacgcctgtc tgtagcgctg ttactgaagc tgcgcaagta gttttttcac cgtataggcc   2400
ctctttttct ctctctttct ttctctcccg cgctgatctc ttcttcgaaa cacagagtgc   2460
accataccac cttttcaatt catcattttt tttttattct tttttttgat ttcggtttcc   2520
ttgaaatttt tttgattcgg taatctccga acagaaggaa gaacgaagga aggagcacag   2580
acttagattg gtatatatac gcatatgtag tgttgaagaa acatgaaatt gcccagtatt   2640
cttaacccaa ctgcacagaa caaaaacctc caggaaacga agataaatca tgtcgaaagc   2700
tacatataag gaacgtgctg ctactcatcc tagtcctgtt gctgccaagc tatttaatat   2760
catgcacgaa aagcaaacaa acttgtgtgc ttcattggat gttcgtacca ccaaggaatt   2820
actggagtta gttgaagcat taggtcccaa aatttgttta ctaaaaacac atgtggatat   2880
cttgactgat tttccatgg agggcacagt taagccgcta aaggcattat ccgccaagta   2940
caatttttta ctcttcgaag acagaaaatt tgctgacatt ggtaatacag tcaaattgca   3000
gtactctgcg ggtgtataca gaatagcaga atgggcagac attacgaatg cacacggtgt   3060
ggtgggccca ggtattgtta gcggtttgaa gcaggcggca gaagaagtaa caaaggaacc   3120
tagaggcctt ttgatgttag cagaattgtc atgcaagggc tccctatcta ctggagaata   3180
tactaagggt actgttgaca ttgcgaagag cgacaaagat tttgttatcg gctttattgc   3240
tcaaagagac atgggtggaa gagatgaagg ttacgattgg ttgattatga cacccggtgt   3300
gggtttagat gacaagggag acgcattggg tcaacagtat agaaccgtgg atgatgtggt   3360
ctctacagga tctgacatta ttattgttgg aagaggacta tttgcaaagg gaagggatgc   3420
taaggtagag ggtgaacgtt acagaaaagc aggctgggaa gcatatttga gaagatgcgg   3480
ccagcaaaac taatcatgta attagttatg tcacgcttac attcacgccc tccccccaca   3540
tccgctctaa ccgaaaagga aggagttaga caacctgaag tctaggtccc tatttatttt   3600
tttatagtta tgttagtatt aagaacgtta tttatatttc aaatttttct tttttttctg   3660
tacagacgcg tgtacgcatg taacattata ctgaaaacct tgcttgagaa ggttttggga   3720
cgctcgaagg ctttaatttg cgtctgtagc gctgttactg aagctgcgca agtagttttt   3780
tcaccgtata ggccctcttt ttctctctct ttctttctct cccgcgctga tctcttcttc   3840
gaaacatcat gaataaaaag aaaaaggaaa tcaagaaaaa aaagccataa tttatcccac   3900
atttttttt attgtcgctg ttcacaccgc ataacgaaga tattggctag ctaaccagct   3960
tttgttccct ttagtgaggg ttaatttcga gcttggcgta atcatggtca tagctgtttc   4020
ctgtgtgaaa ttgttatccg ctcacaattc cacacaacat acgagccgga agcataaagt   4080
gtaaagcctg gggtgcctaa tgagtgagct aactcacatt aattgcgttg cgctcactgc   4140
ccgctttcca gtcgggaaac ctgtcgtgcc agctgcatta atgaatcggc caacgcgcgg   4200
```

-continued

```
ggagaggcgg tttgcgtatt gggcgctctt ccgcttcctc gctcactgac tcgctgcgct   4260

cggtcgttcg gctgcggcga gcggtatcag ctcactcaaa ggcggtaata cggttatcca   4320

cagaatcagg ggataacgca ggaaagaaca tgtgagcaaa aggccagcaa aaggccagga   4380

accgtaaaaa ggccgcgttg ctggcgtttt tccataggct ccgcccccct gacgagcatc   4440

acaaaaatcg acgctcaagt cagaggtggc gaaacccgac aggactataa agataccagg   4500

cgtttccccc tggaagctcc ctcgtgcgct ctcctgttcc gaccctgccg cttaccggat   4560

acctgtccgc ctttctccct tcgggaagcg tggcgctttc tcatagctca cgctgtaggt   4620

atctcagttc ggtgtaggtc gttcgctcca agctgggctg tgtgcacgaa ccccccgttc   4680

agcccgaccg ctgcgcctta tccggtaact atcgtcttga gtccaacccg gtaagacacg   4740

acttatcgcc actggcagca gccactggta acaggattag cagagcgagg tatgtaggcg   4800

gtgctacaga gttcttgaag tggtggccta actacggcta cactagaagg acagtatttg   4860

gtatctgcgc tctgctgaag ccagttacct tcggaaaaag agttggtagc tcttgatccg   4920

gcaaacaaac caccgctggt agcggtggtt tttttgtttg caagcagcag attacgcgca   4980

gaaaaaaagg atctcaagaa gatcctttga tcttttctac ggggtctgac gctcagtgga   5040

acgaaaactc acgttaaggg attttggtca tgagattatc aaaaaggatc ttcacctaga   5100

tccttttaaa ttaaaaatga agttttaaat caatctaaag tatatatgag taaacttggt   5160

ctgacatcag aagaactcgt caagaaggcg atagaaggcg atgcgctgcg aatcgggagc   5220

ggcgataccg taaagcacga ggaagcggtc agcccattcg ccgccaagct cttcagcaat   5280

atcacgggta gccaacgcta tgtcctgata gcggtccgcc acacccagcc ggccacagtc   5340

gatgaatcca gaaaagcggc cattttccac catgatattc ggcaagcagg catcgccatg   5400

ggtcacgacg agatcctcgc cgtcgggcat gctcgccttg agcctggcga acagttcggc   5460

tggcgcgagc ccctgatgct cttcgtccag atcatcctga tcgacaagac cggcttccat   5520

ccgagtacgt gctcgctcga tgcgatgttt cgcttggtgg tcgaatgggc aggtagccgg   5580

atcaagcgta tgcagccgcc gcattgcatc agccatgatg gatactttct cggcaggagc   5640

aaggtgagat gacaggagat cctgccccgg cacttcgccc aatagcagcc agtcccttcc   5700

cgcttcagtg acaacgtcga gcacagctgc gcaaggaacg cccgtcgtgg ccagccacga   5760

tagccgcgct gcctcgtctt gcagttcatt cagggcaccg gacaggtcgg tcttgacaaa   5820

aagaaccggg cgcccctgcg ctgacagccg gaacacggcg gcatcagagc agccgattgt   5880

ctgttgtgcc cagtcatagc cgaatagcct ctccacccaa gcggccggag aacctgcgtg   5940

caatccatct tgttcaattc gagtgcattc aacatcagcc atactcttcc tttttcaata   6000

ttattgaagc atttatcagg gttattgtct catgagcgga tacatatttg aatgtattta   6060

gaaaaataaa caaatagggg ttccgcgcac atttccccga aaagtgccac             6110
```

<210> SEQ ID NO 93
<211> LENGTH: 55
<212> TYPE: DNA
<213> ORGANISM: Artificial Sequence
<220> FEATURE:
<223> OTHER INFORMATION: primer

<400> SEQUENCE: 93

```
accagaactt agtttcgaga aacaatgaat caacaggata ttgaacaggt ggtga         55
```

<210> SEQ ID NO 94

<211> LENGTH: 50
<212> TYPE: DNA
<213> ORGANISM: Artificial Sequence
<220> FEATURE:
<223> OTHER INFORMATION: primer

<400> SEQUENCE: 94
gtaaggataa gcagaaccgt taaacaatgc gaaacgcatc gactaataca 50

<210> SEQ ID NO 95
<211> LENGTH: 7413
<212> TYPE: DNA
<213> ORGANISM: Artificial Sequence
<220> FEATURE:
<223> OTHER INFORMATION: Synthetic MD1040 vector

<400> SEQUENCE: 95
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtacgcatt taagcataaa cacgcactat gccgttcttc tcatgtatat 180
atatatacag gcaacacgca gatataggtg cgacgtgaac agtgagctgt atgtgcgcag 240
ctcgcgttgc attttcggaa gcgctcgttt tcggaaacgc tttgaagttc ctattccgaa 300
gttcctattc tctagctaga aagtatagga acttcagagc gcttttgaaa accaaaagcg 360
ctctgaagac gcactttcaa aaaaccaaaa acgcaccgga ctgtaacgag ctactaaaat 420
attgcgaata ccgcttccac aaacattgct caaaagtatc tctttgctat atatctctgt 480
gctatatccc tatataacct acccatccac ctttcgctcc ttgaacttgc atctaaactc 540
gacctctaca tttttatgt ttatctctag tattactctt tagacaaaaa aattgtagta 600
agaactattc atagagtgaa tcgaaaacaa tacgaaaatg taaacatttc ctatacgtag 660
tatatagaga caaaatagaa gaaaccgttc ataattttct gaccaatgaa gaatcatcaa 720
cgctatcact ttctgttcac aaagtatgcg caatccacat cggtatagaa tataatcggg 780
gatgccttta tcttgaaaaa atgcacccgc agcttcgcta gtaatcagta aacgcgggaa 840
gtggagtcag gcttttttta tggaagagaa aatagacacc aaagtagcct tcttctaacc 900
ttaacggacc tacagtgcaa aaagttatca agagactgca ttatagagcg cacaaaggag 960
aaaaaaagta atctaagatg ctttgttaga aaaatagcgc tctcgggatg catttttgta 1020
gaacaaaaaa gaagtataga ttctttgttg gtaaaatagc gctctcgcgt tgcatttctg 1080
ttctgtaaaa atgcagctca gattctttgt ttgaaaaatt agcgctctcg cgttgcattt 1140
ttgttttaca aaaatgaagc acagattctt cgttggtaaa atagcgcttt cgcgttgcat 1200
ttctgttctg taaaaatgca gctcagattc tttgtttgaa aaattagcgc tctcgcgttg 1260
catttttgtt ctacaaaatg aagcacagat gcttcgttaa tgtgctgcaa ggcgattaag 1320
ttgggtaacg ccagggtttt cccagtcacg acgttgtaaa acgacggcca gtgaattgta 1380
atacgactca ctatagggcg aattggctag cttatcatta tcaatactcg ccatttcaaa 1440
gaatacgtaa ataattaata gtagtgattt tcctaacttt atttagtcaa aaaattagcc 1500
ttttaattct gctgtaaccc gtacatgccc aaaatagggg gcgggttaca cagaatatat 1560
aacatcgtag gtgtctgggt gaacagttta ttcctggcat ccactaaata taatggagcc 1620
cgctttttaa gctggcatcc agaaaaaaaa agaatcccag caccaaaata ttgttttctt 1680
caccaaccat cagttcatag gtccattctc ttagcgcaac tacagagaac aggggcacaa 1740
acaggcaaaa aacgggcaca acctcaatgg agtgatgcaa cctgcctgga gtaaatgatg 1800

-continued acacaaggca attgacccac gcatgtatct atctcatttt cttacacctt ctattacctt 1860
ctgctctctc tgatttggaa aaagctgaaa aaaaaggttg aaaccagttc cctgaaatta 1920
ttcccctact tgactaataa gtatataaag acggtaggta ttgattgtaa ttctgtaaat 1980
ctatttctta aacttcttaa attctacttt tatagttagt cttttttta gttttaaaac 2040 accagaactt agtttcgaga aacaatgaat caacaggata ttgaacaggt ggtgaaagcg 2100
gtactgctga aaatgcaaag cagtgacacg ccgtccgccg ccgttcatga gatgggcgtt 2160
ttcgcgtccc tggatgacgc cgttgcggca gccaaagtcg cccagcaagg gttaaaaagc 2220
gtggcaatgc gccagttagc cattgctgcc attcgtgaag caggcgaaaa acacgccaga 2280
gatttagcgg aacttgccgt cagtgaaacc ggcatggggc gcgttgaaga taaatttgca 2340
aaaaacgtcg ctcaggcgcg cggcacacca ggcgttgagt gcctctctcc gcaagtgctg 2400
actggcgaca acggcctgac cctaattgaa aacgcaccct ggggcgtggt ggcttcggtg 2460
acgccttcca ctaacccggc ggcaaccgta attaacaacg ccatcagcct gattgccgcg 2520
ggcaacagcg tcatttttgc cccgcatccg gcggcgaaaa aagtctccca gcgggcgatt 2580
acgctgctca accaggcgat tgttgccgca ggtgggccgg aaaacttact ggttactgtg 2640
gcaaatccgg atatcgaaac cgcgcaacgc ttgttcaagt ttccgggtat cggcctgctg 2700
gtggtaaccg gcggcgaagc ggtagtagaa gcggcgcgta aacacaccaa taaacgtctg 2760
attgccgcag gcgctggcaa cccgccggta gtggtggatg aaaccgccga cctcgcccgt 2820
gccgctcagt ccatcgtcaa aggcgcttct ttcgataaca acatcatttg tgccgacgaa 2880
aaggtactga ttgttgttga tagcgtagcc gatgaactga tgcgtctgat ggaaggccag 2940
cacgcggtga aactgaccgc agaacaggcg cagcagctgc aaccggtgtt gctgaaaaat 3000
atcgacgagc gcggaaaagg caccgtcagc cgtgactggg ttggtcgcga cgcaggcaaa 3060
atcgcggcgg caatcggcct taaagttccg caagaaacgc gcctgctgtt tgtggaaacc 3120
accgcagaac atccgtttgc cgtgactgaa ctgatgatgc cggtgttgcc cgtcgtgcgc 3180
gtcgccaacg tggcggatgc cattgcgcta gcggtgaaac tggaaggcgg ttgccaccac 3240
acggcggcaa tgcactcgcg caacatcgaa aacatgaacc agatggcgaa tgctattgat 3300
accagcattt tcgttaagaa cggaccgtgc attgccgggc tggggctggg cggggaaggc 3360
tggaccacca tgaccatcac cacgccaacc ggtgaagggg taaccagcgc gcgtacgttt 3420
gtccgtctgc gtcgctgtgt attagtcgat gcgtttcgca ttgtttaacg gttctgctta 3480
tccttacgac gtgcctgact acgcctgaac ccgatgcaaa tgagacgatc gtctattcct 3540
ggtccggttt tctctgccct ctcttctatt cacttttttt atactttata taaaattata 3600
taaatgacat aactgaaacg ccacacgtcc tctcctattc gttaacgcct gtctgtagcg 3660
ctgttactga agctgcgcaa gtagtttttt caccgtatag gccctctttt tctctctctt 3720
tctttctctc ccgcgctgat ctcttcttcg aaacacagag tgcaccatac caccttttca 3780
attcatcatt tttttttat tcttttttt gatttcggtt tccttgaaat ttttttgatt 3840
cggtaatctc cgaacagaag gaagaacgaa ggaaggagca cagacttaga ttggtatata 3900
tacgcatatg tagtgttgaa gaaacatgaa attgcccagt attcttaacc caactgcaca 3960
gaacaaaaac ctccaggaaa cgaagataaa tcatgtcgaa agctacatat aaggaacgtg 4020
ctgctactca tcctagtcct gttgctgcca agctatttaa tatcatgcac gaaaagcaaa 4080
caaacttgtg tgcttcattg gatgttcgta ccaccaagga attactggag ttagttgaag 4140

-continued

```
cattaggtcc caaaatttgt ttactaaaaa cacatgtgga tatcttgact gatttttcca   4200
tggagggcac agttaagccg ctaaaggcat tatccgccaa gtacaatttt ttactcttcg   4260
aagacagaaa atttgctgac attggtaata cagtcaaatt gcagtactct gcgggtgtat   4320
acagaatagc agaatgggca gacattacga atgcacacgg tgtggtgggc ccaggtattg   4380
ttagcggttt gaagcaggcg gcagaagaag taacaaagga acctagaggc cttttgatgt   4440
tagcagaatt gtcatgcaag ggctccctat ctactggaga atatactaag ggtactgttg   4500
acattgcgaa gagcgacaaa gattttgtta tcggctttat tgctcaaaga gacatgggtg   4560
gaagagatga aggttacgat tggttgatta tgacacccgg tgtgggttta gatgacaagg   4620
gagacgcatt gggtcaacag tatagaaccg tggatgatgt ggtctctaca ggatctgaca   4680
ttattattgt tggaagagga ctatttgcaa agggaaggga tgctaaggta gagggtgaac   4740
gttacagaaa agcaggctgg gaagcatatt tgagaagatg cggccagcaa aactaatcat   4800
gtaattagtt atgtcacgct tacattcacg ccctcccccc acatccgctc taaccgaaaa   4860
ggaaggagtt agacaacctg aagtctaggt ccctatttat ttttttatag ttatgttagt   4920
attaagaacg ttatttatat ttcaaatttt tctttttttt ctgtacagac gcgtgtacgc   4980
atgtaacatt atactgaaaa ccttgcttga gaaggttttg ggacgctcga aggctttaat   5040
ttgcgtctgt agcgctgtta ctgaagctgc gcaagtagtt ttttcaccgt ataggccctc   5100
tttttctctc tctttctttc tctcccgcgc tgatctcttc ttcgaaacat catgaataaa   5160
aagaaaaagg aaatcaagaa aaaaaagcca taatttatcc cacatttttt tttattgtcg   5220
ctgttcacac cgcataacga agatattggc tagctaacca gcttttgttc cctttagtga   5280
gggttaattt cgagcttggc gtaatcatgg tcatagctgt ttcctgtgtg aaattgttat   5340
ccgctcacaa ttccacacaa catacgagcc ggaagcataa agtgtaaagc ctggggtgcc   5400
taatgagtga gctaactcac attaattgcg ttgcgctcac tgcccgcttt ccagtcggga   5460
aacctgtcgt gccagctgca ttaatgaatc ggccaacgcg cggggagagg cggtttgcgt   5520
attgggcgct cttccgcttc ctcgctcact gactcgctgc gctcggtcgt tcggctgcgg   5580
cgagcggtat cagctcactc aaaggcggta atacggttat ccacagaatc aggggataac   5640
gcaggaaaga acatgtgagc aaaaggccag caaaaggcca ggaaccgtaa aaaggccgcg   5700
ttgctggcgt ttttccatag gctccgcccc cctgacgagc atcacaaaaa tcgacgctca   5760
agtcagaggt ggcgaaaccc gacaggacta taaagatacc aggcgtttcc ccctggaagc   5820
tccctcgtgc gctctcctgt tccgaccctg ccgcttaccg gatacctgtc cgcctttctc   5880
ccttcgggaa gcgtggcgct ttctcatagc tcacgctgta ggtatctcag ttcggtgtag   5940
gtcgttcgct ccaagctggg ctgtgtgcac gaaccccccg ttcagcccga ccgctgcgcc   6000
ttatccggta actatcgtct tgagtccaac ccggtaagac acgacttatc gccactggca   6060
gcagccactg gtaacaggat tagcagagcg aggtatgtag gcggtgctac agagttcttg   6120
aagtggtggc ctaactacgg ctacactaga aggacagtat ttggtatctg cgctctgctg   6180
aagccagtta ccttcggaaa aagagttggt agctcttgat ccggcaaaca aaccaccgct   6240
ggtagcggtg gtttttttgt ttgcaagcag cagattacgc gcagaaaaaa aggatctcaa   6300
gaagatcctt tgatcttttc tacggggtct gacgctcagt ggaacgaaaa ctcacgttaa   6360
gggattttgg tcatgagatt atcaaaaagg atcttcacct agatcctttt aaattaaaaa   6420
tgaagtttta aatcaatcta aagtatatat gagtaaactt ggtctgacat cagaagaact   6480
cgtcaagaag gcgatagaag gcgatgcgct gcgaatcggg agcggcgata ccgtaaagca   6540
```

cgaggaagcg gtcagcccat tcgccgccaa gctcttcagc aatatcacgg gtagccaacg 6600
ctatgtcctg atagcggtcc gccacaccca gccggccaca gtcgatgaat ccagaaaagc 6660
ggccattttc caccatgata ttcggcaagc aggcatcgcc atgggtcacg acgagatcct 6720
cgccgtcggg catgctcgcc ttgagcctgg cgaacagttc ggctggcgcg agcccctgat 6780
gctcttcgtc cagatcatcc tgatcgacaa gaccggcttc catccgagta cgtgctcgct 6840
cgatgcgatg tttcgcttgg tggtcgaatg ggcaggtagc cggatcaagc gtatgcagcc 6900
gccgcattgc atcagccatg atggatactt tctcggcagg agcaaggtga gatgacagga 6960
gatcctgccc cggcacttcg cccaatagca gccagtccct tcccgcttca gtgacaacgt 7020
cgagcacagc tgcgcaagga acgcccgtcg tggccagcca cgatagccgc gctgcctcgt 7080
cttgcagttc attcagggca ccggacaggt cggtcttgac aaaaagaacc gggcgcccct 7140
gcgctgacag ccggaacacg gcggcatcag agcagccgat tgtctgttgt gcccagtcat 7200
agccgaatag cctctccacc caagcggccg gagaacctgc gtgcaatcca tcttgttcaa 7260
ttcgagtgca ttcaacatca gccatactct tcctttttca atattattga agcatttatc 7320
agggttattg tctcatgagc ggatacatat ttgaatgtat ttagaaaaat aaacaaatag 7380
gggttccgcg cacatttccc cgaaaagtgc cac 7413

<210> SEQ ID NO 96
<211> LENGTH: 59
<212> TYPE: DNA
<213> ORGANISM: Artificial Sequence
<220> FEATURE:
<223> OTHER INFORMATION: primer

<400> SEQUENCE: 96
aatcttgtgc tattgcagtc ctcttttata tacagtataa tacgactcac tatagggcg 59

<210> SEQ ID NO 97
<211> LENGTH: 60
<212> TYPE: DNA
<213> ORGANISM: Artificial Sequence
<220> FEATURE:
<223> OTHER INFORMATION: primer

<400> SEQUENCE: 97
atgcgaattg cgtaattcac ggcgataacg tagtattaat taaccctcac taaagggaac 60

<210> SEQ ID NO 98
<211> LENGTH: 19
<212> TYPE: DNA
<213> ORGANISM: Artificial Sequence
<220> FEATURE:
<223> OTHER INFORMATION: primer

<400> SEQUENCE: 98
gcccacaact tatcaagtg 19

<210> SEQ ID NO 99
<211> LENGTH: 19
<212> TYPE: DNA
<213> ORGANISM: Artificial Sequence
<220> FEATURE:
<223> OTHER INFORMATION: primer

<400> SEQUENCE: 99
ttataagaca agcgcaggg 19

<210> SEQ ID NO 100
<211> LENGTH: 19
<212> TYPE: DNA
<213> ORGANISM: Artificial Sequence
<220> FEATURE:
<223> OTHER INFORMATION: primer

<400> SEQUENCE: 100
gcccacaact tatcaagtg 19

<210> SEQ ID NO 101
<211> LENGTH: 19
<212> TYPE: DNA
<213> ORGANISM: Artificial Sequence
<220> FEATURE:
<223> OTHER INFORMATION: primer

<400> SEQUENCE: 101
ttataagaca agcgcaggg 19

<210> SEQ ID NO 102
<211> LENGTH: 52
<212> TYPE: DNA
<213> ORGANISM: Artificial Sequence
<220> FEATURE:
<223> OTHER INFORMATION: primer

<400> SEQUENCE: 102
aacactatat caatagaaac aatgtcagta aacccagaat ttatagccga tg 52

<210> SEQ ID NO 103
<211> LENGTH: 49
<212> TYPE: DNA
<213> ORGANISM: Artificial Sequence
<220> FEATURE:
<223> OTHER INFORMATION: primer

<400> SEQUENCE: 103
aggataagca gaaccgttac cagaagaata tcttgttctt ccttcttcg 49

<210> SEQ ID NO 104
<211> LENGTH: 79
<212> TYPE: DNA
<213> ORGANISM: Artificial Sequence
<220> FEATURE:
<223> OTHER INFORMATION: primer

<400> SEQUENCE: 104
aataagaagt ttggtaatat tcaattcgaa gtgttcagtc ttttacttct cttgttttaa 60
tacgactcac tatagggcg 79

<210> SEQ ID NO 105
<211> LENGTH: 79
<212> TYPE: DNA
<213> ORGANISM: Artificial Sequence
<220> FEATURE:
<223> OTHER INFORMATION: primer

<400> SEQUENCE: 105
atatgaaagt attttgtgta tatgacggaa agaaatgcag gttggtacat tacaacaatt 60
aaccctcact aaagggaac 79

<210> SEQ ID NO 106
<211> LENGTH: 22

<212> TYPE: DNA
<213> ORGANISM: Artificial Sequence
<220> FEATURE:
<223> OTHER INFORMATION: primer

<400> SEQUENCE: 106
tatgcatcca gcttctatat cg 22

<210> SEQ ID NO 107
<211> LENGTH: 20
<212> TYPE: DNA
<213> ORGANISM: Artificial Sequence
<220> FEATURE:
<223> OTHER INFORMATION: primer

<400> SEQUENCE: 107
ccttaggcat ttgcctagag 20

<210> SEQ ID NO 108
<211> LENGTH: 40
<212> TYPE: DNA
<213> ORGANISM: Artificial Sequence
<220> FEATURE:
<223> OTHER INFORMATION: primer

<400> SEQUENCE: 108
gggccccccc tcgaggatct cgtgtaattg tccaaatctg 40

<210> SEQ ID NO 109
<211> LENGTH: 41
<212> TYPE: DNA
<213> ORGANISM: Artificial Sequence
<220> FEATURE:
<223> OTHER INFORMATION: primer

<400> SEQUENCE: 109
tacgtgacat gaattcccat gtgcattaca acacatttta c 41

<210> SEQ ID NO 110
<211> LENGTH: 30
<212> TYPE: DNA
<213> ORGANISM: Artificial Sequence
<220> FEATURE:
<223> OTHER INFORMATION: primer

<400> SEQUENCE: 110
atgggaattc atgtcacgta agagctcgac 30

<210> SEQ ID NO 111
<211> LENGTH: 35
<212> TYPE: DNA
<213> ORGANISM: Artificial Sequence
<220> FEATURE:
<223> OTHER INFORMATION: primer

<400> SEQUENCE: 111
ggcggccgct ctagagtaac ttcctgccga tttcg 35

<210> SEQ ID NO 112
<211> LENGTH: 36
<212> TYPE: DNA
<213> ORGANISM: Artificial Sequence
<220> FEATURE:
<223> OTHER INFORMATION: primer

<400> SEQUENCE: 112
tgcacatggg aattccggcc agtgaattgt aatacg 36

<210> SEQ ID NO 113
<211> LENGTH: 49
<212> TYPE: DNA
<213> ORGANISM: Artificial Sequence
<220> FEATURE:
<223> OTHER INFORMATION: primer

<400> SEQUENCE: 113
acgtgacatg aattctgttt tattgatata gtgtttaagc gaatgacag 49

<210> SEQ ID NO 114
<211> LENGTH: 30
<212> TYPE: DNA
<213> ORGANISM: Artificial Sequence
<220> FEATURE:
<223> OTHER INFORMATION: primer

<400> SEQUENCE: 114
ctttcctaac ataccaagaa attaatcttc 30

<210> SEQ ID NO 115
<211> LENGTH: 20
<212> TYPE: DNA
<213> ORGANISM: Artificial Sequence
<220> FEATURE:
<223> OTHER INFORMATION: primer

<400> SEQUENCE: 115
gccagcaaca gcatttagag 20

<210> SEQ ID NO 116
<211> LENGTH: 36
<212> TYPE: DNA
<213> ORGANISM: Artificial Sequence
<220> FEATURE:
<223> OTHER INFORMATION: primer

<400> SEQUENCE: 116
gggccccccc tcgaggcata gagcttgcag attagc 36

<210> SEQ ID NO 117
<211> LENGTH: 35
<212> TYPE: DNA
<213> ORGANISM: Artificial Sequence
<220> FEATURE:
<223> OTHER INFORMATION: primer

<400> SEQUENCE: 117
tgatcggcat gaattcgcta cgtatgcgcc agttg 35

<210> SEQ ID NO 118
<211> LENGTH: 35
<212> TYPE: DNA
<213> ORGANISM: Artificial Sequence
<220> FEATURE:
<223> OTHER INFORMATION: primer

<400> SEQUENCE: 118
tagcgaattc atgccgatca agagattaga tacag 35

<210> SEQ ID NO 119
<211> LENGTH: 38
<212> TYPE: DNA
<213> ORGANISM: Artificial Sequence
<220> FEATURE:
<223> OTHER INFORMATION: primer

<400> SEQUENCE: 119
ggcggccgct ctagagtatg gttgtcagtg ccgttaag 38

<210> SEQ ID NO 120
<211> LENGTH: 36
<212> TYPE: DNA
<213> ORGANISM: Artificial Sequence
<220> FEATURE:
<223> OTHER INFORMATION: primer

<400> SEQUENCE: 120
atacgtagcg aattccggcc agtgaattgt aatacg 36

<210> SEQ ID NO 121
<211> LENGTH: 49
<212> TYPE: DNA
<213> ORGANISM: Artificial Sequence
<220> FEATURE:
<223> OTHER INFORMATION: primer

<400> SEQUENCE: 121
gatcggcatg aattctgttt tattgatata gtgtttaagc gaatgacag 49

<210> SEQ ID NO 122
<211> LENGTH: 24
<212> TYPE: DNA
<213> ORGANISM: Artificial Sequence
<220> FEATURE:
<223> OTHER INFORMATION: primer

<400> SEQUENCE: 122
gaagaggatt acaattgagt ccac 24

<210> SEQ ID NO 123
<211> LENGTH: 34
<212> TYPE: DNA
<213> ORGANISM: Artificial Sequence
<220> FEATURE:
<223> OTHER INFORMATION: primer

<400> SEQUENCE: 123
gggccccccc tcgaggaaat gcatgcagtg gcag 34

<210> SEQ ID NO 124
<211> LENGTH: 39
<212> TYPE: DNA
<213> ORGANISM: Artificial Sequence
<220> FEATURE:
<223> OTHER INFORMATION: primer

<400> SEQUENCE: 124
tcttgtgaca gaattcgcca ataagttaca ggggatctc 39

<210> SEQ ID NO 125
<211> LENGTH: 31
<212> TYPE: DNA
<213> ORGANISM: Artificial Sequence
<220> FEATURE:
<223> OTHER INFORMATION: primer

<400> SEQUENCE: 125
tggcgaattc tgtcacaaga cgctgctatt g 31

<210> SEQ ID NO 126
<211> LENGTH: 43
<212> TYPE: DNA
<213> ORGANISM: Artificial Sequence
<220> FEATURE:
<223> OTHER INFORMATION: primer

<400> SEQUENCE: 126
ggcggccgct ctagagcttc ataccaaatc ttctgatgaa atc 43

<210> SEQ ID NO 127
<211> LENGTH: 36
<212> TYPE: DNA
<213> ORGANISM: Artificial Sequence
<220> FEATURE:
<223> OTHER INFORMATION: primer

<400> SEQUENCE: 127
cttattggcg aattccggcc agtgaattgt aatacg 36

<210> SEQ ID NO 128
<211> LENGTH: 49
<212> TYPE: DNA
<213> ORGANISM: Artificial Sequence
<220> FEATURE:
<223> OTHER INFORMATION: primer

<400> SEQUENCE: 128
cttgtgacag aattctgttt tattgatata gtgtttaagc gaatgacag 49

<210> SEQ ID NO 129
<211> LENGTH: 22
<212> TYPE: DNA
<213> ORGANISM: Artificial Sequence
<220> FEATURE:
<223> OTHER INFORMATION: primer

<400> SEQUENCE: 129
ggtagcaaga gactaaagta cc 22

<210> SEQ ID NO 130
<211> LENGTH: 35
<212> TYPE: DNA
<213> ORGANISM: Artificial Sequence
<220> FEATURE:
<223> OTHER INFORMATION: primer

<400> SEQUENCE: 130
gggccccccc tcgagggaag tacttgggag ctttc 35

<210> SEQ ID NO 131
<211> LENGTH: 41
<212> TYPE: DNA
<213> ORGANISM: Artificial Sequence
<220> FEATURE:
<223> OTHER INFORMATION: primer

<400> SEQUENCE: 131
tgatggacat gaattcggta aacgaggagt ctttcaatat c 41

<210> SEQ ID NO 132
<211> LENGTH: 32
<212> TYPE: DNA
<213> ORGANISM: Artificial Sequence
<220> FEATURE:
<223> OTHER INFORMATION: primer

<400> SEQUENCE: 132
taccgaattc atgtccatca cgaaggtaca tg 32

<210> SEQ ID NO 133
<211> LENGTH: 37
<212> TYPE: DNA
<213> ORGANISM: Artificial Sequence
<220> FEATURE:
<223> OTHER INFORMATION: primer

<400> SEQUENCE: 133
ggcggccgct ctagaggtta cacataagtc ggacttg 37

<210> SEQ ID NO 134
<211> LENGTH: 36
<212> TYPE: DNA
<213> ORGANISM: Artificial Sequence
<220> FEATURE:
<223> OTHER INFORMATION: primer

<400> SEQUENCE: 134
tcgtttaccg aattccggcc agtgaattgt aatacg 36

<210> SEQ ID NO 135
<211> LENGTH: 49
<212> TYPE: DNA
<213> ORGANISM: Artificial Sequence
<220> FEATURE:
<223> OTHER INFORMATION: primer

<400> SEQUENCE: 135
gatggacatg aattctgttt tattgatata gtgtttaagc gaatgacag 49

<210> SEQ ID NO 136
<211> LENGTH: 22
<212> TYPE: DNA
<213> ORGANISM: Artificial Sequence
<220> FEATURE:
<223> OTHER INFORMATION: primer

<400> SEQUENCE: 136
cttcaaatga tggtaaacct cc 22

<210> SEQ ID NO 137
<211> LENGTH: 34
<212> TYPE: DNA
<213> ORGANISM: Artificial Sequence
<220> FEATURE:
<223> OTHER INFORMATION: primer

<400> SEQUENCE: 137
gggccccccc tcgaggagaa aagctgcccc attg 34

<210> SEQ ID NO 138
<211> LENGTH: 42
<212> TYPE: DNA
<213> ORGANISM: Artificial Sequence
<220> FEATURE:
<223> OTHER INFORMATION: primer

<400> SEQUENCE: 138
aggcagacat gaattcgcaa cgcatttttt ctattggata ac 42

<210> SEQ ID NO 139

<211> LENGTH: 35
<212> TYPE: DNA
<213> ORGANISM: Artificial Sequence
<220> FEATURE:
<223> OTHER INFORMATION: primer

<400> SEQUENCE: 139
ttgcgaattc atgtctgcct ttgttactaa agctg 35

<210> SEQ ID NO 140
<211> LENGTH: 35
<212> TYPE: DNA
<213> ORGANISM: Artificial Sequence
<220> FEATURE:
<223> OTHER INFORMATION: primer

<400> SEQUENCE: 140
ggcggccgct ctagagcaga agcccgattt tagtc 35

<210> SEQ ID NO 141
<211> LENGTH: 36
<212> TYPE: DNA
<213> ORGANISM: Artificial Sequence
<220> FEATURE:
<223> OTHER INFORMATION: primer

<400> SEQUENCE: 141
atgcgttgcg aattccggcc agtgaattgt aatacg 36

<210> SEQ ID NO 142
<211> LENGTH: 49
<212> TYPE: DNA
<213> ORGANISM: Artificial Sequence
<220> FEATURE:
<223> OTHER INFORMATION: primer

<400> SEQUENCE: 142
ggcagacatg aattctgttt tattgatata gtgtttaagc gaatgacag 49

<210> SEQ ID NO 143
<211> LENGTH: 21
<212> TYPE: DNA
<213> ORGANISM: Artificial Sequence
<220> FEATURE:
<223> OTHER INFORMATION: primer

<400> SEQUENCE: 143
cgttggtaag tttctgctac c 21

<210> SEQ ID NO 144
<211> LENGTH: 35
<212> TYPE: DNA
<213> ORGANISM: Artificial Sequence
<220> FEATURE:
<223> OTHER INFORMATION: primer

<400> SEQUENCE: 144
gggccccccc tcgagggatc ttacacagga cgaac 35

<210> SEQ ID NO 145
<211> LENGTH: 36
<212> TYPE: DNA
<213> ORGANISM: Artificial Sequence
<220> FEATURE:
<223> OTHER INFORMATION: primer

<400> SEQUENCE: 145
gcgacgacat gaattcgtgc tactgctatc actgtc 36

<210> SEQ ID NO 146
<211> LENGTH: 33
<212> TYPE: DNA
<213> ORGANISM: Artificial Sequence
<220> FEATURE:
<223> OTHER INFORMATION: primer

<400> SEQUENCE: 146
gcacgaattc atgtcgtcgc ttatttcaaa aac 33

<210> SEQ ID NO 147
<211> LENGTH: 45
<212> TYPE: DNA
<213> ORGANISM: Artificial Sequence
<220> FEATURE:
<223> OTHER INFORMATION: primer

<400> SEQUENCE: 147
ggcggccgct ctagagatgt agtaggatca tggattctaa aaaag 45

<210> SEQ ID NO 148
<211> LENGTH: 36
<212> TYPE: DNA
<213> ORGANISM: Artificial Sequence
<220> FEATURE:
<223> OTHER INFORMATION: primer

<400> SEQUENCE: 148
cagtagcacg aattccggcc agtgaattgt aatacg 36

<210> SEQ ID NO 149
<211> LENGTH: 49
<212> TYPE: DNA
<213> ORGANISM: Artificial Sequence
<220> FEATURE:
<223> OTHER INFORMATION: primer

<400> SEQUENCE: 149
cgacgacatg aattctgttt tattgatata gtgtttaagc gaatgacag 49

<210> SEQ ID NO 150
<211> LENGTH: 25
<212> TYPE: DNA
<213> ORGANISM: Artificial Sequence
<220> FEATURE:
<223> OTHER INFORMATION: primer

<400> SEQUENCE: 150
cctttatcag gtccttgtga attag 25

<210> SEQ ID NO 151
<211> LENGTH: 43
<212> TYPE: DNA
<213> ORGANISM: Artificial Sequence
<220> FEATURE:
<223> OTHER INFORMATION: primer

<400> SEQUENCE: 151
gggccccccc tcgaggcctt agttgtaagt aattaaccaa tcc 43

<210> SEQ ID NO 152
<211> LENGTH: 42
<212> TYPE: DNA

<213> ORGANISM: Artificial Sequence
<220> FEATURE:
<223> OTHER INFORMATION: primer

<400> SEQUENCE: 152
gattggacat gtcgacggat ttcggtcttt tctaaccatt tc 42

<210> SEQ ID NO 153
<211> LENGTH: 38
<212> TYPE: DNA
<213> ORGANISM: Artificial Sequence
<220> FEATURE:
<223> OTHER INFORMATION: primer

<400> SEQUENCE: 153
atccgtcgac atgtccaatc tattaaacaa gtttgctg 38

<210> SEQ ID NO 154
<211> LENGTH: 39
<212> TYPE: DNA
<213> ORGANISM: Artificial Sequence
<220> FEATURE:
<223> OTHER INFORMATION: primer

<400> SEQUENCE: 154
ggcggccgct ctagagtttc gcggtaagtt tgggtataa 39

<210> SEQ ID NO 155
<211> LENGTH: 36
<212> TYPE: DNA
<213> ORGANISM: Artificial Sequence
<220> FEATURE:
<223> OTHER INFORMATION: primer

<400> SEQUENCE: 155
ccgaaatccg tcgaccggcc agtgaattgt aatacg 36

<210> SEQ ID NO 156
<211> LENGTH: 49
<212> TYPE: DNA
<213> ORGANISM: Artificial Sequence
<220> FEATURE:
<223> OTHER INFORMATION: primer

<400> SEQUENCE: 156
attggacatg tcgactgttt tattgatata gtgtttaagc gaatgacag 49

<210> SEQ ID NO 157
<211> LENGTH: 20
<212> TYPE: DNA
<213> ORGANISM: Artificial Sequence
<220> FEATURE:
<223> OTHER INFORMATION: primer

<400> SEQUENCE: 157
gtttgggtat aagtgccacc 20

<210> SEQ ID NO 158
<211> LENGTH: 37
<212> TYPE: DNA
<213> ORGANISM: Artificial Sequence
<220> FEATURE:
<223> OTHER INFORMATION: primer

<400> SEQUENCE: 158
gggccccccc tcgagggaaa ccatatcctc ctagtgg 37

<210> SEQ ID NO 159
<211> LENGTH: 36
<212> TYPE: DNA
<213> ORGANISM: Artificial Sequence
<220> FEATURE:
<223> OTHER INFORMATION: primer

<400> SEQUENCE: 159
catcggtcat gaattcgctc tccggtagat cctaac 36

<210> SEQ ID NO 160
<211> LENGTH: 30
<212> TYPE: DNA
<213> ORGANISM: Artificial Sequence
<220> FEATURE:
<223> OTHER INFORMATION: primer

<400> SEQUENCE: 160
gagcgaattc atgaccgatg tgttgagaag 30

<210> SEQ ID NO 161
<211> LENGTH: 38
<212> TYPE: DNA
<213> ORGANISM: Artificial Sequence
<220> FEATURE:
<223> OTHER INFORMATION: primer

<400> SEQUENCE: 161
ggcggccgct ctagaggcaa cttttccatc tgttttac 38

<210> SEQ ID NO 162
<211> LENGTH: 36
<212> TYPE: DNA
<213> ORGANISM: Artificial Sequence
<220> FEATURE:
<223> OTHER INFORMATION: primer

<400> SEQUENCE: 162
cagtagcacg aattccggcc agtgaattgt aatacg 36

<210> SEQ ID NO 163
<211> LENGTH: 49
<212> TYPE: DNA
<213> ORGANISM: Artificial Sequence
<220> FEATURE:
<223> OTHER INFORMATION: primer

<400> SEQUENCE: 163
cgacgacatg aattctgttt tattgatata gtgtttaagc gaatgacag 49

<210> SEQ ID NO 164
<211> LENGTH: 27
<212> TYPE: DNA
<213> ORGANISM: Artificial Sequence
<220> FEATURE:
<223> OTHER INFORMATION: primer

<400> SEQUENCE: 164
cccgtttatg aactaaacct atgttag 27

<210> SEQ ID NO 165
<211> LENGTH: 34
<212> TYPE: DNA
<213> ORGANISM: Artificial Sequence
<220> FEATURE:

<223> OTHER INFORMATION: primer

<400> SEQUENCE: 165
gggccccccc tcgagccatt ggaagccttg caac 34

<210> SEQ ID NO 166
<211> LENGTH: 41
<212> TYPE: DNA
<213> ORGANISM: Artificial Sequence
<220> FEATURE:
<223> OTHER INFORMATION: primer

<400> SEQUENCE: 166
cctcagacat gaattccgat ttcggtacga agttttctta c 41

<210> SEQ ID NO 167
<211> LENGTH: 30
<212> TYPE: DNA
<213> ORGANISM: Artificial Sequence
<220> FEATURE:
<223> OTHER INFORMATION: primer

<400> SEQUENCE: 167
atcggaattc atgtctgagg cttttggacc 30

<210> SEQ ID NO 168
<211> LENGTH: 35
<212> TYPE: DNA
<213> ORGANISM: Artificial Sequence
<220> FEATURE:
<223> OTHER INFORMATION: primer

<400> SEQUENCE: 168
ggcggccgct ctagaagaaa ttggcactct tcccc 35

<210> SEQ ID NO 169
<211> LENGTH: 36
<212> TYPE: DNA
<213> ORGANISM: Artificial Sequence
<220> FEATURE:
<223> OTHER INFORMATION: primer

<400> SEQUENCE: 169
ccgaaatcgg aattccggcc agtgaattgt aatacg 36

<210> SEQ ID NO 170
<211> LENGTH: 49
<212> TYPE: DNA
<213> ORGANISM: Artificial Sequence
<220> FEATURE:
<223> OTHER INFORMATION: primer

<400> SEQUENCE: 170
ctcagacatg aattctgttt tattgatata gtgtttaagc gaatgacag 49

<210> SEQ ID NO 171
<211> LENGTH: 21
<212> TYPE: DNA
<213> ORGANISM: Artificial Sequence
<220> FEATURE:
<223> OTHER INFORMATION: primer

<400> SEQUENCE: 171
gcagttttct tgatgccatc c 21

YEAST CELL HAVING ACID TOLERANCE, METHOD OF PREPARING YEAST CELL AND USE THEREOF

CROSS-REFERENCE TO RELATED APPLICATION

This application claims the benefit of Korean Patent Application No. 10-2015-0066250, filed on May 12, 2015, in the Korean Intellectual Property Office, the disclosure of which is incorporated herein in its entirety by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 191,172 byte ASCII (Text) file named "722485_ST25.TXT" created Mar. 23, 2016.

BACKGROUND

1. Field

The present disclosure relates to a genetically engineered yeast cell having acid tolerance, a method of preparing the same, and use thereof.

2. Description of the Related Art

Organic acids are widely used in a variety of industries. For example, lactate is an organic acid widely used in a variety of industrial fields, including food, pharmaceutical, chemical, and electronic industries. Lactate is a colorless, odorless, water-soluble, low-volatility material. Lactate is also not toxic to the human body, and is used as a flavoring agent, a sour taste agent, a preserving agent, or the like. Additionally, lactate is used as a source of polylactic acid (PLA) that is an environmentally friendly, biodegradable plastic known as an alternate polymeric material.

Organic acids are dissociated into hydrogen ions and their own negative ions at a higher pH than their own pKa value, for example, under neutral conditions. However, an organic acid, for example, lactic acid, is present in the form of a free acid without an electromagnetic force under acidic conditions lower than its own pKa value. The negative ion may not permeate a cell membrane, but the free acid form may permeate a cell membrane. Therefore, the free acid form may flow into the cells from extracellular environments where the concentration of the organic acid is high, thus lowering an intercellular pH level. Further, there is a disadvantage that an organic acid present as negative ions is isolated in the form of salt by an isolation process involving the addition of a salt. As a result, cells lacking acid-tolerance may become inactive and nonviable under acidic environments containing lactic acid Accordingly, there is a need for microorganisms with acid-tolerance.

SUMMARY

Provided herein is a genetically engineered, acid tolerant yeast cell comprising a genetic modification that increases the activity of SUL1, STR3, HXT7, ERR1, GRX8, MXR1, GRE1, MRK1, AAD10, or a combination thereof; a method of preparing said yeast cell; and a method of producing lactate comprising culturing said yeast cell.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1A:
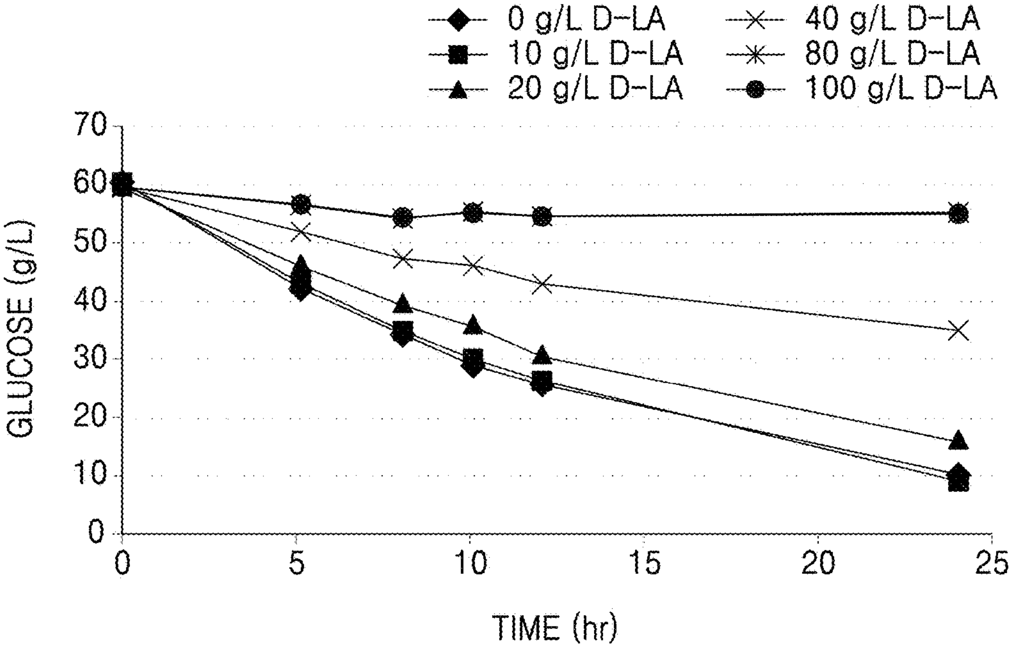
FIG. 1A shows glucose concentration over time in yeast culture spiked with 0, 10, 20, 40, 80, or 100 g/L D-lactic acid.

The term "increase in activity" or "increased activity", as used herein, may refer to a detectable increase in an activity of a cell, a protein, or an enzyme. The "increase in activity" or "increased activity" may also refer to an activity level of a modified (e.g., genetically engineered) cell, protein, or enzyme that is higher than that of a comparative cell, protein, or enzyme of the same type, such as a cell, protein, or enzyme that does not have a given genetic modification (e.g., original or "wild-type" cell, protein, or enzyme). "Cell activity" may refer to an activity of a particular protein or enzyme of a cell. For example, an activity of a modified or engineered cell, protein, or enzyme may be increased by about 5% or more, about 10% or more, about 15% or more, about 20% or more, about 30% or more, about 50% or more, about 60% or more, about 70% or more, or about 100% or more than an activity of a non-engineered cell, protein, or enzyme of the same type, i.e., a wild-type cell, protein, or enzyme. An activity of a particular protein or enzyme in a cell may be increased by about 5% or more, about 10% or more, about 15% or more, about 20% or more, about 30% or more, about 50% or more, about 60% or more, about 70% or more, or about 100% or more than an activity of the same protein or enzyme in a parent cell, e.g., a non-engineered cell or cell not having a particular genetic modification. A cell having an increased activity of a protein or an enzyme may be identified by using any method known in the art. The cell having the increased activity may have one or more genetic modifications for increasing the activity of the enzyme or polypeptide, compared to a cell lacking the one or more genetic modifications.

The term "genetic modification" means an artificial alteration in a constitution or structure (e.g., nucleotide sequence) of a genetic material of a cell. Genetic modifications include introducing a polynucleotide encoding a polypeptide into a cell (e.g., an increase in a copy number of the gene); a substitution, addition, insertion, or deletion of one or more nucleotides with respect to a genetic material of a parent cell; or a chemical modification of the genetic material of a parent cell. Such genetic modifications can include modification of coding regions and functional fragments thereof for heterologous, homologous, or both heterologous and homologous polypeptides for the referenced species. In addition, the genetic modifications can include modifications of non-coding regulatory regions, which alter the expression of a gene or an operon. The non-coding regions include a 5'-non coding sequence and/or a 3'-non coding sequence.

The "increase in the copy number" may be caused by introduction or amplification of a gene, and may be achieved by genetically engineering a cell so that the cell is allowed to have a gene that does not exist in a non-engineered cell, or an increased number of copies of a gene as compared to a non-engineered cell. The introduction of the gene may be mediated by a vehicle such as a vector. The introduction may be a transient introduction in which the gene is not integrated into a genome, or an integration of the gene into the genome. The introduction may be performed, for example, by introducing a vector into the cell, in which the vector includes a polynucleotide encoding a target polypeptide, and then, replicating the vector in the cell, or by integrating the polynucleotide into the genome.

The term "gene" refers to a nucleic acid fragment capable of producing an expression product, for example, mRNA or protein, by any one of transcription and translation, and may include a coding region as well as regulatory sequences such as a 5' non-coding sequence or a 3' non-coding sequence. Thus, the term "gene" as used herein encompasses DNA as well as RNA (e.g., genomic DNA, mRNA, etc.). As used herein, gene names will be displayed in lower case letters when referring to nucleic acid sequences (e.g., DNA, mRNA, etc.) and in upper case letters when referring to the protein products thereof (e.g., enzymes), as is standard practice in the art.

The term "cell", "strain", or "microorganism" may be used interchangeably and may include a yeast, a bacterium, or a fungus.

The term "decrease in activity" or "decreased activity", as used herein, means that a cell has an activity of an enzyme or a polypeptide that is lower than the activity level in a parent cell without a particular genetic modification (e.g., a non-genetically engineered cell). Also, the "decrease in activity" or "decreased activity" means that an isolated enzyme or a polypeptide has an activity lower than that of an original or a wild-type enzyme or polypeptide. The decrease in activity or decreased activity encompasses no activity. For example, a modified (e.g., genetically engineered) cell or enzyme may have enzymatic activity of converting a substrate to a product, that is decreased by about 20% or more, about 30% or more, about 40% or more, about 50% or more, about 55% or more, about 60% or more, about 70% or more, about 75% or more, about 80% or more, about 85% or more, about 90% or more, about 95% or more, or about 100%, as compared to that of a cell or enzyme that does not have the modification, i.e., a parent cell or a "wild-type" cell or enzyme. Decreased activity of an enzyme or a cell may be confirmed by any methods known in the art. The decrease in activity includes the case that an enzyme has no activity or decreased activity even though the enzyme is expressed, or the case that an enzyme-encoding gene is not expressed or expressed at a low level, compared to a cell having a non-modified gene, i.e., a parent cell or a wild-type cell.

The term "parent cell" refers to an original cell, for example, a non-genetically engineered cell of the same type as an engineered yeast cell. With respect to a particular genetic modification, the "parent cell" may be a cell that lacks the particular genetic modification, but is identical in all other respects. Thus, the parent cell may be a cell that is used as a starting material to produce a genetically engineered yeast cell having increased or decreased activity of a given protein, or increased or decreased production of a given product. Since the parent cell may be identical to a genetically modified cell in all respects except for the particular genetic modification, the parent cell may be useful as a reference cell for determining the affects of the genetic modification on a particular function, activity, phenotype, etc.

The term "wild-type" polypeptide or polynucleotide may be a polypeptide or polynucleotide having no particular genetic modification, and the genetic modification is to obtain a genetically engineered polypeptide or polynucleotide.

The term "disruption", as used herein, refers to a genetic modification to reduce expression of a referenced gene. The disruption includes a genetic manipulation whereby the referenced gene is not expressed (hereinafter, referred to as "inactivation" of a gene) or a genetic manipulation whereby the gene is expressed at a reduced level (hereinafter, referred to as "attenuation" of a gene). Disruption also encompasses inactivation by which no expression of a gene product occurs, or expression of only a non-functional product occurs. Disruption also encompasses attenuation by which the expression level of a functional product of a gene is reduced, but not necessarily eliminated. That is, attenuation includes a reduction in the expression level of the functional product even though the entire expression of the gene might not be reduced, or might even be increased. Herein, the functional product of a gene refers to a product retaining a biochemical or physiological function (e.g., enzymatic activity) of the product (e.g., enzyme) of the gene of a parent cell or a wild-type cell. Thus, disruption includes functional disruption of the gene.

The disruption of a gene may be achieved by any suitable genetic manipulation such as homologous recombination, directed mutagenesis, or molecular evolution. If a cell includes a plurality of the same genes, or two or more different paralogs of a gene, one or more of the genes may be disrupted. For example, the genetic modification may be performed by transforming the cell with a vector containing a partial sequence of the gene, culturing the cell so that the gene is disrupted by homogonous recombination of the sequence with an endogenous gene of the cell, and then selecting cells, in which the homologous recombination occurred, using a selection marker.

The term "sequence identity" of a polypeptide or a polynucleotide, as used herein, refers to a degree of identity between amino acid residues or bases of sequences obtained after the sequences are aligned so as to best match in certain comparable regions. The sequence identity is a value that is measured by comparing two sequences in certain comparable regions via optimal alignment of the two sequences, in which portions of the sequences in the certain comparable regions may be added or deleted compared to reference sequences. A percentage of sequence identity may be calculated by, for example, comparing two optimally aligned sequences in the entire comparable regions, determining the number of locations in which the same amino acids or nucleic acids appear to obtain the number of matching locations, dividing the number of matching locations by the total number of locations in the comparable regions (that is, the size of a range), and multiplying a result of the division by 100 to obtain the percentage of the sequence identity. The percentage of the sequence identity may be determined using a known sequence comparison program, for example, BLASTN or BLASTP (NCBI), CLC Main Workbench (CLC bio) and MegAlign™ (DNASTAR Inc).

Various levels of sequence identity may be used to identify various types of polypeptides or polynucleotides having the same or similar functions or activities. For example, the sequence identity may include a sequence identity of about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, about 99% or more, or 100%.

As used herein, the term "exogenous" means that a referenced molecule or a referenced activity is artificially introduced into a host cell. A molecule may be introduced, for example, by introducing a coding nucleic acid into a genetic material of the host, such as integration into a host chromosome, or as a non-chromosomal genetic material such as a plasmid. The term "exogenous", when used in reference to expression of a coding nucleic acid, refers to introduction of the coding nucleic acid in an expressible form into an individual. The term "exogenous", when used in reference to biosynthetic activity, refers to activity that is introduced into a host parent cell. The source may be, for example, a homologous or heterologous coding nucleic acid that expresses the referenced activity following introduction into the host parent cell. Therefore, the term "endogenous" refers to a referenced molecule or activity that is present in the host cell before genetic manipulation. Similarly, the term "endogenous", when used in reference to expression of a coding nucleic acid, refers to expression of a coding nucleic acid contained within an individual before genetic manipulation. The term "heterologous" refers to a molecule or activity derived from a source other than the referenced species, whereas "homologous" refers to a molecule or activity derived from the referenced species (e.g., the species of the host cell itself). Accordingly, exogenous expression of a coding nucleic acid may utilize either or both of heterologous and homologous coding nucleic acids.

The term "genetic engineering" or "genetically engineered", as used herein, refers to action of introducing one or more genetic modifications into a cell or a cell produced thereby.

The term "lactate", as used herein, includes "lactic acid" itself as well as a negative ion, a salt, solvate, or polymorph thereof, or a combination thereof. The salt may be, for example, an inorganic acid salt, an organic acid salt, or a metal salt. The inorganic acid salt may be hydrochloride, bromate, phosphate, sulfate or disulfate. The organic acid salt may be formate, acetate, propionate, lactate, oxalate, tartrate, malate, maleate, citrate, fumarate, besylate, camsylate, edisilate, trifluoroacetate, benzoate, gluconate, methanesulfonate, glycolate, succinate, 4-toluenesulfonate, galacturonate, embonate, glutamate or aspartate. The metal salt may be a calcium salt, a sodium salt, a magnesium salt, a strontium salt or a potassium salt.

An aspect provides a yeast cell that is engineered to overcome a lactate production-inhibitory effect by lactate by increasing activity of a gene of which expression is specifically inhibited by lactate. The yeast cell may have one or more properties selected from the group consisting of increased acid tolerance, increased yeast cell growth, and increased sugar consumption.

An aspect provides a genetically engineered yeast cell that has increased activities of expression products of one or more genes selected from the group consisting of SUL1, STR3, AAD10, MXR1, GRX8, MRK1, GRE1, HXT7, and ERR1, compared to a parent cell. The genetically engineered yeast cell also demonstrates increased acid tolerance and/or increased glucose consumption, as compared to a parent cell.

Expression levels of the aforementioned genes are decreased in parent yeast cells cultured in the presence of lactate, compared to those cultured in the absence of lactate, as shown in Table 1.

TABLE 1

| Classification | Name | Genebank | Fold Reduction* | Putative function |
|---|---|---|---|---|
| Sulfur assimilation | SUL1 | YBR294W | 2.22 | Sulfate transport |
| L-cysteine biosynthesis | STR3 | YGL184C | 7.60 | Methionine biosynthesis process |
| Central metabolism | HXT7 | YDR342C | 2.38 | Hexose transport |
| Central metabolism | ERR1 | YOR393W | 3.04 | Unknown |
| Oxidative stress | GRX8 | YLR364W | 1.65 | Glutathione-disulfide reductase activity |
| Oxidative stress | MXR1 | YER042W | 1.57 | Cellular response to oxidative stress |
| Tolerance | GRE1 | YPL223C | 1.83 | Unknown |
| Tolerance | MRK1 | YDL079C | 1.99 | Protein degradation |
| Other | AAD10 | YJR155W | 2.56 | Aldehyde metabolism |

*Fold Reduction represents the decrease in gene expression levels in *Saccharomyces cerevisiae* cultured in the presence of 20 g/L of lactate for 5 hours under microaerobic conditions as in Example 1, relative to a control group cultured in the absence of lactate (see Example 1).

The genetically engineered yeast cell may include a genetic modification for increasing the activity of SUL1, STR3, AAD10, MXR1, GRX8, MRK1, GRE1, HTX7, ERR1, or a combination thereof.

The SUL1 protein may be sulfate permease 1. The SUL1 protein may be also referred to as SFP2. The SUL1 protein may be high-affinity sulfate transporter 1. The SUL1 protein may be classified as TCDB (Transporter Classification Database) 2.A.53.1.1. The SUL1 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 1. The SUL1 protein may have, for example, an NCBI reference sequence of NP_009853.3. A gene encoding the SUL1 protein may be a gene having a sequence identity of about 95% or higher with a polynucleotide sequence of SEQ ID NO: 2. The sul1 gene may have, for example, an NCBI reference sequence of NM_001178642.3.

The STR3 protein may be cystathionine beta-lyase (CBL). The STR3 protein may be classified as EC 4.4.1.8. The STR3 protein may be also referred to as beta-cystathionase, cysteine lyase, or sulfur transfer protein 3. The STR3 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 3. The STR3 protein may have, for example, an NCBI reference sequence of NP_011331.3. A gene encoding the STR3 protein may be a gene having a sequence identity of about 95% or higher with a polynucleotide sequence of SEQ ID NO: 4. The str3 gene may have, for example, an NCBI reference sequence of NM_001181049.3.

The HXT7 protein may be high-affinity hexose transporter (HXT6). The HXT7 protein may be classified as TCDB 2.A.1.1.31. The HXT7 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 5. The HXT7 protein may have, for example, an NCBI reference sequence of NP_010629.3. A gene encoding the HXT7 protein may be a gene having a sequence identity of about 95% or higher with a polynucleotide sequence of SEQ ID NO: 6. The hxt7 gene may have, for example, an NCBI reference sequence of NM_001180650.3.

The ERR1 protein may be enolase-related protein 1. The ERR1 protein may be also referred to as 2-phospho-D-glycerate hydro-lyase or 2-phosphoglycerate dehydratase. The ERR1 protein may be classified as EC 4.2.1.11. The ERR1 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 7. The ERR1 protein may have, for example, an NCBI reference sequence of NP_015038.1. A gene encoding the ERR1 protein may be a gene having a sequence identity of about 95% or higher with a polynucleotide sequence of SEQ ID NO: 8. The err1 gene may have, for example, an NCBI reference sequence of NM_001183813.1.

The GRX8 protein may be glutaredoxin-8. The GRX8 protein may be also referred to as glutathione-dependent oxidoreductase 8. The GRX8 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 9. The GRX8 protein may have, for example, an NCBI reference sequence of NP_013468.3. A gene encoding the GRX8 protein may be a gene having a sequence identity of about 95% or higher with a polynucleotide sequence of SEQ ID NO: 10. The grx8 gene may have, for example, an NCBI reference sequence of NM_001182253.3.

The MXR1 protein may be a peptide methionine sulfoxide reductase. The MXR1 protein may be classified as EC 1.8.4.11. The MXR1 protein may be also referred to as peptide-methionine (S)—S-oxide reductase, peptide Met(O) reductase, or protein-methionine-S-oxide reductase. The MXR1 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 11. The MXR1 protein may have, for example, an NCBI reference sequence of NP_010960.1. A gene encoding the MXR1 protein may be a gene having a sequence identity of about 95% or higher with a polynucleotide sequence of SEQ ID NO: 12. The mxr1 gene may have, for example, an NCBI reference sequence of NM_001178933.1.

The MRK1 protein may be serine/threonine-protein kinase (MRK1). The MRK1 protein may be classified as EC 2.7.11.1. The MRK1 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 13. The MRK1 protein may have, for example, an NCBI reference sequence of NP_010204.1. A gene encoding the MRK1 protein may be a gene having a sequence identity of about 95% or higher with a polynucleotide sequence of SEQ ID NO: 14. The mrk1 gene may have, for example, an NCBI reference sequence of NM_001180138.1.

The GRE1 protein may be protein GRE1. The GRE1 protein may be also referred to as hydrophilin. The GRE1 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 15. The GRE1 protein may have, for example, an NCBI reference sequence of NP_015101.1. A gene encoding the GRE1 protein may be a gene having a sequence identity of about 95% or higher with a polynucleotide sequence of SEQ ID NO: 16. The gre1 gene may have, for example, an NCBI reference sequence of NM_001184037.1.

The AAD10 protein may be putative aryl-alcohol dehydrogenase AAD10. The AAD10 protein may be classified as EC 1.1.1. The AAD10 protein may have an amino acid sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 17. The AAD10 protein may have, for example, an NCBI reference sequence of NP_012689.1. A gene encoding the AAD10 protein may be a gene having a sequence identity of about 95% or higher with a polynucleotide sequence of SEQ ID NO: 18. The aad10 gene may have, for example, an NCBI reference sequence of NM_001181813.1.

The genetically engineered yeast cell may comprise an increased amount of intracellular S-adenosyl methionine, compared to the parent cell. The genetically engineered yeast cell may have increased activity of sul1, str3, or a combination thereof, compared to the parent cell. The genetically engineered yeast cell may comprise an increased amount of intracellular methionine and/or cysteine, as compared to the parent cell.

The yeast cell may have a modification of an expression regulatory sequence of the gene encoding an above-referenced expression product. The expression regulatory sequence of the gene may be a promoter or terminator for expression of the gene. The expression regulatory sequence may be a sequence encoding a motif which may influence the expression of the gene. The motif may be, for example, a secondary structure-stabilizing motif, an RNA destabilizing motif, a splice-activating motif, a polyadenylation motif, an adenine-rich sequence, or an endonuclease recognition site.

The promoter may be an exogenous promoter that is operably linked to the gene encoding the expression product, for example, SUL1, STR3, HXT7, ERR1, GRX8, MXR1, GRE1, MRK1, or AAD10 gene. The promoter may be a constitutive promoter. The promoter may exhibit about 50%, 60%, 70%, 80%, 90%, 95%, or greater homology to a promoter that is native to a yeast gene and/or native to the host cell. The promoter may exhibit about 80%, 85%, 90%, or 95% homology to covalently linked Cell Wall protein 12 (CCW12), pyruvate decarboxylase (PDC) such as PDC1, phosphoglycerate kinase (PGK) such as PGK1, transcription elongation factor (TEF) such as TEF-1 and TEF-2, glyceraldehyde-3-phosphate dehydrogenase such as TDH1, TDH2, TDH3, or GPD1, triose phosphate isomerase (TPI1), purine-cytosine permease (PCPL3), alcohol dehydrogenase (ADH1), L-(+)-lactate-cytochrome c oxidoreductase (CYB) such as CYB2, xylose reductase (XR), xylitol dehydrogenase (XDH), CYC (cytochrome c), ADH, Histone H3 (e.g., HHT1 or HHT2) promoter, and a promoter derived from the gene selected from the group consisting of combinations thereof. The promoters of CYC (cytochrome c), TEF (transcription elongation factor), GPD, ADH, CCW12, and HHT2 genes may have a nucleotide sequence of SEQ ID NOS: 49, 50, 51, 52, 53, and 54, respectively.

The terminator may exhibit about 50%, 60%, 70%, 80%, 90%, 95%, or greater homology to a terminator that is native to a yeast gene and/or native to the host cell. The terminator may be selected from the group consisting of terminators of PGK1 (phosphoglycerate kinase 1), CYC1 (cytochrome c 1), GAL1 (galactokinase 1), and TPS1 (trehalose-6-phosphate synthase 1) genes. The CYC1 terminator may have a nucleotide sequence of SEQ ID NO: 55. The vector may further include a selection marker.

Further, the yeast cell may have an increase in the copy number of the gene encoding the expression product. The yeast cell may include an exogenous gene encoding the expression product. The exogenous gene may be properly regulated by an exogenous promoter operably linked to the gene. The promoter is the same as described above.

The term "acid-resistant (acid-tolerant, acid-tolerating)" and "acid-resistance (acid tolerance)" may be used interchangeably.

With respect to the genetically engineered yeast cell, acid tolerance means that its growth rate and/or viability under acidic conditions is better than that of a parent cell or non-engineered cell. The acidic conditions may be acidic conditions containing an organic acid, an inorganic acid, or a combination thereof. The organic acid may be a C1 to C20 organic acid. The organic acid may be acetic acid, lactic acid, propionic acid, 3-hydroxypropionic acid, butyric acid, 4-hydroxybutyric acid, succinic acid, fumaric acid, malic acid, oxalic acid, adipic acid, or a combination thereof. The genetically engineered yeast cell may grow well at pH 2.0 to 7.0 or less, for example, in the range of pH 2.0 to 6.5, pH 2.0 to 6.0, pH 2.0 to 5.5, pH 2.0 to 5.0, pH 2.0 to 4.5, pH 2.0 to 4.0, pH 2.0 to 3.8, pH 2.5 to 3.8, pH 3.0 to 3.8, pH 2.0 to 3.0, pH 2.0 to 2.7, pH 2.0 to 2.5, or pH 2.5 to 3.0, compared to the parent cell. The growth rate may be determined by counting colonies of the yeast cell or by measuring optical density (OD) of the colonies. For example, the genetically engineered yeast cell may have an increased optical density value under acidic conditions, compared to the parent cell.

Further, with respect to the genetically engineered yeast cell, acid tolerance means that its metabolization ability under acidic conditions is higher than that of a parent cell or non-engineered cell. The metabolization may refer to a chemical conversion in the yeast cell, for example, a reaction catalyzed by the yeast cell. The reaction catalyzed by the yeast cell allows that the yeast cell grows, proliferates and responds to external environments such as acidic conditions. The degree of metabolization ability may be measured as a nutrient consumption rate of a cell or a nutrient absorption rate of a cell, for example, a glucose absorption rate of a cell, or as a metabolite excretion rate of a cell, for example, a carbon dioxide excretion rate of a cell or a lactate production rate of a cell. The acidic conditions may be acidic conditions containing an organic acid, an inorganic acid, or a combination thereof. The organic acid may be a C1 to C20 organic acid. The organic acid may be acetic acid, lactic acid, propionic acid, 3-hydroxypropionic acid, butyric acid, 4-hydroxybutyric acid, succinic acid, fumaric acid, malic acid, oxalic acid, adipic acid, or a combination thereof. The genetically engineered yeast cell may metabolize well at pH 2.0 to 7.0 or less, for example, in the range of pH 2.0 to 6.5, pH 2.0 to 6.0, pH 2.0 to 5.5, pH 2.0 to 5.0, pH 2.0 to 4.5, pH 2.0 to 4.0, pH 2.0 to 3.8, pH 2.5 to 3.8, pH 3.0 to 3.8, pH 2.0 to 3.0, pH 2.0 to 2.7, pH 2.0 to 2.5, or pH 2.5 to 3.0, compared to the parent cell.

The yeast cell may belong to the genus *Saccharomyces, Kluyveromyces, Candida, Pichia, Issatchenkia, Debaryomyces, Zygosaccharomyces, Shizosaccharomyces*, or *Saccharomycopsis*. The genus *Saccharomyces* may be, for example, *Saccharomyces cerevisiae* (*S. cerevisiae*), *Saccharomyces bayanus* (*S. bayanus*), *Saccharomyces boulardii* (*S. boulardii*), *Saccharomyces bulderi* (*S. bulderi*), *Saccharomyces cariocanus* (*S. cariocanus*), *Saccharomyces cariocus* (*S. cariocus*), *Saccharomyces chevalieri* (*S. chevalieri*), *Saccharomyces dairenensis* (*S. dairenensis*), *Saccharomyces ellipsoideus* (*S. ellipsoideus*), *Saccharomyces eubayanus* (*S. eubayanus*), *Saccharomyces exiguus* (*S. exiguus*), *Saccharomyces florentinus* (*S. florentinus*), *Saccharomyces kluyveri* (*S. kluyveri*), *Saccharomyces martiniae* (*S. martiniae*), *Saccharomyces monacensis* (*S. monacensis*), *Saccharomyces norbensis* (*S. norbensis*), *Saccharomyces paradoxus* (*S. paradoxus*), *Saccharomyces pastorianus* (*S. pastorianus*), *Saccharomyces spencerorum* (*S. spencerorum*), *Saccharomyces turicensis* (*S. turicensis*), *Saccharomyces unisporus* (*S. unisporus*), *Saccharomyces uvarum* (*S. uvarum*), or *Saccharomyces zonatus* (*S zonatus*).

The yeast cell may have a lactate-producing ability. The yeast cell may have an activity of a polypeptide converting pyruvate into lactate. The yeast cell may include a gene encoding the polypeptide converting pyruvate into lactate. The gene may be an exogenous gene. The yeast cell may have the increased activity of the polypeptide converting pyruvate into lactate. The polypeptide converting pyruvate into lactate may be an enzyme that catalyzes conversion of pyruvate into lactate, and may be lactate dehydrogenase (LDH). The lactate dehydrogenase may be a NAD(P)-dependent enzyme. Further, the lactate dehydrogenase may be stereo-specific.

The gene encoding the lactate dehydrogenase may be derived from a bacterium, a yeast, a fungus, a mammal, or a reptile. The gene may be a polynucleotide encoding LDH derived from one or more selected from the group consisting of the genus *Lactobacillus* such as *L. delbrueckii* subsp. *bulgaicus* and *L. bulgaricus, L. johnsonii, L. plantarum, Pelodiscus sinensis japonicus, Ornithorhynchus anatinus, Tursiops truncatus, Rattus norvegicus, Xenopus laevis*, and *Bos Taurus*. The LDH is an enzyme producing D-lactate, which is classified as EC 1.1.1.28, or an enzyme producing L-lactate, which is classified as EC 1.1.1.27. The D-lactate dehydrogenase (D-LDH) may be an enzyme classified as EC 1.1.1.28. The D-LDH may be referred to as D-specific 2-hydroxyacid dehydrogenase. The D-LDH may be an enzyme that catalyzes conversion of pyruvate and NADH into (R)-lactate and $NAD^+$. The D-LDH may have a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 19. A gene encoding the D-LDH may have a sequence identity of about 60% or higher, about 70% or higher, about 80% or higher, about 90% or higher, about 95% or higher, about 96% or higher, about 97% or higher, about 98% or higher, or about 99% or higher with a polynucleotide sequence of SEQ ID NO: 20.

The L-lactate dehydrogenase (L-LDH) may be an enzyme classified as EC 1.1.1.27. The L-LDH may be referred to as L-specific 2-hydroxyacid dehydrogenase. The L-LDH may be an enzyme that catalyzes conversion of pyruvate and NADH into (S)-lactate and $NAD^+$. The L-LDH may have a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 21, 22, 23, 24, or 25. A gene encoding the L-LDH may have a sequence identity of about 60% or higher, about 70% or higher, about 80% or higher, about 90% or higher, about 95% or higher, about 96% or higher, about 97% or higher, about 98% or higher, or about 99% or higher with a polynucleotide sequence of SEQ ID NO: 26.

The gene encoding lactate dehydrogenase may be included in a vector. The vector may include a replication origin, a promoter, a polynucleotide encoding lactate dehydrogenase, and a terminator. The replication origin may include a yeast autonomous replication sequence (ARS). The yeast ARS may be stabilized by a yeast centrometric sequence (CEN). The promoter is the same as described above. The terminator is the same as described above. The polynucleotide encoding lactate dehydrogenase may be included in a particular locus of a genome of a yeast cell. When the polynucleotide encoding lactate dehydrogenase functions to produce an active protein in a cell, the polynucleotide is considered to be "functional" within the cell.

The yeast cell may include one copy of the lactate dehydrogenase-encoding polynucleotide or multiple copies of the lactate dehydrogenase-encoding polynucleotide, for example, 2 to 10 copies. The yeast cell may include, for example, 1 to 8, 1 to 7, 1 to 6, 1 to 5, 1 to 4, or 1 to 3 copies of the lactate dehydrogenase-encoding polynucleotide. If the yeast cell includes multiple lactate dehydrogenase-encoding polynucleotides, each of the polynucleotide may include copies of the same polynucleotide or copies of polynucleotides encoding two or more different lactate dehydrogenases. The multiple copies of the polynucleotide encoding exogenous lactate dehydrogenase may be included in the same locus or multiple loci in a genome of a host cell, and a promoter or terminator of each copy may be the same as or different from each other.

The yeast cell may further have a genetic modification that decreases an activity of a polypeptide converting pyruvate to acetaldehyde, a polypeptide converting dihydroxyacetone phosphate (DHAP) to glycerol-3-phosphate, a polypeptide converting acetaldehyde to ethanol, a polypeptide converting acetaldehyde to acetate or a combination thereof, compared to the parent cell.

The yeast cell may have a disruption of a gene encoding the polypeptide that converts pyruvate to acetaldehyde. The polypeptide that converts pyruvate to acetaldehyde may be an enzyme that catalyzes conversion of pyruvate to acetaldehyde and is classified as EC 4.1.1.1. The polypeptide that converts pyruvate to acetaldehyde may be, for example, pyruvate decarboxylase (PDC). PDC may be, for example, PDC1, PDC5, or PDC6. The polypeptide that converts pyruvate to acetaldehyde may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 27 or 29. The gene encoding the polypeptide that converts pyruvate to acetaldehyde may have a polynucleotide sequence encoding an amino acid sequence having a sequence identity of about 98% or higher with an amino acid sequence of SEQ ID NO: 5, or a polynucleotide sequence of SEQ ID NO: 28 or 30. The gene may be pdc1, pdc5, or pdc6.

The yeast cell may have a disruption of a gene encoding the polypeptide that converts dihydroxyacetone phosphate (DHAP) to glycerol-3-phosphate. The polypeptide may be classified as EC 1.1.1.8, EC 1.1.5.3, or EC 1.1.1.94. The polypeptide may be glycerol-3-phosphate dehydrogenase (GPD). GPD may be, for example, GPD1, GPD2, or GPD3. The yeast cell may have a disruption of a gene encoding GPD1, GPD2, GPD3, or a combination thereof. GPD1 may be cytosolic glycerol-3-phosphate dehydrogenase, and may be an enzyme that catalyzes reduction of DHAP to glycerol-3-phosphate using oxidation of NADH or NADP to $NAD^+$ or $NADP^+$. GPD2 may be glycerol-3-phosphate dehydrogenase (quinone). GPD3 may be glycerol-3-phosphate dehydrogenase ($NAD(P)^+$). GPD may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 31. A gene (gpd gene) encoding GPD may have a polynucleotide sequence encoding an amino acid sequence having a sequence identity of about 95% or higher with an amino acid sequence of SEQ ID NO: 9, or a polynucleotide sequence of SEQ ID NO: 32.

The yeast cell may have a disruption of a gene encoding the polypeptide that converts lactate to pyruvate. The polypeptide may be classified as EC. 1.1.2.4 or EC. 1.1.2.3.

The polypeptide classified as EC.1.1.2.4 may be D-lactate ferricytochrome C oxidoreductase. The D-lactate ferricytochrome C oxidoreductase may be also referred to as D-lactate dehydrogenase (DLD). The polypeptide may be DLD1, DLD2, or DLD3. The polypeptide may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 33. The gene encoding the polypeptide may have a polynucleotide sequence encoding an amino acid sequence having a sequence identity of about 95% or higher with the amino acid sequence of SEQ ID NO: 33. For example, the gene may have a polynucleotide sequence of SEQ ID NO: 34.

The polypeptide classified as EC. 1.1.2.3 may be L-lactate cytochrome-c oxidoreductase (CYB2), and also referred to as CYB2A or CYB2B. CYB2 may be a cytochrome c-dependent enzyme. CYB2 may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 35. The gene encoding the polypeptide that converts lactate to pyruvate may have a polynucleotide sequence encoding an amino acid sequence having a sequence identity of about 95% or higher with the amino acid sequence of SEQ ID NO: 7, or a polynucleotide sequence of SEQ ID NO: 36.

The yeast cell may have a disruption of a gene encoding the polypeptide that converts acetaldehyde to ethanol. The polypeptide may be an enzyme that catalyzes conversion of acetaldehyde to ethanol. The polypeptide may be classified as EC. 1.1.1.1. The polypeptide may be an enzyme that catalyzes conversion of acetaldehyde to ethanol using conversion of NADH to $NAD^+$. The polypeptide may be alcohol dehydrogenase (ADH). ADH may be, for example, Adh1, Adh2, Adh3, Adh4, Adh5, or Adh6. The polypeptide may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 37 or 39. The gene encoding the polypeptide may have a polynucleotide sequence encoding an amino acid sequence having a sequence identity of about 95% or higher with the amino acid sequence of SEQ ID NO: 16 or a polynucleotide sequence of SEQ ID NO: 38 or 40. The gene may be, for example, adh1, adh2, adh3, adh4, adh5, or adh6.

The yeast cell may have a disruption of a gene encoding the polypeptide that converts acetaldehyde to acetate. The polypeptide may be an enzyme that catalyzes conversion of acetaldehyde to acetate. The polypeptide may be classified as EC. 1.2.1.4. The polypeptide may be activated by $Mg^{2+}$ and specific to NADP. This enzyme may be involved in production of acetate. Cytosolic acetyl-CoA may be synthesized from the produced acetate. The polypeptide may be aldehyde dehydrogenase (ALD). ALD may be, for example, ALD6. The polypeptide may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 41. The gene encoding the polypeptide may have a polynucleotide sequence encoding an amino acid sequence having a sequence identity of about 95% or higher with the amino acid sequence of SEQ ID NO: 16 or a polynucleotide sequence of SEQ ID NO: 42. The gene may be, for example, ald6.

The yeast cell may further have an increased activity of an enzyme that catalyzes conversion of acetaldehyde to acetyl-CoA, compared to the parent cell.

The enzyme that catalyzes conversion of acetaldehyde to acetyl-CoA may be acylating acetaldehyde dehydrogenase (A-ALD) that is classified as EC. 1.2.1.10. One type of the enzyme that catalyzes conversion of acetaldehyde to acetyl-CoA may be a part of a bifunctional aldolase-dehydrogenase complex associated with 4-hydroxy-2-ketovalerate catabolism. The bifunctional enzyme catalyzes final two steps of a meta-cleavage pathway of catechol, which is an intermediate in various bacterial species in decomposition of phenol, toluene, naphthalene, biphenyl, and other aromatic compounds. First, 4-hydroxy-2-ketovalerate is converted to pyruvate and acetaldehyde by 4-hydroxy-2-ketovalerate aldolase, and then, acetaldehyde is converted to acetyl-CoA by A-ALD. The type of A-ALD may be, for example, DmpF of *Pseudomonas* sp. CF600 (Genbank No: CAA43226). MhpF protein of *Escherichia coli* is a homologue with respect to DmpF. Another type of the enzyme that catalyzes conversion of acetaldehyde to acetyl-CoA is a protein that catalyzes a reversible conversion between strictly or facultative anaerobic microorganism-derived acetyl-CoA and acetaldehyde, and does not have alcohol dehydrogenase activity. Examples of this type of protein may be found in *Clostridium kluyveri*. A-ALD is annotated to the genome of *Clostridium kluyveri* DSM 555 (Genbank No: EDK33116). Homologous protein AcdH was confirmed in the genome of *Lactobacillus plantarum* (Genbank No: NP_784141). Another example of this type of protein is the gene product of *Clostridium beijerinckii* NRRL B593. An example of A-ALD is *Escherichia coli*-derived MhpF or a functional homologue thereof, for example, *Escherichia coli* and *S. typhimurium*-derived EutE (for example, an EutE gene having a nucleotide sequence of SEQ ID NO: 44 and an EutE protein having an amino acid sequence of SEQ ID NO: 43), or *Pseudomonas* sp. CF600-derived dmpF. A-ALD may be $NAD(P)^+$ dependent. A-ALD may have an activity to catalyze the following reaction:

$$Acetaldehyde+CoA(coenzyme\ A)+NAD+\Leftrightarrow acetyl\text{-}CoA+NADH+H^+$$

A-ALD may be an A-ALD capable of being expressed without formation of a complex with other proteins. The yeast cell might not include, for example, an exogenous enzyme classified as EC 4.1.3.39 or a gene thereof.

The yeast cell may include an exogenous gene encoding an enzyme that catalyzes conversion of acetaldehyde to acetyl-CoA. The A-ALD exogenous gene may be expressed in the yeast cell in an amount sufficient to increase an activity of the enzyme catalyzing the conversion of acetaldehyde to acetyl-CoA, compared to the parent cell. The A-ALD exogenous gene may encode an amino acid sequence that has a sequence identity of 95% or more with an amino acid sequence of SEQ ID NO: 43. The A-ALD exogenous gene may have a sequence identity of about 95% or higher with a nucleotide sequence of SEQ ID NO: 44. SEQ ID NO: 44 is a nucleotide sequence of *Escherichia coli*-derived A-ALD gene.

The yeast cell may further have an increased activity of radiation sensitivity complementing kinase (RCK), compared to the parent cell. The radiation sensitivity complementing kinase may be serine/threonine-protein kinase. The kinase may be an enzyme classified as EC. 2.7.11.1. The radiation sensitivity complementing kinase may be RCK1 or RCK2. The radiation sensitivity complementing kinase may have an amino acid sequence having a sequence identity of about 60% or higher, about 70% or higher, about 80% or higher, about 90% or higher, about 95% or higher, about 96% or higher, about 97% or higher, about 98% or higher, or about 99% or higher with an amino acid sequence of SEQ ID NO: 45 or 47. For example, RCK1 and RCK2 may have an amino acid sequence of SEQ ID NOS: 45 and 47, respectively. The radiation sensitivity complementing kinase may have a polynucleotide sequence encoding a protein having a sequence identity of about 95% or higher with SEQ ID NO: 45 or 47 or a polynucleotide sequence of SEQ ID NO: 46 or SEQ ID NO: 48. For example, rck1 and rck2 genes may have a polynucleotide sequence of SEQ ID NOS: 46 and 48, respectively.

The yeast cell may be a yeast cell having an increased activity of SUL1, STR3, HXT7, ERR1, GRX8, MXR1, GRE1, MRK1, AAD10, or a combination thereof, compared to the parent cell; a disruption of a gene encoding a polypeptide that converts pyruvate to acetaldehyde, a gene encoding a polypeptide that converts lactate to pyruvate, a gene encoding a polypeptide that converts dihydroxyacetone phosphate (DHAP) to glycerol-3-phosphate, a gene encoding a polypeptide that converts pyruvate to D-lactate, a gene encoding a polypeptide that converts acetaldehyde to ethanol, a gene encoding a polypeptide that converts acetaldehyde to acetate, or a combination thereof; a gene encoding a polypeptide that converts pyruvate to lactate, a gene encoding a polypeptide that converts acetaldehyde to acetyl-CoA, and an increased activity of radiation sensitivity complementing kinase. The yeast cell may be *Saccharomyces cerevisiae.*

The yeast cell may have a decreased activity of a pathway of preventing a flow of a metabolite to lactate. Further, the yeast cell may have an increased activity of a pathway of facilitating or helping a flow of a metabolite to lactate.

Another aspect provides a method of preparing a yeast cell having acid tolerance, including overexpressing SUL1, STR3, HXT7, ERR1, GRX8, MXR1, GRE1, MRK1, AAD10, or a combination thereof in the yeast cell.

The method of preparing a yeast cell having acid tolerance may include overexpressing SUL1, STR3, HXT7, ERR1, GRX8, MXR1, GRE1, MRK1, AAD10, or a combination thereof in the yeast cell. In this regard, the "yeast cell", "SUL1", "STR3", "HXT7", "ERR1", "GRX8", "MXR1", "GRE1", "MRK1", and "AAD10" are the same as described above.

The overexpression of SUL1, STR3, HXT7, ERR1, GRX8, MXR1, GRE1, MRK1, AAD10, or a combination thereof may be overexpression of a gene encoding SUL1, STR3, HXT7, ERR1, GRX8, MXR1, GRE1, MRK1, AAD10, or a combination thereof. The overexpression means that the yeast cell overexpressing the gene produces SUL1, STR3, HXT7, ERR1, GRX8, MXR1, GRE1, MRK1, or AAD10 having the enzymatic activity at a higher or much higher normal level under the same conditions than its parent cell. The overexpression also means that the yeast cell produces mRNA encoding the protein at a higher or much higher normal level under the same conditions than its parent cell. Therefore, overexpression of the protein may be determined by measuring an inactivation level of the enzyme in the host cell using a suitable enzymatic analysis. The overexpressing may be performed to cause a genetic modification for increasing the activity.

Further, the method of preparing a yeast cell having acid tolerance may further include disrupting a gene encoding a polypeptide that converts pyruvate to acetaldehyde, a gene encoding a polypeptide that converts dihydroxyacetone phosphate (DHAP) to glycerol-3-phosphate, a gene encoding a polypeptide that converts lactate to pyruvate, a gene encoding a polypeptide that converts acetaldehyde to ethanol, a gene encoding a polypeptide that converts acetaldehyde to acetate, or combination thereof; introducing a gene encoding a polypeptide that converts acetaldehyde to acetyl-CoA; and overexpressing a gene encoding radiation sensitivity complementing kinase (RCK). In this regard, the gene encoding the polypeptide that converts pyruvate to acetaldehyde, the gene encoding the polypeptide that converts dihydroxyacetone phosphate (DHAP) to glycerol-3-phosphate, the gene encoding the polypeptide that converts lactate to pyruvate, the gene encoding the polypeptide that converts acetaldehyde to ethanol, the gene encoding the polypeptide that converts acetaldehyde to acetate, and the disruption are the same as described above. In this regard, the polypeptide that converts acetaldehyde to acetyl-CoA, and RCK are also the same as described above.

Still another aspect provides a method of producing lactate, including culturing the yeast cell so as to produce lactate. The yeast cell is the same as described above. The method of producing lactate may further include recovering lactate from the culture (e.g. from the culture medium). Recovery of lactate from the culture may be performed by isolation using a general method known in the art. Such isolation method may be centrifugation, filtration, ion chromatography, or crystallization. For example, the culture is centrifuged at a low speed to remove biomass, and a resulting supernatant is subjected to ion chromatography for isolation.

The method of preparing the yeast cell producing lactate may include introducing a gene encoding a polypeptide that converts pyruvate to lactate. In this regard, the "polypeptide that converts pyruvate to lactate" and the "gene encoding the polypeptide that converts pyruvate to lactate" are the same as described above. The introduction of the gene may be mediated by a vehicle such as a vector. The introduction may be a transient introduction in which the gene is not integrated into a genome, or an integration of the gene into the genome. The introduction may be performed, for example, by introducing a vector into the cell, in which the vector includes a polynucleotide encoding a target polypeptide, and then, replicating the vector in the cell, or by integrating the polynucleotide into the genome.

The culturing may be performed in a medium containing a carbon source, for example, glucose. The medium used for culturing the yeast cell may be any general medium that is suitable for host cell growth, such as a minimal or complex medium containing proper supplements. The suitable medium may be commercially available or prepared by a known preparation method. The medium used for the culturing may be a medium that satisfies the requirements of a particular yeast cell. The medium may be a medium comprising components selected from the group consisting of a carbon source, a nitrogen source, a salt, trace elements and combinations thereof.

The culturing conditions may be properly controlled in order to obtain lactate from the genetically engineered yeast cell. For proliferation, the cell may be cultured under aerobic conditions. Thereafter, the cell may be cultured under microaerobic conditions or anaerobic conditions in order to produce lactate. The term "anaerobic conditions" means oxygen deficient conditions. The term "microaerobic conditions", when used in reference to culture or growth conditions, means that the concentration of dissolved oxygen (DO) in a liquid medium is more than 0% and less than about 10% of saturation, wherein "saturation" refers to the maximum capacity of the medium for DO. The microaerobic conditions also include an atmospheric oxygen concentration of less than 1% in, for example, a sealed culture chamber or incubator. The percentage of oxygen may be maintained by, for example, sparging the culture with an $N_2/CO_2$ mixture or other suitable non-oxygen gas. The oxygen conditions include maintaining the concentration of DO at 0% to 10%, for example, 0 to 8%, 0 to 6%, 0 to 4%, or 0 to 2%.

The term "culture conditions" means conditions for culturing the yeast cell. Such culture conditions may include, for example, a carbon source, a nitrogen source, or an oxygen condition utilized by the yeast cell. The carbon source that may be utilized by the yeast cell may include monosaccharides, disaccharides, or polysaccharides. The carbon source may be glucose, fructose, mannose, or galactose. The nitrogen source that may be utilized by the yeast cell may be an organic nitrogen compound or an inorganic nitrogen compound. The nitrogen source may be exemplified by amino acids, amides, amines, nitrates, or ammonium salts.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, the present invention will be described in more detail with reference to the exemplary embodiments. However, the exemplary embodiments described herein should be considered in a descriptive sense only and not for purposes of limitation.

EXAMPLE 1

Effects of Lactic Acid on Glucose Consumption and Lactic Acid Production in *Saccharomyces*

In this Example, *Saccharomyces cerevisiae* is cultured in the presence of D-lactic acid, a glucose consumption rate and a lactic acid production are measured to examine effects of D-lactic acid on glucose consumption and lactic acid production in *Saccharomyces cerevisiae.*

First, in order to examine whether glucose consumption and lactic acid production are inhibited by lactic acid in *Saccharomyces cerevisiae, Saccharomyces cerevisiae* CEN.PK2-1D (Δpdc1::ldh, Δgpd1::ldh, Δdld1::ldh, Δpdc6::ldh, Δadh1, Δald6::EcEutE, Δadh5::rck1) strain (hereinafter, referred to as "SP3027 strain", a preparation method thereof is described in Example 2) is subjected to D-lactic acid inhibition assay.

In detail, the SP3027 strain is cultured on an YPD agar plate at 30° C. for 2 days, and then a single colony is cultured in YPD broth to the stationary phase. A culture broth thus obtained is washed with distilled water, and resuspended in an SD (pH 3.0) medium to measure cell density. The cultured cells are added to 1 ml of SD (60 g/L glucose, pH 3.0) containing 0 g/L, 20 g/L, or 40 g/L of D-lactic acid (D-LA). After $OD_{600}$ is set at 15.0, the cells are cultured in a 12-well plate at 30° C., 90 rpm, and sugar consumption and D-LA production over time are measured.

Figure 1B:
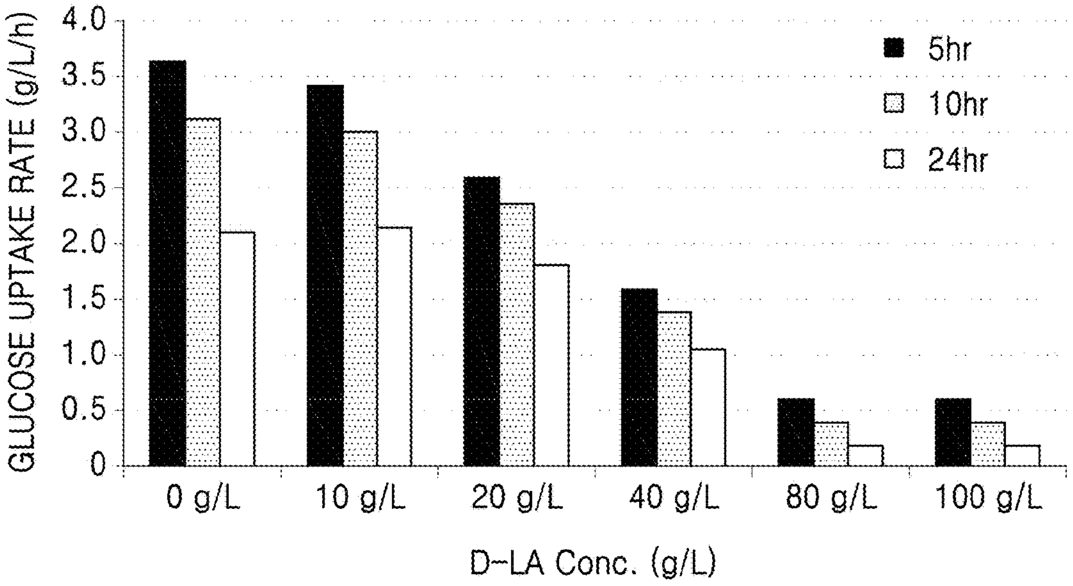
FIG. 1B shows a glucose uptake rate (g/L/h) at various time points in yeast culture spiked with 0, 10, 20, 40, 80, or 100 g/L D-lactic acid.
Figure 1C:
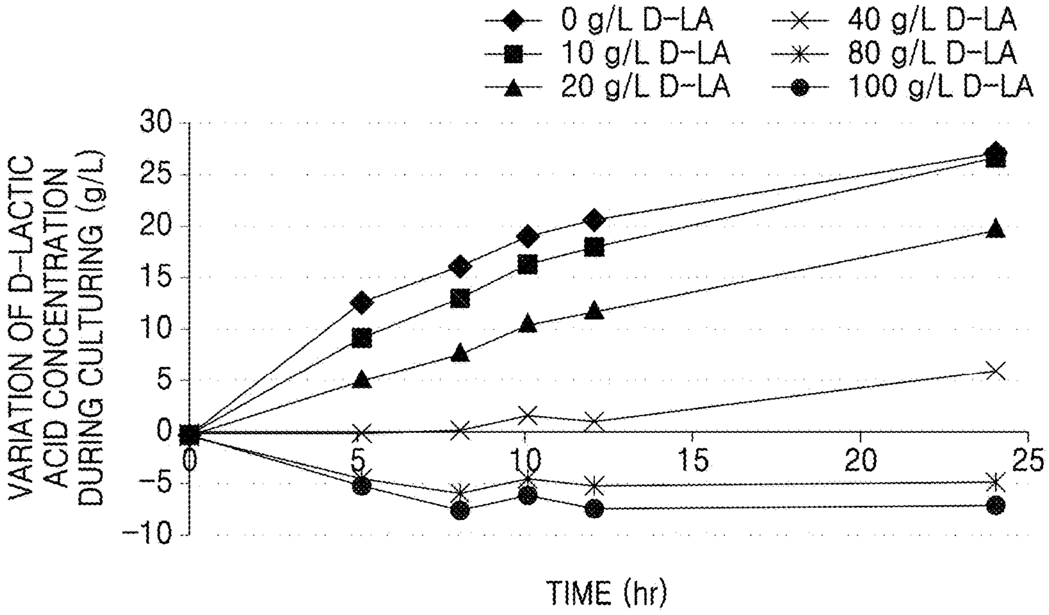
FIG. 1C shows D-lactic acid concentration (g/L) over time in yeast culture spiked with 0, 10, 20, 40, 80, or 100 g/L D-lactic acid.
Figure 1D:
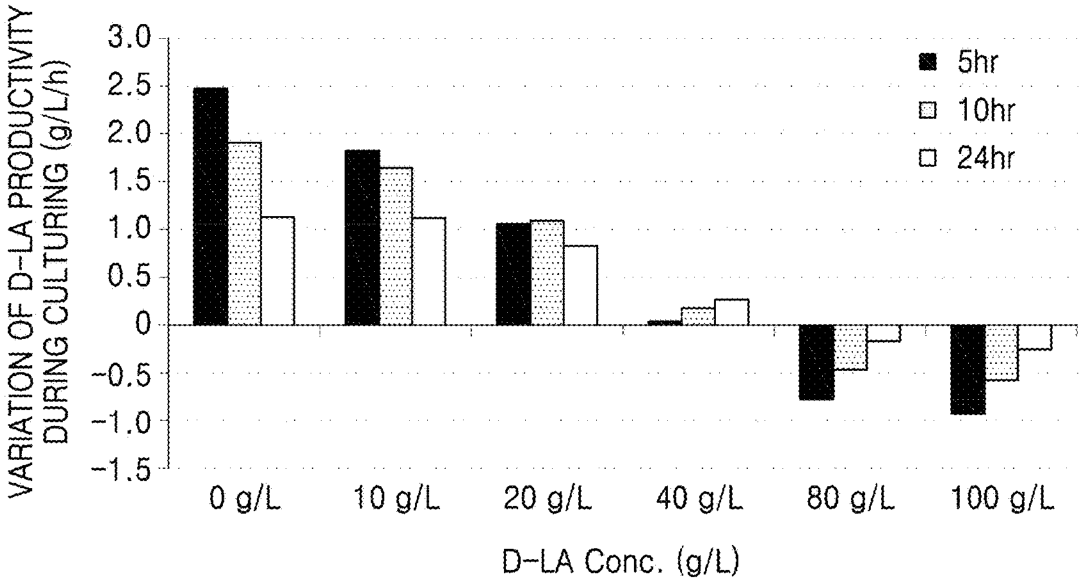
FIG. 1D shows D-lactic acid productivity (g/L/h) over time in yeast cultures spiked with increasing concentrations of D-LA.

FIG. 1A shows glucose concentration over time in yeast culture spiked with 0, 10, 20, 40, 80, or 100 g/L D-LA, FIG. 1B shows a glucose uptake rate over time in yeast culture spiked with 0, 10, 20, 40, 80, or 100 g/L D-LA, FIG. 1C shows change in D-LA concentration over time in yeast culture spiked with 0, 10, 20, 40, 80, or 100 g/L D-LA, and FIG. 1D shows D-LA productivity over time in yeast cultures spiked with increasing concentrations of D-LA. As shown in FIGS. 1A through 1D, glucose consumption and D-LA production are found to be inhibited by extracellular D-LA. As shown in FIGS. 1B and 1D, inhibition of D-LA productivity by D-LA is found to be higher than inhibition of glucose consumption by D-LA. As shown in FIG. 1C, as the concentration of extracellular D-LA is increased, inhibition of D-LA production is increased.

EXAMPLE 2

Preparation of D-Lactate-Producing Strain

*Saccharomyces cerevisiae* CEN.PK2-1D wild-type strain (MATαura3-52; trp1-289; leu2-3,112; his3Δ1; MAL2-8C; SUC2, EUROSCARF accession number: 30000B) was modified as follows to produce a lactate-producing strain:

1. Preparation of *S. cerevisiae* CEN.PK2-1D (Δpdc1::ldh)

1.1. Preparation of Vector for pdc1 Deletion and ldh Introduction

To block a pathway of converting pyruvate to ethanol via acetaldehyde in *Saccharomyces cerevisiae* CEN.PK2-1D, a pyruvate decarboxylase 1 (pyruvate decarboxylase1: pdc1)-encoding gene is deleted. To delete the pdc1 gene and express LbLdh at the same time, the pdc1 gene is replaced with 'ldh cassette' so as to delete the pdc1 gene. Unless otherwise specified, the "cassette" refers to a unit sequence capable of expressing a protein, in which a promoter, a coding sequence, and a terminator are operably linked to the unit sequence.

In detail, to prepare an 'ldh cassette'-containing vector, a CCW12 promoter sequence (SEQ ID NO: 53) which is obtained by PCR using genomic DNA of *Saccharomyces cerevisiae* as a template and a primer set of SEQ ID NOS: 56 and 57 as primers, and 'ldh gene (SEQ ID NO: 26)' are digested with SacI/XbaI and BamHI/SalI, respectively and ligated to a pRS416 vector (ATCC87521™) which is digested with the same enzymes. The pRS416 vector is a yeast centromere shuttle plasmid having a T7 promoter, an ampicillin resistance in bacteria and a URA3 cassette in yeast as a selection marker, and restriction enzyme cloning sites.

Next, PCR is performed using a pCEP4 plasmid (Invitrogen, Cat. no. V044-50) as a template and a primer set of SEQ ID NOS: 58 and 59 as primers to amplify an "HPH cassette" sequence (SEQ ID NO: 60). The amplified "HPH cassette" and the pRS416 vector are digested with SacI enzyme, respectively and ligated to each other so as to prepare a p416-ldh-HPH vector containing a structure of operably linking the 'ldh cassette' and the "HPH cassette". The pCEP4 plasmid is an episomal mammalian expression vector that uses the cytomegalovirus (CMV) immediate early enhancer/promoter for high level transcription of recombinant genes inserted into the multiple cloning site. pCEP4 has a hygromycin B resistance gene for stable selection in transfected cells. Here, the 'ldh cassette' represents a region that allows the ldh gene to be expressed, because it contains the ldh gene and its regulatory region. Transcription of the ldh gene is allowed in the presence of the CCW12 promoter. Further, the 'HPH (hygromycin B phosphotransferase) cassette' represents a region that allows the hygromycin B resistance gene to be expressed, because it contains the hygromycin B resistance gene and its regulatory region.

A pdc1 deletion vector is prepared by PCR using p416-ldh-HPH as a template and a primer set of SEQ ID NOS: 61 and 62 as primers. ldh gene fragment and pUC57-Ura3HA vector (DNA2.0 Inc.; SEQ ID NO: 63) are digested with SacI, respectively and ligated to each other so as to prepare pUC-uraHA-ldh. From this vector, a pdc1 deletion cassette is amplified by PCR using a primer set of SEQ ID NOS: 64 and 65 having a homologous sequence with the pdc1 gene.

1.2. Preparation of *cerevisiae* CEN.PK2-1D (Δpdc1::ldh)

The pdc1 deletion cassette prepared in 1.1 is introduced into *Saccharomyces cerevisiae* (CEN.PK2-1D, EUROSCARF accession number: 30000B). Introduction of the pdc1 deletion cassette is performed by general heat shock transformation. After transformation, cells are cultured in a uracil dropout medium to replace pdc1 ORF on the chromosome with the cassette.

To examine the pdc1 deletion in the resulting cells, PCR is performed using the genome of the cell as a template and a primer set of SEQ ID NOS: 66 and 67 to confirm pdc1 gene deletion and ldh gene introduction. As a result, *S. cerevisiae* CEN.PK2-1D (Δpdc1::$P_{ccw12}$-Lbldh) is identified.

2. Preparation of *S. cerevisiae* CEN.PK2-1D (Δpdc1::ldh, Δgpd1::ldh)

2.1. Preparation of Vector for gpd1 Deletion

To block a pathway of converting dihydroxyacetone phosphate (DHAP) to glycerol-3-phosphate in *S. cerevisiae* CEN.PK2-1D (Δpdc1::ldh) prepared in 1 of Example 2, a glycerol-3-phosphate dehydrogenase (gpd1)-encoding gene is deleted.

In detail, PCR is performed using pUC-uraHA-ldh prepared in 1.1 of Example 2 as a template and gpd1 homologous recombination sequences of SEQ ID NOS: 68 and 69 as primers so as to prepare a gpd1 deletion cassette.

2.2. Preparation of *S. cerevisiae* CEN.PK2-1D (Δpdc1::ldh, Δgpd1::ldh)

The gpd1 deletion cassette prepared in 2.1 is introduced into *S. cerevisiae* CEN.PK2-1D (Δpdc1::ldh) prepared in 1 of Example 2. Introduction is performed by general heat shock transformation. After transformation, cells are cultured in a uracil dropout medium to replace gpd1 ORF on the chromosome with the cassette.

To examine the gpd1 deletion in the resulting cells, PCR is performed using the genome of the cell as a template and a primer set of SEQ ID NOS: 70 and 71 to confirm gpd1 gene deletion. As a result, *S. cerevisiae* CEN.PK2-1D (Δpdc1::ldh, Δgpd1::ldh) is identified.

3. Preparation of *S. cerevisiae* CEN.PK2-1D (Δpdc1::ldh, Δgpd1::ldh, Δdld1::ldh)

3.1. Preparation of Vector for dld1 Deletion

To block a pathway of converting d-lactate to pyruvate in *S. cerevisiae* CEN.PK2-1D (Δpdc1::ldh, Δgpd1::ldh) prepared in 2 of Example 2, a dld1 gene is deleted.

In detail, PCR is performed using pUC-uraHA-ldh prepared in 1.1 of Example 2 as a template and dld1 homologous recombination sequences of SEQ ID NOS: 72 and 73 as primers so as to prepare a dld1 deletion cassette.

3.2. Preparation of *S. cerevisiae* CEN.PK2-1D (Δpdc1::ldh, Δgpd1::ldh, Δdld1::dh)

The dld1 deletion cassette prepared in 3.1 is introduced into *S. cerevisiae* CEN.PK2-1D (Δpdc1::ldh, Δgpd1::ldh). Introduction is performed by general heat shock transformation. After transformation, cells are cultured in a uracil dropout medium to replace dld1 ORF on the chromosome with the cassette.

To examine the dld1 deletion in the resulting cells, PCR is performed using the genome of the cell as a template and a primer set of SEQ ID NOS: 74 and 75 to confirm dld1 gene deletion. As a result, *S. cerevisiae* CEN.PK2-1D (Δpdc1::ldh, Δgpd1::ldh, Δdld1::ldh) is identified.

4. Preparation of *S. cerevisiae* CEN.PK2-1D (Δpdc1::ldh, Δgpd1::ldh, Δdld1::ldh, Δpdc6::ldh)

4.1. Preparation of pdc6 Gene Deletion Cassette

PCR is performed using genomic DNA of *S. cerevisiae* CEN.PK2-1D as a template and a primer set of SEQ ID NOS: 76 and 77 as primers to amplify an HHT2 gene promoter. An amplification product of the HHT2 gene promoter (SEQ ID NO: 54) and the prepared ldh gene (SEQ ID NO: 26) (DNA2.0 Inc., USA) are cleaved with SacI/XbaI and BamHI/SalI, respectively and then ligated to the pRS416 vector (ATCC87521™) which has been cleaved with the same enzymes.

The "HPH cassette" and the pRS416 vector containing the HHT2 gene promoter are cleaved with SacI enzyme, respectively and ligated to each other so as to prepare a p416-ldh-HPH vector. A pdc6 deletion cassette is prepared by PCR using the p416-ldh-HPH vector as a template and a primer set of SEQ ID NOS: 78 and 79 as primers.

4.2. Preparation of *S. cerevisiae* CEN.PK2-1D (Δpdc1::ldh, Δgpd1::ldh, Δdld1::ldh, Δpdc6::ldh)

To replace the pdc6 gene with the ldh gene in *S. cerevisiae* CEN.PK2-1D, the "pdc6 deletion cassette" prepared in 4.1 is introduced into *S. cerevisiae* CEN.PK2-1D (Δpdc1::ldh, Δgpd1::ldh, Δdld1::ldh) by heat shock transformation, and cultured in an YPD medium (Yeast extract 1 (w/v) %, peptone 1 (w/v) %, and glucose 2 (w/v) %) containing 200 ug/mL of hygromycin at 30° C. for 3 days for replacement of the chromosomal pdc6 gene with the ldh gene, thereby preparing *S. cerevisiae* CEN.PK2-1D (Δpdc1::ldh, Δgpd1::ldh, Δdld1::ldh, Δgpd6::ldh) strain. To examine the pdc6 deletion in the resulting strain, PCR is performed using the genome of the cell as a template and a primer set of SEQ ID NOS: 80 and 81 as primers to confirm pdc6 gene deletion.

5. Preparation of *S. cerevisiae* CEN.PK2-1D (Δpdc1::ldh, Δgpd1::ldh, Δdld1::ldh, Δpdc6::ldh, Δadh1)

An adh1 gene deletion cassette is amplified by PCR using a deletion vector pUC57-ura3HA as a template and a primer set of SEQ ID NOS: 82 and 83 as primers.

To delete the adh1 gene in *S. cerevisiae* CEN.PK2-1D (Δpdc1::ldh, Δgpd1::ldh, Δdld1::ldh, Δpdc6::ldh) strain, the prepared "adh1 deletion cassette" is introduced into the strain by heat shock transformation. After heat shock, the strain is cultured in a minimal ura-drop out medium as a selection marker at 30° C. for 3 days to delete adh1 gene on the chromosome. For genotyping of the prepared strain, PCR is performed using a genome of the prepared strain as a template and a primer set of SEQ ID NOS: 84 and 85 to examine deletion of the adh1 gene. As a result, *S. cerevisiae* CEN.PK2-1D (Δpdc1::ldh, Δgpd1::ldh, Δdld1::ldh, Δpdc6::ldh, Δadh1) strain is identified.

6. Preparation of *S. cerevisiae* CEN.PK2-1D (Δpdc1::ldh, Δgpd1::ldh, Δdld1::ldh, Δpdc6::ldh, Δadh1, Δald6::EcEutE)

6.1. Preparation and Introduction of Vector for ald6 Deletion

An acetaldehyde dehydrogenase 6 (ald6) gene deletion cassette is amplified by PCR using a deletion vector pUC57-ura3HA as a template and a primer set of SEQ ID NOS: 86 and 87 as primers. The sequences of SEQ ID NOS: 86 and 87 include a region which is substituted for the ald6 gene by recombination with a homologous sequence of a chromosome of *S. cerevisiae*.

6.2. Preparation of *S. cerevisiae* CEN.PK2-1D (Δpdc1::ldh, Δcyb2::ldh, Δgpd1::ldh, Δadh1, Δaid6) Strain To delete the ald6 gene in *S. cerevisiae* CEN.PK2-1D (Δpdc1::ldh, Δgpd1::ldh, Δdld1::ldh, Δpdc6::ldh, Δadh1) strain, the "ald6 deletion cassette" prepared in 6.1 is introduced into the strain by heat shock transformation. After heat shock, the strain is cultured in a minimal ura-drop out medium as a selection marker at 30° C. for 3 days to delete ald6 gene on the chromosome. For genotyping of the prepared strain, PCR is performed using a genome of the prepared strain as a template and a primer set of SEQ ID NOS: 88 and 89 to examine deletion of the ald6 gene.

As a result, *S. cerevisiae* CEN.PK2-1D (Δpdc1::ldh, Δgpd1::ldh, Δdld1::ldh, Δpdc6::ldh, Δadh1, Δald6) strain is identified.

6.3. Preparation of Yeast Dual Function Overexpression Vector, pCS-Ex1

PCR is performed using a pRS426GPD vector which is widely used as a yeast overexpression vector and a primer set of SEQ ID NO: 90 and SEQ ID NO: 91 to obtain a DNA fragment of 689 bp (GPD promoter). This DNA fragment is cloned into a KpnI-treated pCtB1 vector (Genbank Accession Number KJ922019) using an In-fusion kit (Clonetech, cat. 639650), and introduced into an *E. coli* cloning strain, TOP10 strain (Invitrogen, cat. C4040-06) by a general method. After introduction, the strain is plated on an LB agar plate (Bacto Tryptone 10 g/L, Yeast Extract 5 g/L, NaCl 10 g/L, and Bacto Agar 15 g/L) containing 50 ug/ml of kanamycin, followed by incubation. From colonies formed, plasmid DNAs are isolated, and plasmids having the same sequence as SEQ ID NO: 92 are examined. As a result, a yeast dual function overexpression vector, pCS-Ex1 is identified. Here, the dual function includes a gene expression after genomic integration of a gene and a gene expression on a vector.

6.4. Preparation of Yeast Dual Function eutE Gene Overexpression Vector

PCR is performed using genomic DNA of *E. coli* MG1655 strain and a primer combination of SEQ ID NOS: 93 and 94 so as to obtain a DNA fragment of 1447 bp, that is, EutE gene. This DNA fragment is cloned into a pCS-Ex1 vector which is treated with KpnI and SacI, using an In-fusion kit (Clonetech cat. 639650), and introduced into an *E. coli* cloning strain, TOP10 strain (Invitrogen, cat. C4040-06) by a general method. After introduction, the strain is plated on an LB agar plate containing 50 ug/ml of kanamycin, followed by incubation. From colonies formed, plasmid DNAs are isolated, and plasmids having the same sequence as SEQ ID NO: 95 are examined. As a result, a yeast dual function eutE gene overexpression vector, MD1040 is identified.

6.5. Preparation of eutE Gene-Overexpressing Yeast

From the prepared MD1040 vector, a DNA fragment of 3985 bp is obtained by PCR using a primer combination of SEQ ID NOS: 96 and 97. This fragment is introduced into *S. cerevisiae* CEN.PK2-1D (Δpdc1::ldh, Δgpd1::ldh, Δdld1::ldh, Δpdc6::ldh, Δadh1, Δald6) by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, colonies which are confirmed to have a DNA fragment of 4,357 bp by PCR using a primer combination of SEQ ID NOS: 98 and 99 are selected. From genomic DNA of a native strain, a DNA fragment of 2,300 bp is obtained by PCR using a primer combination of SEQ ID NOS: 98 and 99. The obtained clones are inoculated in an YPD medium (Bacto Peptone 20 g/L, Yeast Extract 10 g/L, and D-glucose 20 g/L), and cultured at 30° C. under shaking at 230 rpm, and then plated on a counter-selection medium containing 5-FOA (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, Uracil 0.1 g/L, D-glucose 20 g/L, 5-fluoroorotic acid (5-FOA) 1 g/L, and Bacto Agar 20 g/L). After 3 days, from colonies formed, colonies which are confirmed to have a DNA fragment of 2,963 bp by PCR using a primer combination of SEQ ID NOS: 100 and 101 are selected.

As a result, *S. cerevisiae* CEN.PK2-1D (Δpdc1::ldh, Δgpd1::ldh, Δdld1::ldh, Δpdc6::ldh, Δadh1, Δald6::EcEutE) is identified.

7. Preparation of *S. cerevisiae* CEN.PK2-1D (Δpdc1::ldh, Δgpd1::ldh, Δdld1::ldh, Δpdc6::ldh, Δadh1, Δald6::EcEutE, Δadh5::rck1)

7.1. Preparation of Yeast Dual Function rck1 Gene Overexpression Vector

PCR is performed using genomic DNA of *Saccharomyces cerevisiae* and a primer combination of SEQ ID NOS: 102 and 103 so as to obtain a RCK1 gene. This DNA fragment is cloned into a pCS-Ex1 vector which is treated with KpnI and SacI, using an In-fusion kit (Clonetech cat. 639650), and introduced into an *E. coli* cloning strain, TOP10 strain (Invitrogen, cat. C4040-06) by a general method. After introduction, the strain is plated on an LB agar plate containing 50 ug/ml of kanamycin, followed by incubation. From colonies formed, plasmid DNAs are isolated, and plasmids having the same sequence as RCK1 are examined. As a result, a yeast dual function RCK1 gene overexpression vector, MD1167 is identified.

7.2. Preparation of RCK1 Gene-Overexpressing Yeast

From the prepared MD1167 vector, a cassette fragment for RCK1 introduction is obtained by PCR using a primer combination of SEQ ID NOS: 104 and 105. This fragment is introduced into *S. cerevisiae* CEN.PK2-1D (Δpdc1::ldh, Δgpd1::ldh, Δdld1::ldh, a pdc6::ldh, Δadh1, Δald6) by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, a strain having an insertion of a RCK1 gene at ADL6 position is confirmed using a primer combination of SEQ ID NOS: 106 and 107. The obtained clones are inoculated in an YPD medium (Bacto Peptone 20 g/L, Yeast Extract 10 g/L, and D-glucose 20 g/L), and cultured at 30° C. under shaking at 230 rpm, and then plated on a counter-selection medium containing 5-FOA (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, Uracil 0.1 g/L, D-glucose 20 g/L, 5-fluoroorotic acid (5-FOA) 1 g/L, and Bacto Agar 20 g/L). After 3 days, from colonies formed, a strain having a deletion of URA3 gene is confirmed by PCR using a primer combination of SEQ ID NOS: 106 and 107. As a result, *S. cerevisiae* CEN.PK2-1D (Δpdc1::ldh, Δgpd1::ldh, Δdld1::ldh, Δpdc6::ldh, Δadh1, Δald6::RCK1) (hereinafter, referred to as 'SP3027') is identified.

EXAMPLE 3

Preparation of Overexpressing Strains

1. Preparation of Sul1-Overexpressing Strain

To prepare a vector containing a cassette for replacing a promoter of SUL1 gene with a promoter of CCW12 gene, SUL1 upstream and downstream regions are amplified using genomic DNA of *Saccharomyces cerevisiae* as a template and primer sets of SEQ ID NOS: 108 and 109 and SEQ ID NOS: 110 and 111 as primers. These DNA fragments are cloned into a pMSK+ vector (Genbank Accession Number KJ922019) treated with XhoI and XbaI using an In-fusion kit (Clonetech, cat. 639650), and introduced into an *E. coli* cloning strain, TOP10 strain (Invitrogen, cat. C4040-06) by a general method. A PCR fragment amplified using a pCS-EX1 vector as a template and a primer set of SEQ ID NOS: 112 and 113 as primers is cloned into the EcoRI site of the prepared pMSK-SUL1 vector using the In-fusion kit (Clonetech cat. 639650), and then introduced into an *E. coli* cloning strain, TOP10 strain (Invitrogen, cat. C4040-06) by a general method. As a result, a pCCW12-SUL1 vector which is a vector containing a cassette for replacing the promoter of SUL1 gene with the promoter of CCW12 gene is obtained.

From the prepared pCCW12-SUL1 vector, a cassette fragment for replacement of CCW12 promoter is obtained by PCR using a primer combination of SEQ ID NOS: 108 and 111. This fragment is introduced into SP3027 by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, a strain having replacement of SUL1 promoter with CCW12 promoter is identified by using a primer combination of SEQ ID NOS: 114 and 115.

2. Preparation of Str3-Overexpressing Strain

To prepare a vector containing a cassette for replacing a promoter of STR3 gene with a promoter of CCW12 gene, STR3 upstream and downstream regions are amplified using genomic DNA of *Saccharomyces cerevisiae* as a template and primer sets of SEQ ID NOS: 116 and 117 and SEQ ID NOS: 118 and 119 as primers. These DNA fragments are cloned into a pMSK+ vector treated with XhoI and XbaI using an In-fusion kit (Clonetech, cat. 639650), and introduced into an *E. coli* cloning strain, TOP10 strain (Invitrogen, cat. C4040-06) by a general method. A PCR fragment amplified using a pCS-EX1 vector as a template and a primer set of SEQ ID NOS: 120 and 121 as primers is cloned into the EcoRI site of the prepared pMSK-STR3 vector using the In-fusion kit (Clonetech cat. 639650), and then introduced into an *E. coli* cloning strain, TOP10 strain (Invitrogen, cat. C4040-06) by a general method. As a result, a pCCW12-STR3 vector which is a vector containing a cassette for replacing the promoter of STR3 gene with the promoter of CCW12 gene is obtained.

From the prepared pCCW12-STR3 vector, a cassette fragment for replacement of CCW12 promoter is obtained by PCR using a primer combination of SEQ ID NOS: 116 and 119. This fragment is introduced into SP3027 by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, a strain having replacement of STR3 promoter with CCW12 promoter is identified by using a primer combination of SEQ ID NOS: 114 and 122.

3. Preparation of hxt7-Overexpressing Strain

To prepare a vector containing a cassette for replacing a promoter of HXT7 gene with a promoter of CCW12 gene, HXT7 upstream and downstream regions are amplified using genomic DNA of *Saccharomyces cerevisiae* as a template and primer sets of SEQ ID NOS: 123 and 124 and SEQ ID NOS: 125 and 126 as primers. These DNA fragments are cloned into a pMSK+ vector treated with XhoI and XbaI using an In-fusion kit (Clonetech, cat. 639650), and introduced into an *E. coli* cloning strain, TOP10 strain (Invitrogen, cat. C4040-06) by a general method. A PCR fragment amplified using a pCS-EX1 vector as a template and a primer set of SEQ ID NOS: 127 and 128 as primers is cloned into the EcoRI site of the prepared pMSK-HXT7 vector using the In-fusion kit (Clonetech cat. 639650), and then introduced into an *E. coli* cloning strain, TOP10 strain (Invitrogen, cat. C4040-06) by a general method. As a result, a pCCW12-HXT7 vector which is a vector containing a cassette for replacing the promoter of HXT7 gene with the promoter of CCW12 gene is obtained.

From the prepared pCCW12-HXT7 vector, a cassette fragment for replacement of CCW12 promoter is obtained by PCR using a primer combination of SEQ ID NOS: 123 and 126. This fragment is introduced into SP3027 by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, a strain having replacement of HXT7 promoter with CCW12 promoter is identified by using a primer combination of SEQ ID NOS: 114 and 129.

4. Preparation of err1-Overexpressing Strain

To prepare a vector containing a cassette for replacing a promoter of ERR1 gene with a promoter of CCW12 gene, ERR1 upstream and downstream regions are amplified using genomic DNA of *Saccharomyces cerevisiae* as a template and primer sets of SEQ ID NOS: 130 and 131 and SEQ ID NOS: 132 and 133 as primers. These DNA fragments are cloned into a pMSK+ vector treated with XhoI and XbaI using an In-fusion kit (Clonetech, cat. 639650), and introduced into an *E. coli* cloning strain, TOP10 strain (Invitrogen, cat. C4040-06) by a general method. A PCR fragment amplified using a pCS-EX1 vector as a template and a primer set of SEQ ID NOS: 134 and 135 as primers is cloned into the EcoRI site of the prepared pMSK-ERR1 vector using the In-fusion kit (Clonetech cat. 639650), and then introduced into an *E. coli* cloning strain, TOP10 strain (Invitrogen, cat. C4040-06) by a general method. As a result, a pCCW12-ERR1 vector which is a vector containing a cassette for replacing the promoter of ERR1 gene with the promoter of CCW12 gene is obtained.

From the prepared pCCW12-ERR1 vector, a cassette fragment for replacement of CCW12 promoter is obtained by PCR using a primer combination of SEQ ID NOS: 130 and 133. This fragment is introduced into SP3027 by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, a strain having replacement of ERR1 promoter with CCW12 promoter is identified by using a primer combination of SEQ ID NOS: 114 and 136.

5. Preparation of grx8-Overexpressing Strain

To prepare a vector containing a cassette for replacing a promoter of GRX8 gene with a promoter of CCW12 gene, GRX8 upstream and downstream regions are amplified using genomic DNA of *Saccharomyces cerevisiae* as a template and primer sets of SEQ ID NOS: 137 and 138 and SEQ ID NOS: 139 and 140 as primers. These DNA fragments are cloned into a pMSK+ vector treated with XhoI and XbaI using an In-fusion kit (Clonetech, cat. 639650), and introduced into an *E. coli* cloning strain, TOP10 strain (Invitrogen, cat. C4040-06) by a general method. A PCR fragment amplified using a pCS-EX1 vector as a template and a primer set of SEQ ID NOS: 141 and 142 as primers is cloned into the EcoRI site of the prepared pMSK-GRX8 vector using the In-fusion kit (Clonetech cat. 639650), and then introduced into an *E. coli* cloning strain, TOP10 strain (Invitrogen, cat. C4040-06) by a general method. As a result, a pCCW12-GRX8 vector which is a vector containing a cassette for replacing the promoter of GRX8 gene with the promoter of CCW12 gene is obtained.

From the prepared pCCW12-GRX8 vector, a cassette fragment for replacement of CCW12 promoter is obtained by PCR using a primer combination of SEQ ID NOS: 137 and 140. This fragment is introduced into SP3027 by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, a strain having replacement of GRX8 promoter with CCW12 promoter is identified by using a primer combination of SEQ ID NOS: 114 and 143.

6. Preparation of mxr1-Overexpressing Strain

To prepare a vector containing a cassette for replacing a promoter of MXR1 gene with a promoter of CCW12 gene, MXR1 upstream and downstream regions are amplified using genomic DNA of *Saccharomyces cerevisiae* as a template and primer sets of SEQ ID NOS: 144 and 145 and SEQ ID NOS: 146 and 147 as primers. These DNA fragments are cloned into a pMSK+ vector treated with XhoI and XbaI using an In-fusion kit (Clonetech, cat. 639650), and introduced into an *E. coli* cloning strain, TOP10 strain (Invitrogen, cat. C4040-06) by a general method. A PCR fragment amplified using a pCS-EX1 vector as a template and a primer set of SEQ ID NOS: 148 and 149 as primers is cloned into the EcoRI site of the prepared pMSK-MXR1 vector using the In-fusion kit (Clonetech cat. 639650), and then introduced into an *E. coli* cloning strain, TOP10 strain (Invitrogen, cat. C4040-06) by a general method. As a result, a pCCW12-MXR1 vector which is a vector containing a cassette for replacing the promoter of MXR1 gene with the promoter of CCW12 gene is obtained.

From the prepared pCCW12-MXR1 vector, a cassette fragment for replacement of CCW12 promoter is obtained by PCR using a primer combination of SEQ ID NOS: 144 and 147. This fragment is introduced into SP3027 by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, a strain having replacement of MXR1 promoter with CCW12 promoter is identified by using a primer combination of SEQ ID NOS: 114 and 150.

7. Preparation of gre1-Overexpressing Strain

To prepare a vector containing a cassette for replacing a promoter of GRE1 gene with a promoter of CCW12 gene, GRE1 upstream and downstream regions are amplified using genomic DNA of *Saccharomyces cerevisiae* as a template and primer sets of SEQ ID NOS: 151 and 152 and SEQ ID NOS: 153 and 154 as primers. These DNA fragments are cloned into a pMSK+ vector treated with XhoI and XbaI using an In-fusion kit (Clonetech, cat. 639650), and introduced into an *E. coli* cloning strain, TOP10 strain (Invitrogen, cat. C4040-06) by a general method. A PCR fragment amplified using a pCS-EX1 vector as a template and a primer set of SEQ ID NOS: 155 and 156 as primers is cloned into the EcoRI site of the prepared pMSK-GRE1 vector using the In-fusion kit (Clonetech cat. 639650), and then introduced into an *E. coli* cloning strain, TOP10 strain (Invitrogen, cat. C4040-06) by a general method. As a result, a pCCW12-GRE1 vector which is a vector containing a cassette for replacing the promoter of GRE1 gene with the promoter of CCW12 gene is obtained.

From the prepared pCCW12-GRE1 vector, a cassette fragment for replacement of CCW12 promoter is obtained by PCR using a primer combination of SEQ ID NOS: 151 and 154. This fragment is introduced into SP3027 by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, a strain having replacement of GRE1 promoter with CCW12 promoter is identified by using a primer combination of SEQ ID NOS: 114 and 157.

8. Preparation of mrk1-Overexpressing Strain

To prepare a vector containing a cassette for replacing a promoter of MRK1 gene with a promoter of CCW12 gene, MRK1 upstream and downstream regions are amplified using genomic DNA of *Saccharomyces cerevisiae* as a template and primer sets of SEQ ID NOS: 158 and 159 and SEQ ID NOS: 160 and 161 as primers. These DNA fragments are cloned into a pMSK+ vector treated with XhoI and XbaI using an In-fusion kit (Clonetech, cat. 639650), and introduced into an *E. coli* cloning strain, TOP10 strain (Invitrogen, cat. C4040-06) by a general method. A PCR fragment amplified using a pCS-EX1 vector as a template and a primer set of SEQ ID NOS: 162 and 163 as primers is cloned into the EcoRI site of the prepared pMSK-MRK1 vector using the In-fusion kit (Clonetech cat. 639650), and then introduced into an *E. coli* cloning strain, TOP10 strain (Invitrogen, cat. C4040-06) by a general method. As a result, a pCCW12-MRK1 vector which is a vector containing a cassette for replacing the promoter of MRK1 gene with the promoter of CCW12 gene is obtained.

From the prepared pCCW12-MRK1 vector, a cassette fragment for replacement of CCW12 promoter is obtained by PCR using a primer combination of SEQ ID NOS: 158 and 161. This fragment is introduced into SP3027 by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, a strain having replacement of MRK1 promoter with CCW12 promoter is identified by using a primer combination of SEQ ID NOS: 114 and 164.

9. Preparation of aad10-Overexpressing Strain

To prepare a vector containing a cassette for replacing a promoter of AAD10 gene with a promoter of CCW12 gene, AAD10 upstream and downstream regions are amplified using genomic DNA of *Saccharomyces cerevisiae* as a template and primer sets of SEQ ID NOS: 165 and 166 and SEQ ID NOS: 167 and 168 as primers. These DNA fragments are cloned into a pMSK+ vector treated with XhoI and XbaI using an In-fusion kit (Clonetech, cat. 639650), and introduced into an *E. coli* cloning strain, TOP10 strain (Invitrogen, cat. C4040-06) by a general method. A PCR fragment amplified using a pCS-EX1 vector as a template and a primer set of SEQ ID NOS: 169 and 170 as primers is cloned into the EcoRI site of the prepared pMSK-AAD10 vector using the In-fusion kit (Clonetech cat. 639650), and then introduced into an *E. coli* cloning strain, TOP10 strain (Invitrogen, cat. C4040-06) by a general method. As a result, a pCCW12-AAD10 vector which is a vector containing a cassette for replacing the promoter of AAD10 gene with the promoter of CCW12 gene is obtained.

From the prepared pCCW12-AAD10 vector, a cassette fragment for replacement of CCW12 promoter is obtained by PCR using a primer combination of SEQ ID NOS: 165 and 168. This fragment is introduced into SP3027 by a general method, and then plated on a minimal medium, SD-URA agar plate containing no uracil (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L). After 3 days, from colonies formed, a strain having replacement of AAD10 promoter with CCW12 promoter is identified by using a primer combination of SEQ ID NOS: 114 and 171.

EXAMPLE 4

Measurement of Acid Tolerance of Overexpressing Strain

1. Spotting Assay

In this Example, each of sul1, str3, hxt7, err1, grx8, mxr1, gre1, mrk1, and aad10 gene is introduced into a yeast cell and overexpressed therein, and effects of their overexpression on acid tolerance of the yeast cell are examined.

The SP3027 strain prepared in Example 2 as a control group and the SP3027(sul1+), SP3027(str3+), SP3027 (hxt7+), SP3027(err1+), SP3027(grx8+), SP3027(mxr1+), SP3027(gre1+), SP3027(mrk1+), and SP3027(aad10+) strains prepared in Example 3 as experimental groups are inoculated in 3 ml of YPD (Bacto Peptone 20 g/L, Yeast Extract 10 g/L, D-glucose 20 g/L), respectively and cultured at 30° C. under shaking at about 230 rpm for total 24 hours. After cell density (OD600) is set at 1.0, 5 ul are spotted onto YPD plates containing 2% D-LA, 2.5% D-LA, or 3% D-LA. The plates are incubated at 30° C. for 2 days to observe their growth.

Figure 2:
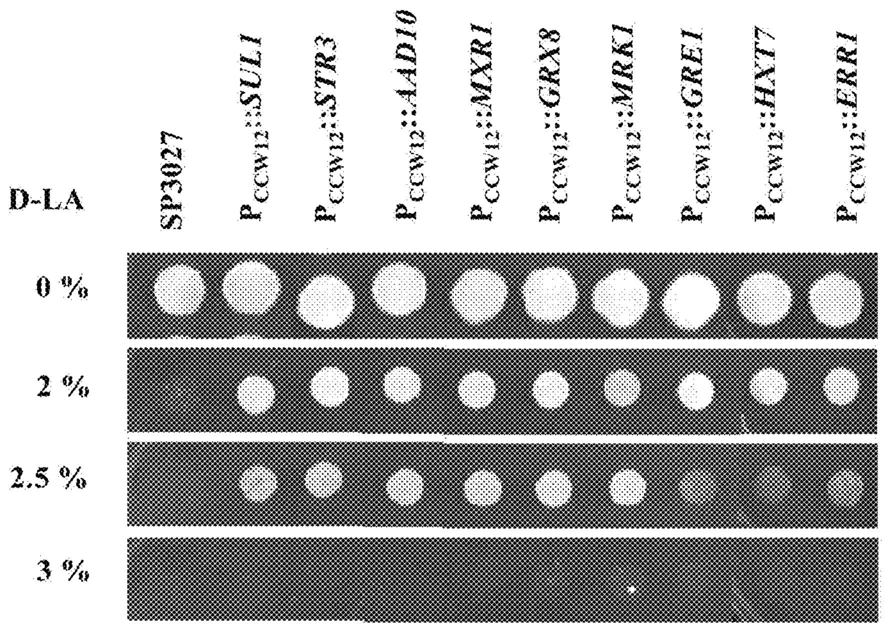
FIG. 2 shows results of culturing various yeast cells on Yeast Extract-Peptone-Dextrose (YPD) acidic media containing lactic acid.

FIG. 2 shows results of culturing various yeast cells on YPD acidic media containing lactic acid. As shown in FIG. 2, the control group was unable to form colonies in media containing D-LA, whereas the sul1, str3, hxt7, err1, grx8, mxr1, gre1, mrk1, or aad10-overexpressing strains formed colonies in media containing 2% D-LA or 2.5% D-LA, suggesting that overexpression of these genes confers acid tolerance.

2. Measurement of Cell Growth and Glucose Consumption

The SP3027 strain as a control group and the SP3027 (sul1+), SP3027(str3+), SP3027(hxt7+), SP3027(err1+), SP3027(grx8+), SP3027(mxr1+), SP3027(gre1+), SP3027 (mrk1+), and SP3027(aad10+) strains prepared in Example 3 as experimental groups are cultured on YPD agar plates for 2 days at 30° C., respectively. Then, single colonies are cultured in YPD broth to stationary phase. Each of the obtained culture broths is washed with distilled water, and then resuspended in an SD/-U (pH 3.0) medium, followed by measurement of cell density. The cultured cells are added to 1 ml of SD/-URA (60 g/L glucose, pH 3.0) containing 0 g/L, 20 g/L, or 40 g/L D-LA, respectively. After OD600 is set at 4.0, the respective cells are cultured in a 12-well plate at 30° C. and 90 rpm, and then glucose consumption and D-LA production are measured over time.

During culture, samples are collected periodically, and the samples are centrifuged at about 13,000 rpm for about 10 minutes. Concentrations of various metabolites, lactate and glucose in supernatants are analyzed by liquid chromatography (HPLC). The culture supernatants are filtered using a 0.45 um-syringe filter, and L-lactate and glucose are quantified using HPLC instrument (Waters e2695 Separation Module instrument equipped with a Waters 2414 Differential Refractometer and a Waters 2998 Photodiode Array Detector (Waters, Milford, Mass.)). As an HPLC column, Aminex HPX-87H Organic Acid Analysis Column (300 mm×7.8 mm; Bio-Rad) equilibrated with 2.5 mM $H_2SO_4$ in water at 60° C. and a flow rate of 0.5 mL/min is used.

Table 2 shows cell density ($OD_{600}$) in SD media with or without 40 g/L D-LA after cells are cultured under microaerobic conditions for 24 hours.

TABLE 2

| Strain | Cell density ($OD_{600}$) in medium containing 0 g/L D-LA | Cell density ($OD_{600}$) in medium containing 40 g/L D-LA |
|---|---|---|
| SP3027 | 6.96 | 3.28 |
| SP3027(sul1+) | 7.72 | 7.08 |
| SP3027(str3+) | 7.62 | 7.02 |
| SP3027(hxt7+) | 7.40 | 6.84 |
| SP3027(err1+) | 7.34 | 7.20 |
| SP3027(grx8+) | 7.44 | 6.44 |
| SP3027(mxr1+) | 7.76 | 6.04 |
| SP3027(gre1+) | 8.48 | 7.14 |
| SP3027(mrk1+) | 7.92 | 6.68 |
| SP3027(aad10+) | 7.40 | 5.68 |

As shown in Table 2, the strains overexpressing sul1, str3, hxt7, err1, grx8, mxr1, gre1, mrk1, or aad10 show an increase in cell density compared to the control group SP3027 when grown in the medium containing 40 g/L D-LA These results indicate that the overexpressing strains have increased D-LA resistance.

Table 3 shows glucose consumption (g/L) in SD media after cells are cultured in the medium under microaerobic conditions for 24 hours.

TABLE 3

| Strain | Glucose consumption (g/L) in medium containing 0 g/L D-LA | Glucose consumption (g/L) in medium containing 40 g/L D-LA |
|---|---|---|
| SP3027 | 18.54 | 7.86 |
| SP3027(sul1+) | 33.63 | 25.30 |
| SP3027(str3+) | 29.80 | 27.69 |
| SP3027(hxt7+) | 31.01 | 24.75 |
| SP3027(err1+) | 31.93 | 28.53 |
| SP3027(grx8+) | 36.39 | 27.82 |
| SP3027(mxr1+) | 31.88 | 26.29 |
| SP3027(gre1+) | 26.85 | 24.59 |
| SP3027(mrk1+) | 35.00 | 28.44 |
| SP3027(aad10+) | 29.52 | 24.34 |

As shown in Table 3, strains overexpressing sul1, str3, hxt7, err1, grx8, mxr1, gre1, mrk1, or aad10 show an increase in glucose consumption in the medium containing 40 g/L D-LA compared to the control group, SP3027. These results indicate that the overexpressing strains having increased D-LA resistance, such that the overexpressing cells cultured in the presence of 40 g/L D-LA show a metabolization ability at a level similar to that of the cells cultured in the absence of D-LA.

3. Measurement of Methionine, Cysteine and S-Adenosyl Methionine Productions

The SP3027 strain as a control group, and the SP3027 (sul1+) and SP3027(str3+) strains prepared in Example 3 as experimental groups are cultured on YPD agar plates for 2 days at 30° C., respectively. Then, single colonies are cultured in YPD broth to stationary phase. Each of the obtained culture broths is washed with distilled water, and then resuspended in an SD/-U (pH 3.0) medium, followed by measurement of cell density. The cultured cells are added to 1 ml of SD/-URA (60 g/L glucose, pH 3.0) containing 0 g/L or 20 g/L D-LA, respectively. After OD600 is set at 4.0, the respective cells are cultured in a 12-well plate at 30° C. and 90 rpm.

During culture, samples are collected, and the samples are centrifuged at about 13,000 rpm for about 10 minutes. Concentrations of methionine, cysteine, and S-adenosyl methionine in supernatants are analyzed by liquid chromatography (HPLC). The culture supernatants are filtered using a 0.45 um-syringe filter, and methionine, cysteine, and S-adenosyl methionine are quantified using HPLC instrument (Waters e2695 Separation Module instrument equipped with a Waters 2414 Differential Refractometer and a Waters 2998 Photodiode Array Detector (Waters, Milford, Mass.)). As an HPLC column, Aminex HPX-87H Organic Acid Analysis Column (300 mm×7.8 mm; Bio-Rad) equilibrated with 2.5 mM $H_2SO_4$ in water at 60° C. and a flow rate of 0.5 mL/min is used.

Table 4 shows intracellular levels (nmol/$10^7$ cells) of methionine, cysteine, and S-adenosyl methionine after cells are cultured in media containing 20 g/L D-LA under microaerobic conditions for about 5 hours.

TABLE 4

| | SP3027 + 0 g/L D-LA | SP3027 + 20 g/L D-LA | SP3027(sul1+) + 20 g/L D-LA | SP3027(str3+) + 20 g/L D-LA |
|---|---|---|---|---|
| Met | 7.57 ± 1.74 | 6.77 ± 0.42 | 9.25 ± 2.10 | 12.67 ± 1.44 |
| Cys | 0.30 ± 0.00 | 0.40 ± 0.23 | 0.57 ± 0.08 | 0.76 ± 0.05 |
| S-adenosyl methionine | 79.82 ± 5.53 | 82.88 ± 3.46 | 270.51 ± 8.16 | 458.42 ± 17.81 |

As shown in Table 4, sul1 or str3-overexpressing strain shows increased concentrations of methionine, cysteine, and S-adenosyl methionine in the medium containing 20 g/L D-LA, compared to the control group SP3027.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A genetically engineered yeast cell comprising a genetic modification that increases the activity of enolase-related protein 1 (ERR1), as compared to a parent cell thereof; and having increased lactic acid tolerance as compared to a parent cell thereof, in which expression of a gene encoding ERR1 is increased compared to a parent cell thereof; the ERR1 belongs to EC 4.2.1.11; and the genetically engineered yeast cell belongs to the genus *Saccharomyces*.

2. The genetically engineered yeast cell of claim 1, comprising a genetic modification within an expression regulatory sequence of a gene encoding ERR1.

3. The genetically engineered yeast cell of claim 1, wherein the amino acid sequence of ERR1 has at least 95% sequence identity to SEQ ID NO: 7, and has 2-phosph-D-glycerate hydro-lyase activity.

4. The genetically engineered yeast cell of claim 1, wherein the gene encoding ERR1 has at least 95% sequence identity to SEQ ID NO: 8, and encodes a protein having 2-phosph-D-glycerate hydro-lyase activity.

5. The genetically engineered yeast cell of claim 1, comprising an increased amount of S-adenosyl methionine, as compared to a parent cell thereof.

6. The genetically engineered yeast cell of claim 1, wherein the genetically engineered yeast cell is *Saccharomyces cerevisiae*.

7. The genetically engineered yeast cell of claim 1, wherein genetically engineered yeast cell comprises a polynucleotide that encodes a polypeptide that converts pyruvate to lactate.

8. The genetically engineered yeast cell of claim 7, wherein the polypeptide that converts pyruvate to lactate is lactate dehydrogenase classified as EC 1.1.1.28 or EC 1.1.1.27.

9. The genetically engineered yeast cell of claim 1, further comprising decreased activity of a polypeptide that converts pyruvate to acetaldehyde, a polypeptide that converts dihydroxyacetone phosphate (DHAP) to glycerol-3-phosphate, a polypeptide that converts lactate to pyruvate, a polypeptide that converts acetaldehyde to ethanol, a polypeptide that converts acetaldehyde to acetate, or a combination thereof, compared to a parent cell thereof.

10. The genetically engineered yeast cell of claim 9, wherein the polypeptide that converts pyruvate to acetaldehyde is pyruvate decarboxylase (PDC) classified as EC 4.1.1.1; the polypeptide that converts DHAP to glycerol-3-phosphate is glycerol-3-phosphate dehydrogenase (GPD) classified as EC 1.1.1.8, EC 1.1.5.3, or EC 1.1.1.94; the polypeptide that converts lactate to pyruvate is D-lactate ferricytochrome C oxidoreductase classified as EC 1.1.2.4 or L-lactate cytochrome-c oxidoreductase classified as EC 1.1.2.3; the polypeptide that converts acetaldehyde to ethanol is alcohol dehydrogenase (ADH) classified as EC 1.1.1.1; and the polypeptide that converts acetaldehyde to acetate is aldehyde dehydrogenase (ALD) classified as EC 1.2.1.4.

11. The genetically engineered yeast cell of claim 1, further comprising increased activity of a polypeptide that converts acetaldehyde to acetyl-CoA, radiation sensitivity complementing kinase, or a combination thereof, wherein the polypeptide that converts acetaldehyde to acetyl-CoA is acylating acetaldehyde dehydrogenase classified as EC 1.2.1.10, as compared to the parent cell thereof.

12. The genetically engineered yeast cell of claim 1, wherein the genetically engineered yeast cell has increased lactic acid tolerance as compared to a parent cell thereof.

13. A method of preparing the genetically engineered yeast cell of claim 1 having lactic acid tolerance, the method comprising genetically modifying a parent *Saccharomyces* yeast cell to overexpress a gene encoding ERR1 as compared to the parent *Saccharomyces* yeast cell.

14. The method of claim 13, further comprising disrupting a gene encoding a polypeptide that converts pyruvate to acetaldehyde, a gene encoding a polypeptide that converts dihydroxyacetone phosphate (DHAP) to glycerol-3-phosphate, a gene encoding a polypeptide that converts lactate to pyruvate, a gene encoding a polypeptide that converts acetaldehyde to ethanol, a gene encoding a polypeptide that converts acetaldehyde to acetate, or a combination thereof.

15. The method of claim 13, further comprising introducing a gene encoding a polypeptide that converts pyruvate to lactate, introducing a gene encoding a polypeptide that converts acetaldehyde to acetyl-CoA, and overexpressing a gene encoding radiation sensitivity complementing kinase.

16. The method of claim 13, wherein the yeast cell is *Saccharomyces cerevisiae*.

17. A method of producing lactate, comprising culturing the genetically engineered yeast cell of claim 7 so as to produce lactate.

18. The method of claim 17, further comprising recovering lactate from the culture.

* * * * *